US010556006B2

(12) United States Patent
Refaeli et al.

(10) Patent No.: US 10,556,006 B2
(45) Date of Patent: *Feb. 11, 2020

(54) COMPOSITIONS AND METHODS FOR MODULATING AN IMMUNE RESPONSE

(71) Applicant: Taiga Biotechnologies, Inc., Aurora, CO (US)

(72) Inventors: Yosef Refaeli, Denver, CO (US); Brian Curtis Turner, Denver, CO (US)

(73) Assignee: TAIGA BIOTECHNOLOGIES, INC., Aurora, CO (US)

( * ) Notice: Subject to any disclaimer, the term of this patent is extended or adjusted under 35 U.S.C. 154(b) by 43 days.

This patent is subject to a terminal disclaimer.

(21) Appl. No.: 15/717,675

(22) Filed: Sep. 27, 2017

(65) Prior Publication Data

US 2018/0092972 A1   Apr. 5, 2018

Related U.S. Application Data

(63) Continuation of application No. 14/461,105, filed on Aug. 15, 2014, now Pat. No. 9,775,897, which is a continuation of application No. 13/777,967, filed on Feb. 26, 2013, now Pat. No. 8,828,723, which is a continuation of application No. 12/550,166, filed on Aug. 28, 2009, now Pat. No. 8,784,825.

(60) Provisional application No. 61/092,708, filed on Aug. 28, 2008.

(51) Int. Cl.
| | | |
|---|---|---|
| A61K 38/00 | (2006.01) | |
| C07K 14/82 | (2006.01) | |
| C07K 14/47 | (2006.01) | |
| C07K 14/00 | (2006.01) | |
| A61K 39/39 | (2006.01) | |

(52) U.S. Cl.
CPC ............ *A61K 39/39* (2013.01); *C07K 14/001* (2013.01); *C07K 14/47* (2013.01); *C07K 14/82* (2013.01); *A61K 38/00* (2013.01); *C07K 2319/02* (2013.01); *C07K 2319/21* (2013.01)

(58) Field of Classification Search
None
See application file for complete search history.

(56) References Cited

U.S. PATENT DOCUMENTS

| | | | |
|---|---|---|---|
| 4,963,489 A | 10/1990 | Naughton et al. | |
| 5,476,996 A | 12/1995 | Wilson et al. | |
| 5,652,122 A | 7/1997 | Frankel et al. | |
| 5,674,980 A | 10/1997 | Frankel et al. | |
| 5,698,767 A | 12/1997 | Wilson et al. | |
| 5,811,301 A | 9/1998 | Cameron | |
| 5,824,837 A | 10/1998 | Chen et al. | |
| 5,847,082 A | 12/1998 | Rother et al. | |
| 5,849,288 A | 12/1998 | Reisner | |
| 6,358,739 B1 | 3/2002 | Baetge et al. | |
| 6,451,558 B1 | 9/2002 | Cooke et al. | |
| 6,451,601 B1 | 9/2002 | Baetge et al. | |
| 6,645,501 B2* | 11/2003 | Dowdy | C07K 14/005 424/192.1 |
| 7,135,287 B1 | 11/2006 | Lonberg et al. | |
| 7,311,920 B1 | 12/2007 | Devico et al. | |
| 7,582,745 B2 | 9/2009 | Sah et al. | |
| 7,767,453 B2 | 8/2010 | Zhang | |
| 8,481,492 B2 | 7/2013 | Edenhofer et al. | |
| 8,784,825 B2* | 7/2014 | Refaeli | C07K 14/82 424/184.1 |
| 8,828,723 B2 | 9/2014 | Refaeli et al. | |
| 9,150,831 B2 | 10/2015 | Cambier et al. | |
| 9,365,825 B2 | 6/2016 | Turner et al. | |
| 9,775,897 B2* | 10/2017 | Refaeli | C07K 14/82 |
| 9,789,135 B2 | 10/2017 | Turner et al. | |
| 2001/0049393 A1 | 12/2001 | Coller et al. | |
| 2002/0076787 A1 | 6/2002 | Baetge et al. | |
| 2002/0098166 A1 | 7/2002 | Havemann et al. | |
| 2002/0155502 A1 | 10/2002 | Balint et al. | |
| 2003/0072794 A1 | 4/2003 | Boulikas | |
| 2003/0138859 A1 | 7/2003 | Barbera-Guillem et al. | |
| 2003/0220286 A1 | 11/2003 | Abruzzese et al. | |
| 2005/0220705 A1 | 10/2005 | Brooks et al. | |
| 2005/0281816 A1 | 12/2005 | Lamping et al. | |
| 2006/0068469 A1 | 3/2006 | Payne et al. | |
| 2006/0115898 A1 | 6/2006 | Zhang et al. | |
| 2006/0154331 A1 | 7/2006 | Avidan et al. | |

(Continued)

FOREIGN PATENT DOCUMENTS

| | | |
|---|---|---|
| AU | 2762802 | 5/2002 |
| AU | 2006304392 B2 | 5/2014 |

(Continued)

OTHER PUBLICATIONS

Canadian Office Action, dated Jul. 4, 2018, issued in Canadian Patent Application No. 2,626,525.
European Office Action, dated Jun. 29, 2018, issued in European Patent Application No. 14779483.8.
Israeli Office Action, dated Jul. 29, 2018, issued in Israeli Patent Application No. 256512.
Israeli Office Action, dated Jul. 30, 2018, issued in Israeli Patent Application No. 241192.
Japanese Office Action, dated Jul. 18, 2018, issued in Japanese Patent Application No. 2017-123838.
European Office Action, dated May 15, 2018, issued in corresponding European Patent Application No. 09747016.5.

(Continued)

*Primary Examiner* — Nicole Kinsey White
(74) *Attorney, Agent, or Firm* — Foley & Lardner LLP

(57) ABSTRACT

Disclosed herein are methods of modulation of the viability of a cell using fusion proteins comprising a transporter peptide sequence and a MYC polypeptide. Further disclosed herein are methods of modulating an immune response using the fusion proteins. Further disclosed herein are methods of identifying agents capable of modulation of the viability of a cell or an immune response. Further disclosed herein are agents and compositions capable of modulation of the viability of a cell or an immune response.

20 Claims, No Drawings
Specification includes a Sequence Listing.

(56) References Cited

U.S. PATENT DOCUMENTS

| | | | |
|---|---|---|---|
| 2006/0156422 | A1 | 7/2006 | Dalrymple et al. |
| 2007/0011753 | A1 | 1/2007 | Ito et al. |
| 2007/0047583 | A1 | 3/2007 | Assa et al. |
| 2007/0067854 | A1 | 3/2007 | Habu et al. |
| 2007/0093420 | A1 | 4/2007 | Yeomans et al. |
| 2007/0098715 | A1 | 5/2007 | Ettenberg et al. |
| 2007/0116691 | A1 | 5/2007 | Cambier et al. |
| 2007/0130628 | A1 | 6/2007 | Brown |
| 2007/0248618 | A1 | 10/2007 | Cohen |
| 2009/0291094 | A1 | 11/2009 | Refaeli et al. |
| 2010/0047217 | A1 | 2/2010 | Refaeli et al. |
| 2010/0055129 | A1 | 3/2010 | Refaeli et al. |
| 2010/0233804 | A1 | 9/2010 | Zhou et al. |
| 2010/0279351 | A1 | 11/2010 | Refaeli |
| 2010/0297763 | A1 | 11/2010 | Cambier et al. |
| 2011/0218210 | A1 | 9/2011 | Refaeli et al. |

FOREIGN PATENT DOCUMENTS

| | | |
|---|---|---|
| CN | 1357620 | 7/2002 |
| CN | 101330830 A | 12/2008 |
| EP | 1 103 615 A1 | 5/2001 |
| EP | 1 357 184 | 10/2003 |
| EP | 1 792 627 | 6/2007 |
| GB | 2 387 599 | 10/2003 |
| JP | 2000-189157 | 7/2000 |
| JP | 2001-518300 | 10/2001 |
| JP | 2002-541786 | 12/2002 |
| JP | 2003-513672 | 4/2003 |
| JP | 2003-514565 | 4/2003 |
| JP | 2004-519245 | 7/2004 |
| JP | 2005-523012 | 8/2005 |
| JP | 2005-525085 | 8/2005 |
| JP | 2005-527211 | 9/2005 |
| JP | 2009-511081 | 3/2009 |
| JP | 2011-528567 A | 11/2011 |
| JP | 2016-510996 A | 4/2016 |
| WO | WO-94/04686 | 3/1994 |
| WO | WO-94/19465 | 9/1994 |
| WO | WO-95/14078 | 5/1995 |
| WO | WO-98/10058 | 3/1998 |
| WO | WO-98/52614 | 11/1998 |
| WO | WO-99/16884 | 4/1999 |
| WO | WO-99/45962 | 9/1999 |
| WO | WO-99/53023 | 10/1999 |
| WO | WO-99/53028 | 10/1999 |
| WO | WO-00/09669 | 2/2000 |
| WO | WO-00/61617 | 10/2000 |
| WO | WO-00/62067 | 10/2000 |
| WO | WO-01/34824 | 5/2001 |
| WO | WO-01/38548 | 5/2001 |
| WO | WO-02/057436 | 7/2002 |
| WO | WO-02/074968 | 9/2002 |
| WO | WO-03/033701 | 4/2003 |
| WO | WO-03/038057 | 5/2003 |
| WO | WO-03/039462 | 5/2003 |
| WO | WO-03/089580 | 10/2003 |
| WO | WO-03/089630 | 10/2003 |
| WO | WO-03/094849 | 11/2003 |
| WO | WO-03/097675 | 11/2003 |
| WO | WO-2004/035535 | 4/2004 |
| WO | WO-2004/050885 | 6/2004 |
| WO | WO-2004/084805 | 10/2004 |
| WO | WO-2005/014785 | 2/2005 |
| WO | WO-2005/084158 | 9/2005 |
| WO | WO-2006/032876 | 3/2006 |
| WO | WO-2006/116512 | 11/2006 |
| WO | WO-2007/047583 | 4/2007 |
| WO | WO-2007/067183 | 6/2007 |
| WO | WO-2008/112922 | 9/2008 |
| WO | WO-2009/059304 | 5/2009 |
| WO | WO-2009/139930 A2 | 11/2009 |
| WO | WO-2010/011644 | 1/2010 |
| WO | WO-2010/025421 | 3/2010 |
| WO | WO-2012/055170 | 5/2012 |
| WO | WO-2014/164606 | 10/2014 |

OTHER PUBLICATIONS

Final Office Action on U.S. Appl. No. 15/244,138 dated Jun. 4, 2018.
Non-Final Office Action on U.S. Appl. No. 15/785,000 dated Jun. 1, 2018.
Notice of Allowance on U.S. Appl. No. 15/179,735 dated May 29, 2018.
Office Action issued on Chinese Application 201510760532X, dated May 11, 2018.
Coeytaux et al., "The Cationic Amphipathic alpha-Helix of HIV-1 Viral Protein R (Vpr) Binds to Nucleic Acids, Permeabilizes Membranes, and Efficiently Transfects Cells," The Journal of Biological Chemistry, vol. 278, No. 20, May 16, 2003, pp. 18110-18116.
Final Office Action on U.S. Appl. No. 14/873,296, dated Jan. 24, 2018.
Non-Final Office Action on U.S. Appl. No. 15/244,138 dated Jan. 22, 2018.
Aubry et al., "N-Myc Shares Cellular Functions with c-Myc", DNA and Cell Biology, vol. 19, No. 6, Jun. 2000, pp. 353-364.
Baum, Christopher, "Insertional Mutagenesis in Gene Therapy and Stem Cell Biology", Current Opinion in Hematology, vol. 14, Jul. 2007, pp. 337-342.
Beerens et al., "Protein Transduction Domains and their Utility in Gene Therapy", Current Gene Therapy, vol. 3, No. 5, 2003, pp. 486-494.
Benassayag et al., "Human c-Myc Isoforms Differentially Regulate Cell Growth and Apoptosis in *Drosophila melanogaster*," Molecular and Cellular Biology 25(22): 9897-9909 (2005).
Berkson et al., "Pilot Screening Programme for Small Molecule Activators of p53", International Journal of Cancer, vol. 115, 2005, pp. 701-710.
Bird et al., Expansion of Human and Murine Hematopoietic Stem and Progenitor Cells Ex Vivo without Genetic Modification Using MYC and Bcl-2 Fusion Proteins, Plos One, vol. 9, No. 8, Aug. 29, 2014 p. 20 pages.
Bissonnette et al., "Apoptotic cell death induced by c-myc is inhibited by bcl-2," Nature, vol. 359, Oct. 8, 1992, pp. 552-554.
Bouchard et al., "Control of cell proliferation by Myc", Trends in Cell Biology, vol. 8, pp. 202-206, (1998).
Bunting et al., "Restoration of lymphocyte function in Janus kinase 3-deficient mice by retro-viral-mediated gene transfer," Nature Medicine 4:58-64 (1998).
Buske et al., "Deregulated Expression of HOXB4 Enhances the Primitive Growth Activity of Human Hematopoietic Cells", Blood, vol. 100, No. 3, Aug. 1, 2002, pp. 862-868.
Capecchi, Mario R., "Altering the Genome by Homologous Recombination", Science, vol. 244, No. 4910, Jun. 16, 1989, pp. 1288-1292.
Caron, et al., "Endosome disruption enhances the functional nuclear delivery of Tat-fusion proteins", Biochem Biophys Res Commun, (2004), vol. 319, pp. 12-20.
Carotta et al., "Directed Differentiation and Mass Cultivation of Pure Erythorid Progenitors from Mouse Embryonic Stem Cells", Blood, vol. 104, No. 6, Sep. 15, 2004, pp. 1873-1880.
Chadwick, et al., "Notch Signaling Induces Apoptosis in Primary Human CD34 Hematopoietic Progenitor Cells", Stem Cells, (2007), vol. 24, pp. 203-210.
Chen et al., "Small-Molecule Anthracene-Induced Cytotoxicity and Induction of Apoptosis through Generation of Reactive Oxygen Species", Biological & Pharmaceutical Bulletin, vol. 27, No. 6, Jun. 2004, pp. 838-845.
Cheng et al., "BCL-2, BCL-XL, Sequester BH3 Domain-Only Molecules Preventing BAX- and BAK-Mediated Mitochondrial Apoptosis", Molecular Cell (2001) vol. 8, pp. 705-711.
Chin et al., "Essential Role for Oncogenic Ras in Tumour Maintenance", Nature, vol. 400, 1999, pp. 468-472.
Chinese 3rd Office Action dated Nov. 28, 2016 in Chinese Patent Application No. 201410168106.2.

(56) References Cited

OTHER PUBLICATIONS

Choi et al., "Myc Protein is Stabilized by Suppression of a Novel E3 Ligase Complex in Cancer Cells", Genes & Development, vol. 24, 2010, pp. 1236-1241.
Choi, et al., "Status Epilepticus-Induced Somatostatinergic Hilar Interneuron Degeneration Is Regulated by Striatal Enriched Protein Tyrosine Phosphatase", Journal of Neuroscience, (2007), vol. 27, No. 11, pp. 2999-3009.
Coller, et al., "Expression Analysis with Oligonucleotide Microarrays Reveals that MYC Regulates Genes Involved in Growth, Cell Cycle, Signaling, and Adhesion", PNAS, (2000), 97(7):3260-3265.
Communication issued on EP Application 09747016.5, dated Jun. 12, 2017.
Conti, et al., "Gene therapy using neural stem cells," Methods Mol. Biol. 198:233-244 (2002).
Coppola et al., "Constitutive c-myc oncogene expression blocks mouse erythroleukaemia cell differentiation but not commitment," Nature, vol. 320, Apr. 24, 1986, pp. 760-763.
D'Alessandro et al, "Red blood cell storage: the story so far," Blood Transfus, Mar. 29, 2010, pp. 82-88.
Dang et al., "Identification of the Human c-myc Protein Nuclear Translocation Signal", Molecular and Cellular Biology, vol. 8, No. 10, Oct. 1988, pp. 4048-4054.
Dang et al., "Nuclear and Nucleolar Targeting Sequences of c-erb-A, c-myb, N-myc, p53, HSP70 and HIV tat Proteins". Journal of Biological Chemistry, vol. 264, No. 30, pp. 18019-18023 (1989).
Dang, Chi V., "c-Myc Target Genes Involved in Cell Growth, Apoptosis, and Metabolism", Molecular and Cellular Biology, vol. 19, No. 1, Jan. 1999, pp. 1-11.
Daugas et al, "Erythrocytes: Death of a Mummy, "Cell Death and Differentiation, vol. 8, 2001, pp. 1131-1133.
Decision of Rejection issued on Japanese application 2014-108137, dated Jun. 2, 2016, English translation only.
Delgado et al., "Myc Roles in Hematopoiesis and Leukemia," Genes and Cancer, 2010, pp. 605-616.
Deocampo, et al., "Cooperation of BCL-2 and MYC in the Neoplastic Transformation of Normal Rat Lever Epithelial Cells is Related to the Down-Regulation of Gap Junction-Mediated Intercellular Communication", Carcinogenesis, vol. 21, No. 8, pp. 1501-1506,(2000).
Dmitrovsky et al., "A Transfected c-myc Oncogene Inhibits Mouse Erytholeukemic Differentiation," Current Topics in Microbiology and Immunology, vol. 132, 1986, 4 pages.
Domashenko et al., "TAT-mediated transduction of NF-Ya peptide induces the ex vivo proliferation and egraftment potential of human hematopoietic progenitor cells," Blood, Oct. 14, 2010, vol. 116, No. 15, pp. 2676-2683.
Dvorak et al., "Cytochemical Localization of Peroxidase Activity in the Developing Erythrocyte," Am. J. Pathol. 1972, 67(2), pp. 303-326.
Eilers, et al., "Chimeras of MYC Oncoprotein and Steroid Receptors Cause Hormone-Dependent Transformation of Cells," Nature 340(6228):66-68 (1989).
Eischen, et al., "Apoptosis Triggered by Myc-Induced Suppression of Bcl-XL or Bcl-2 Is Bypassed during Lymphomagenesis", Molecular Cell Biology, 2001, 21: 5063-5070.
English Translation of Decision of Rejection on Japanese Application No. 2011-520133, dated Nov. 26, 2014, 6 pages.
English Translation of Decision of Rejection on Japanese Application No. 2011-525258, dated Dec. 3, 2014, 11 pages.
English Translation of Fourth Office Action received for Chinese Patent Application No. 200880015602.7 dated Nov. 11, 2013, 6 pages.
English Translation of Notification of Defects in Israeli Patent Application No. 190946 dated May 14, 2015, 2 pages.
English Translation of Notification of Reasons of Refusal for Japanese Patent Application No. 2012-221023 dated Jun. 24, 2014, 2 pages.
English Translation of Office Action on Chinese Appln. No. 200980127166.7 dated Apr. 11, 2014, 3 pages.
English Translation of Office Action on Israeli Application No. 208810 dated Jan. 13, 2015, 3 pages.
English Translation of Office Action on Israeli Application No. 232432 dated Mar. 8, 2015, 3 pages.
English Translation of Office Action on Israeli Patent Application No. 200919 dated May 19, 2014, 3 pages.
English Translation of Office Action on Japanese Patent Application. No. 2012-221023 dated Apr. 22, 2014, 3 pages.
English Translation of Office Action on Korean Patent Application No. 10-2013-7020078 dated Sep. 17, 2014, 5 pages.
English Translation of Office Action received for Chinese Patent Application No. 200980126312.4 dated Jan. 22, 2014, 3 pages.
English Translation of Office Action received for Eurasian Patent Application No. 201001762/28, posted Oct. 16, 2013, 1 page.
English translation of Office Action received for Israeli Patent Application No. 190946, dated Apr. 22, 2013, 1 page.
English Translation of Office Action received for Israeli Patent Application No. 209968 dated Jan. 2, 2014, 2 pages.
English translation of Office Action received for Japanese Application No. 2008-536713 dated Aug. 5, 2013, 2 pages.
English Translation of Office Action received for Japanese Patent Application No. 2011-525258 dated Feb. 17, 2014, 4 pages.
English Translation of Office Action received for Korean Patent Application No. 10-2008-7011791 dated Jan. 15, 2014, 3 pages.
English Translation of Office Action received for Korean Patent Application No. 10-2013-7028338, dated Jan. 15, 2014, 3 pages.
English Translation of Second Office Action received for Chinese Patent Application No. 200980127166.7, dated Jun. 10, 2013, 1 page.
English Translation of the Third Office Action on Chinese Patent Application No. 200680045545.8 dated Feb. 15, 2015, 4 pages.
English Translation of Third Office Action on Japanese Patent Application No. 2009-553785 dated Apr. 22, 2014, 3 pages.
Esdar, C., et al., "Differentiation-associated apoptosis of neural stem cells is effected by Bcl-2 overexpression: impact on cell lineage determination," Eur. J. Cell Biol.,(2001), vol. 80, No. 8, pp. 539-553.
Exam Report issued on European Application 14779483.8, dated Oct. 16, 2017.
Examination Report for Indian Patent Application No. 3332/DELNP/2008 dated Aug. 23, 2013, 6 pages.
Examination Report issued on Australian Application 2013292330, dated Sep. 6, 2017.
Examination Report issued on Australian Application 2015205879, dated Mar. 15, 2016.
Examination Report issued on Australian Application 2016203892, dated Apr. 12, 2017.
Examination Report issued on EP Application 09747016.5, dated Jul. 26, 2016.
Examination Report issued on EP Application 15175802.6, dated Jan. 31, 2017.
Examination Report issued on Indian Application 2048/DELNP/2011, dated Sep. 15, 2016.
Examination Report issued on Indian Application 634/DELNP/2011, dated Jun. 8, 2017.
Examination Report issued on Indian Application 9033/DELNP/2010, dated May 19, 2017.
Examination Report No. 1 on Australian Application No. 2014202016 dated May 12, 2015, 3 pages.
Examination Report on Australian application 2009274172, dated Jul. 24, 2014, 3 pages.
Examination Report on Australian Patent Application No. 2012216462 dated Mar. 6, 2014, 3 pages.
Examination Report on Canadian Application 2,731,767, dated Sep. 5, 2014, 2 pages.
Examination Report on Canadian Application No. 2,735,522 dated Oct. 2, 2014, 2 pages.
Examination Report on European Application No. 09747016.5 dated Mar. 19, 2015, 5 pages.
Examiner's Report on Canadian Application No. 2680613 dated Nov. 28, 2014, 4 pages.
Examiner's Report on Canadian Application No. 2723114 dated Apr. 21, 2015, 4 pages.

(56) References Cited

OTHER PUBLICATIONS

Extended European Search Report and Search Opinion received for Patent Application No. 12187097.6, dated Mar. 27, 2013, 8 pages.
Extended European Search Report for EP Patent Application No. 13188850.0, dated May 27, 2014, 8 pages.
Extended European Search Report received for European Patent Application No. 09810692.5, dated Jul. 11, 2011, 5 pages.
Extended European Search Report received for European Patent Application No. 06826025.6, dated Aug. 13, 2009, 8 pages.
Extended European Search Report received for European Patent Application No. 09747016.5, dated May 30, 2012, 8 pages.
Extended European Search Report received for European Patent Application No. 09800871. 7, dated Jun. 24, 2011, 5 pages.
Extended European Search Report received for European Patent Application No. 12187077.8, dated Mar. 25, 2013, 7 pages.
Extended Search Report issued on EP Application 13820331.0, dated Nov. 10, 2016.
Extended Search Report issued on European Application 14778538. 0, dated Sep. 29, 2016.
Extended Search Report issued on European Application 14779483. 8, dated Dec. 23, 2016.
Extended Search Report issued on European Patent Application 15175802.6, dated Dec. 14, 2015.
Fanidi et al., "Cooperative interaction between c-myc and bcl-2 proto-oncogenes," Nature, vol. 359, Oct. 8, 1992, pp. 554-556.
Felsher, et al., "Reversible Tumorigenesis by MYC in Hematopoietic Lineages", (1999), Molecular Cell, 4: 199-207.
Final Office Action on U.S. Appl. No. 12/467,957, dated Sep. 17, 2014, 9 pages.
Final Office Action on U.S. Appl. No. 12/506,894 dated Oct. 9, 2014, 15 pages.
Final Office Action on U.S. Appl. No. 13/797,648 dated Feb. 8, 2017.
Final Office Action on U.S. Appl. No. 14/461,105 dated Sep. 15, 2016.
Final Office Action on U.S. Appl. No. 14/509,870 dated Feb. 3, 2017.
Final Office Action on U.S. Appl. No. 12/701,383 dated Nov. 13, 2014, 18 pages.
Final Office Action on U.S. Appl. No. 13/795,659 dated Jul. 11, 2014, 16 pages.
Final Office Action on U.S. Appl. No. 13/795,659 dated Mar. 26, 2015, 18 pages.
Final Office Action on U.S. Appl. No. 13/797,648 dated Apr. 1, 2015, 12 pages.
Final Office Action on U.S. Appl. No. 11/583,970 dated Apr. 9, 2014, 20 pages.
Final Office Action received for Korean Patent Application No. 10-2009-7021320, dated May 29, 2013, 6 pages (3 pages of English Translation and 3 pages of Office Action).
Final Office Action received for U.S. Appl. No. 11/583,970, dated Nov. 17, 2011, 15 pages.
Final Office Action received for U.S. Appl. No. 12/701,383 , dated Nov. 16, 2011, 13 pages.
Final Office Action received for U.S. Appl. No. 11/583,970, dated Nov. 26, 2008, 13 pages.
Final Office Action received for U.S. Appl. No. 12/048,148, dated Feb. 15, 2013, 17 pages.
Final Office Action received for U.S. Appl. No. 12/467,957 dated Feb. 28, 2011, 8 pages.
Final Office Action received for U.S. Appl. No. 12/550,166, dated May 11, 2012, 12 pages.
Final Office Action received on U.S. Appl. No. 11/583,970, dated Nov. 4, 2009, 10 pages.
Final Office Action Response filed for U.S. Appl. No. 11/583,970, dated Feb. 4, 2010, 10 pages.
Final Office Action Response filed for U.S. Appl. No. 11/583,970, dated Feb. 16, 2012, 14 pages.
Final Office Action Response filed for U.S. Appl. No. 11/583,970, dated Jan. 28, 2009, 15 pages.
Final Office Action Response filed for U.S. Appl. No. 12/701,383 dated Feb. 15, 2012, 13 pages.
First Office Action issued on Chinese Application 201410479685.2, dated Nov. 17, 2015.
Futaki,Chemistry and Biology (Kagaku to Seibutsu), vol. 43, No. 10, Oct. 1, 2005, p. 649-653 (English translation not available).
Gandarillas et al., "C-Myc promotes differentiation of human epidermal stem cells," Genes & Develoopment, vol. 11, 1997, pp. 2869-2882.
Gauss et al., "DEAE-Dextran Enhances Electroportation of Mammalian Cells", Nucleic Acids Research, vol. 20, No. 4, pp. 6739-6740 (1992).
Grumont et al., "The Mitogen-Induced Increase in T Cell Size Involves PKC and NFAT Activation of Rel/NF-kB-Dependent c-myc Expression," Immunity, 2004, vol. 21, p. 19-30.
Guzman et al., "Preferential induction of apoptosis for primary human leukemic stem cells," PNAS 99(25):16220-16225 (2002).
Habib et al., "Myc Stimulates B Lymphocyte Differentiation and Amplifies Calcium Signaling", J.Cell Biol., vol. 179, No. 4, 2007, pp. 717-731.
Hann et al., "Proteins Encoded by the Human C-Myc Oncogene: Differential Expression in Neoplastic Cells", Mol. Cell. Biol., vol. 4, No. 11, Nov. 1984, pp. 2486-2497.
Hiramatsu et al., "Complete Reconstitution of Human Lymphocytes from Cord Blood CD34 Cells Using the Nod/Scid/ycnull Mice Model", Blood, vol. 102, No. 3, 2003, pp. 873-880.
Ho, et al., "Synthetic Protein Transduction Domains: Enhanced Transduction Potential in Vitro and in Vivo", Cancer Research, (2001), vol. 61, pp. 474-477.
Hoffman, "Progress in the develoment of systems for in vitro expansion of human hematopoietic stem cells," Curr. Op. Hematology 6(3): 14 pages (1999).
Horton, S.J. et al., "Continuous MLL-ENL expression is necessary to establish a "Hox Code" and maintain immortalization of hematopoietic progenitor cells," Cancer Res. 65(20):9245-9252 (2005).
Hoshimaru, M. et al., "Differentiation of the immortalized adult neuronal progenitor cell line HC2S2 into neurons by regulatable suppression of the V-MYC oncogene," Proceedings of the National Acadamy of Sciences of USA 93(4):1518-1523 (1996).
Howard, M.J. et al., "Transplantation of apoptosis-resistant embryonic stem cells into the injured rat spinal cord," Somatosensory & Motor Research 22(1-2):37-44 (2005).
Huang et al., "Dynamic Regulation of C-Myc Proto-Oncogene Expression during Lymphocyte Development Revealed by a GFP-c-Myc Knock-In Mouse", Eur. J. Immunol., vol. 38, No. 2, 2008, pp. 342-349.
Huettner et al., "Reversibility of Acute B-Cell Leukaemia Induced by BCR-ABL 1," Nature Genetics, vol. 24, 2000, pp. 57-60.
International Preliminary Report and Written Opinion for International Application No. PCT/US2014/022971, dated Sep. 24, 2015.
International Preliminary Report on Patentability for International Application No. PCT/US2013/051384, dated Jan. 29, 2015, 12 pages.
International Preliminary Report on Patentability issued on PCT/US2014/022977, dated Sep. 15, 2015.
International Preliminary Report on Patentability received for PCT Patent Application No. PCT/US2006/040379, dated Apr. 23, 2008, 5 pages.
International Preliminary Report on Patentability received for PCT Patent Application No. PCT/US2008/056896, dated Sep. 15, 2009, 4 pages.
International Preliminary Report on Patentability received for PCT Patent Application No. PCT/US2008/082263, dated May 4, 2010, 6 pages.
International Preliminary Report on Patentability Received for PCT Patent Application No. PCT/US2009/003105, dated Nov. 17, 2010, 6 pages.
International Preliminary Report on Patentability received for PCT Patent Application No. PCT/US2009/051242, dated Jan. 25, 2011, 6 pages.

(56) References Cited

OTHER PUBLICATIONS

International Preliminary Report on Patentability received for PCT Patent Application No. PCT/US2009/055443, dated Mar. 1, 2011, 6 pages.
International Search Report and Written Opinion for International (PCT) Patent Application No. PCT/US06/040379, dated Sep. 24, 2007, 6 pages.
International Search Report and Written Opinion for International Application No. PCT/US2013/051384, dated Nov. 13, 2013, 15 pages.
International Search Report and Written Opinion for International Application No. PCT/US2014/022971 dated Aug. 13, 2014, 12 pages.
International Search Report and Written Opinion on PCT/US2014/022977, dated Aug. 28, 2014, 13 pages.
International Search Report and Written Opinion received for PCT Patent Application No. PCT/US2008/056896 dated Aug. 14, 2008, 5 pages.
International Search Report and Written Opinion received for PCT Patent Application No. PCT/US2008/082263, dated Jun. 25, 2009, 8 pages.
International Search Report and Written Opinion received for PCT Patent Application No. PCT/US2009/003105, dated Jan. 15,2010, 9 pages.
International Search Report and Written Opinion received for PCT Patent Application No. PCT/US2009/051242, dated Feb. 19, 2010, 9 pages.
International Search Report and Written Opinion received for PCT Patent Application No. PCT/US2009/055443, dated Jun. 30, 2010, 11 pages.
Invitation to Pay Additional Fees and, Where Applicable, Protest Fee for PCT Application No. PCT/US2014/22971, dated May 27, 2014, 2 pages.
Iritani, et al., "c-Myc enhances protein synthesis and cell size during B lymphocyte development", PNAS, (1999), vol. 96, No. 23, pp. 13180-13185.
Jadlowsky, et al., "Dominant negative mutant Cyclin T1 proteins inhibit HIV transcription by specifically degrading Tat", Retrovirology, (2008), vol. 5, Article 63, 12 pages.
Jayapal et al., "Down-regulation of Myc is Essential for Terminal Erythroid Maturation" The Journal of Biological Chemistry, vol. 285, No. 51, pp. 40252-40265, Dec. 17, 2010.
Johnson, N.A. et al., "Lymphomas with concurrent BCL2 and MYC translocations: the critical factors associated with survival", Blood, 2009, vol. 114, No. 11, pp. 2273-2279.
Ju, et al., "Anti-Apoptotic Therapy with a Tat Fusion Protein Protects Against Excitotoxic Insults in Vitro and in Vivo", Experimental Neurology, vol. 210, 2008, pp. 602-607.
Karon et al., "Temporal sequence of major biochemical events during Blood Bank storage of packed red blood cells," Blood Transfus, vol. 10, 2012, pp. 453-461.
Kashio, et al., "A Protein Derived From the Fusion of TAT Peptide and FNK, a Bcl-xL Derivative, Prevents Cochlear Hair Cell Death From Aminoglycoside Ototoxicity In Vivo", Journal of Neuroscience Research, (2007), vol. 85, No. 7, pp. 1403-1412.
Kelso et al., "Survival of the Myeloid Progenitor Cell Line FDC-P1 is Prolonged by Interferon-y or Interleukin-4", Growth Factors, vol. 6, No. 3, 1992, pp. 233-242.
Kitada, et al., "Reversal of Chemoresistance of Lymphoma Cells by Antisense-Mediated Reduction of bcl-2 Gene Expression", Antisense Research and Development, (1994), vol. 4, pp. 71-79.
Korbling et al., "Allogenic Blood Stem Cell Transplantation: Peripheralization and Yield of Donor-Derived Primitive Hematopoietic Progenitor Cells (CD34+Thy-Idim) and Lymphoid Subsets, and Possible Predictors of Engraftment and Graft-Versus-Host Disease," Blood 86:2842-2848 (1995).
Krosl et al., "In vitro expansion of hematopoietic stem cells by recombinant TAT- HOXB4 protein," Nature Mediciine 9(11):1428-1432 (2003).

Lang et al.,j "Mechanisms and Significance of Eryptosis, the Suicidal Death of Erythorocytes," Blood Purification, Vole 33, 2012, pp. 125-130.
Levesque, J-P et al., "The endosteal 'osteoblastic' niche and its role in hematopoietic stem cell homing and mobilization", Leukemia, 2010, vol. 24, pp. 1979-1992.
Li et al., "Reconstitution of Functional Human B Lymphocytes in NOD/SCID Mice Engrafted with ex vivo Expanded CD34 Cord Blood Cells", Experimental Hematology, vol. 30, 2002, pp. 1036-1043.
Littlewood, et. al., "A modified oestrogen receptor ligand-binding domain as an improved switch for the regulation of heterologous proteins", Nucleic Acids Research, (1995), vol. 23, No. 10, pp. 1686-1690.
Macpherson, P. et al., "Activity-dependent gene regulation in conditionally- immortalized muscle precursor cell lines," J. Cell. Biol. 91(4):821-839 (2004).
McCarthy, "Underground movement", Nature Reviews Cancer, (2007), vol. 7, 1 page, published online Oct. 11, 2007.
Melkonyan et al., "Electroporation efficiency in mammalian cells is increased by dimethyl sulfoxide (DMSO)," Nucleic Acids Research 24:4356-4357 (1996).
Merino et al., "Developmental Regulation of the Bcl-2 Protein and Susceptibility to Cell Death in B Lymphocytes", The EMBO Journal, vol. 13, No. 3, 1994, pp. 683-691.
Miharada et al., "Efficient enucleation of erythroblasts differentiated in vitro from hematopoietic stem and progenitor cells", Nature Biotechnology, 24(10): 1255-1256, 2006.
Miller et al., "Expansion in vitro of adult murine hematopoietic stem cells with transplantable lympho-myeloid reconsituting ability," PNAS USA 94: 13648-13653 (1997).
Moore et al., "In Vitro Maintenance of Highly Purified, Transplantable hematopoietic Stem Cells," Blood 89(12):4337-4347 (1997).
Mooslehner et al., Retroviral Integration Sites in Transgenic Mov Mice Frequently Map in the Vicinity of Transcribed DNA Regions,: J. Virology 64:3056- 3058 (1990).
Muchmore et al., "X Ray and NMR Structure of Human Bcl-xL, an Inhibitor of Programmed Cell Death", Nature, vol. 381, May 23, 1996, pp. 335-341.
Non Final Office Action received for U.S. Appl. No. 11/583,970, dated May 9, 2011, 10 pages.
Non Final Office Action received for U.S. Appl. No. 12/048,148, dated Oct. 13, 2011, 9 pages.
Non Final Office Action received for U.S. Appl. No. 12/962,197, dated Aug. 26, 2011, 11 pages.
Non-Final Office Action on U.S. Appl. No. 14/461,105 dated Mar. 22, 2016.
Non-Final Office Action on U.S. Appl. No. 14/415,325 dated Dec. 23, 2016.
Non-Final Office Action on U.S. Appl. No. 14/509,870 dated Jul. 12, 2016.
Non-Final Office Action on U.S. Appl. No. 14/661,786, dated Aug. 27, 2015.
Non-Final Office Action on U.S. Appl. No. 14/873,296 dated Aug. 17, 2017.
Non-Final Office Action on U.S. Appl. No. 12/506,894 dated Apr. 3, 2015, 16 pages.
Non-Final Office Action on U.S. Appl. No. 13/795,659 dated Nov. 26, 2014, 13 pages.
Non-Final Office Action on U.S. Appl. No. 13/797,648 dated Jun. 17, 2016.
Non-Final Office Action on U.S. Appl. No. 11/583,970 dated Sep. 20, 2013, 19 pages.
Non-final Office Action on U.S. Appl. No. 12/467,957 dated Apr. 4, 2014, 14 pages.
Non-Final Office Action on U.S. Appl. No. 12/701383 dated Jun. 13, 2014, 26 pages.
Non-final Office Action on U.S. Appl. No. 13/795,659 dated Mar. 10, 2014, 11 pages.
Non-final Office Action on U.S. Appl. No. 13/797,648 dated Apr. 3, 2014, 13 pages.
Non-Final Office Action received for U.S. Appl. No. 11/583,970, dated Mar. 12, 2008, 13 pages.

(56) References Cited

OTHER PUBLICATIONS

Non-Final Office Action received for U.S. Appl. No. 12/467,957 dated Oct. 13, 2010, 15 pages.
Non-Final Office Action received for U.S. Appl. No. 12/701,383, dated Apr. 28, 2011, 9 pages.
Non-Final Office Action received for U.S. Appl. No. 11/583,970, dated Mar. 23, 2009, 11 pages.
Non-Final Office Action received for U.S. Appl. No. 12/048,148 dated Jan. 19, 2011, 6 pages.
Non-Final Office Action received for U.S. Appl. No. 12/048,148, dated May 11, 2012, 9 pages.
Non-Final Office Action received for U.S. Appl. No. 12/506,894, dated Apr. 27, 2012, 13 pages.
Non-Final Office Action received for U.S. Appl. No. 12/550,166 dated Jan. 11, 2012, 7 pages.
Non-Final Office Action Response filed for U.S. Appl. No. 11/583,970 dated Aug. 25, 2011, 22 pages.
Non-Final Office Action Response filed for U.S. Appl. No. 11/583,970 dated Jun. 24, 2009, 11 pages.
Non-Final Office Action Response filed for U.S. Appl. No. 11/583,970, dated Aug. 12, 2008, 12 pages.
Non-Final Office Action Response filed for U.S. Appl. No. 12/701,383 dated Aug. 25, 2011, 20 pages.
Notice of Acceptance issued on Australian Application 2009274172, dated Aug. 3, 2015.
Notice of Acceptance of Australian Application No. 2009246876 dated Apr. 2, 2015, 3 pages.
Notice of Acceptance of Australian Application No. 2012216462, dated Apr. 10, 2015, 2 pages.
Notice of Allowance on U.S. Appl. No. 11/583,970, dated Aug. 29, 2014, 11 pages.
Notice of Allowance on U.S. Appl. No. 12/467,957, dated Nov. 26, 2014, 7 pages.
Notice of Allowance on U.S. Appl. No. 13/795,659 dated Mar. 1, 2016.
Notice of Allowance on U.S. Appl. No. 13/795,659, dated Sep. 29, 2015.
Notice of Allowance on U.S. Appl. No. 14/415,325 dated Jun. 9, 2017.
Notice of Allowance on U.S. Appl. No. 14/461,105 dated Jun. 2, 2017.
Notice of Allowance on U.S. Appl. No. 14/509,870 dated Jun. 22, 2017.
Notice of Allowance on U.S. Appl. No. 14/661,786 dated Apr. 25, 2016.
Notice of Allowance on U.S. Appl. No. 12/506,894 dated Jun. 16, 2015, 8 pages.
Notice of Allowance on U.S. Appl. No. 12/701,383 dated May 22, 2015, 9 pages.
Notice of Allowance on U.S. Appl. No. 13/777,967 dated Jul. 14, 2014.
Notice of Allowance on U.S. Appl. No. 12/550,166 dated Apr. 28, 2014, 4 pages.
Notice of Allowance received for U.S. Appl. No. 12/550,166, dated Nov. 26, 2012, 9 pages.
Notice of Reasons for Rejection (English translation) issued on Japanese application 2014-108137, dated Aug. 18, 2015.
Notice of Reasons for Rejection issued on Japanese Application 2014-108137, dated Nov. 1, 2017.
Notice of Reasons for Rejection issued on Japanese Application 2015-075703, dated Dec. 8, 2016, English translation only.
Notice of Reasons for Rejection issued on Japanese application 2015-523297, dated Jul. 19, 2017, English Translation only.
Notice of Reasons for Rejection issued on Japanese Application 2016-027812, dated Mar. 1, 2017.
Notice of Reasons for Rejection issued on Japanese Application 2016-501113, dated Dec. 28, 2017.
Notice of Reasons for Rejection issued on Japanese Application 2016-501117, dated Apr. 17, 2017.
Notice of Reasons for Rejection issued on Japanese Application 2015-075703, dated May 11, 2016, English translation.
Notification of Defects issued on Israeli Appl 2053539, dated Jun. 26, 2016.
Notification of Defects issued on Israeli Application 208810, dated Sep. 18, 2017.
Office Action issued Korean Application 10-2010-7028384, dated Apr. 28, 2017, English Translation.
Office Action issued on Australian Application 2014249202, dated Nov. 18, 2015.
Office Action issued on Canadian Appl. 2626525, dated Jun. 6, 2016.
Office Action issued on Canadian Application 2,626,525 dated Jun. 13, 2017.
Office Action issued on Canadian Application 2723114, dated Jul. 7, 2016.
Office Action issued on Canadian Application 2731767, dated Oct. 5, 2015.
Office Action issued on Canadian Application 2735522, dated Nov. 16, 2015.
Office Action issued on Chinese Application 201410168106.2, dated Jun. 22, 2017 English translation only.
Office Action issued on Chinese Application 201410479865.2, dated Jul. 5, 2016, English Translation only.
Office Action issued on Chinese Application 201480026147.6, dated Apr. 20, 2017, English translation.
Office Action issued on Chinese Application 201480026147.6, dated Sep. 28, 2017.
Office Action issued on Japanese application 2015-523297, dated Apr. 3, 2017.
Office Action issued on Japanese Application 2016-501117, dated Nov. 15, 2017.
Office Action issued on Korean Appl. 10-2010-7028384, dated Aug. 18, 2016 English translation only.
Office Action on Canadian Application No. 2,626,525 dated Apr. 8, 2014, 4 pages.
Office Action on Canadian Application No. 2626525 dated May 8, 2015, 3 pages.
Office Action on Canadian Patent Application No. 2,680,613 dated Nov. 21, 2013, 3 pages.
Office Action received for Australian Patent Application No. 2006304392, dated Jul. 2012, 3 pages.
Office Action received for Australian Patent Application No. 2009246876 dated Jan. 2014, 6 pages.
Office Action received for Australian Patent Application No. 2009285547, dated Jul. 25, 2011, 2 pages.
Office Action received for Canadian Patent Application No. 2626525, dated Apr. 17, 2013, 4 pages.
Office Action received for Canadian Patent Application No. 2731767, dated Jul. 25, 2012, 3 pages.
Office Action received for Canadian Patent Application No. 2735522, dated Sep. 10, 2012, 3 pages.
Office Action received for Chinese Patent Application No. 200580031540.5, dated Jul. 3, 2012, English translation, 11 pages.
Office Action received for Chinese Patent Application No. 200680045545.8, dated Dec. 31, 2010, English translation, 8 pages.
Office Action received for Chinese Patent Application No. 200680045545.8, dated Sep. 15, 2011, English translation, 9 pages.
Office Action received for Chinese Patent Application No. 200880015602.7, dated Jan. 31, 2012, 16 pages (10 pages of English translation and 6 pages of Office Action).
Office Action received for Chinese Patent Application No. 200880015602.7, dated May 9, 2013, 13 pages (8 pages of English Translation and 5 pages of Official copy).
Office Action received for Chinese Patent Application No. 200880015602.7, dated Oct. 31, 2012, 10 pages (6 pages of English Translation and 4 pages of Chinese Office Action).
Office Action received for Chinese Patent Application No. 200980126312.4, dated Aug. 28, 2012, 12 pages (6 pages of English Translation and 6 pages of Office Action).
Office Action received for Chinese Patent Application No. 200980127166.7, dated Dec. 5, 2012, 4 pages (1 page of English Translation and 3 pages of Office Action).

(56) References Cited

OTHER PUBLICATIONS

Office Action received for Chinese Patent Application No. 200980126312.4, dated Jan. 30, 2012, 14 pages (7 pages of English translation and 7 pages of Office Action).
Office Action received for European Application No. 09810692.5 dated Feb. 25, 2014, 3 pages.
Office Action received for European Patent Application No. 06826025.6, dated Sep. 1, 2009, 3 pages.
Office Action received for European Patent Application No. 06826025.6, dated Sep. 22, 2009, 1 page.
Office Action received for European Patent Application No. 08743862.8, dated May 14, 2010, 6 pages.
Office Action received for European Patent Application No. 08743862.8, dated Sep. 23, 2010, 6 pages.
Office Action received for European Patent Application No. 09747016.5, dated Apr. 9, 2013, 6 pages.
Office Action received for European Patent Application No. 09810692.5, dated Mar. 28, 2012, 3 pages.
Office Action received for Indian Application No. 3332/DELNP/2008 dated Aug. 23, 2013, 3 pages.
Office Action received for Israel Patent Application No. 200919, dated Jan. 17, 2013, 4 pages (2 pages of English Translation and 2 pages Of Official Copy).
Office Action received for Israel Patent Application No. 208810, dated Nov. 2, 2011, 3 pages of English Translation only.
Office Action received for Israel Patent Application No. 209343, dated Aug. 14, 2012, 3 pages (2 pages of English Translation and 1 page of Office Action).
Office Action received for Israel Patent Application No. 209343, dated Nov. 2, 2011, 3 pages of English Translation only.
Office Action received for Israel Patent Application No. 209968, dated Aug. 21, 2012, 4 pages (2 pages of English Translation and 2 pages of Office Action).
Office Action received for Israel Patent Application No. 209968, dated Nov. 2, 2011, 3 pages of English Translation only.
Office Action received for Israel Patent Application No. 200919, dated Dec. 5, 2011, 2 pages of English Translation only.
Office Action received for Israeli Patent Application No. 190946, dated Jul. 3, 2012, 1 page, (English Translation only).
Office Action received for Israeli Patent Application No. 208810, dated Jan. 2, 2013, 4 pages (English Translation only).
Office Action received for Japanese Application No. 2011-520133, dated Feb. 5, 2014, 4 pages (in Japanese).
Office Action received for Japanese Patent Application No. 2008-536713, dated Jul. 3, 2012, 2 pages (No English Translation Provided).
Office Action received for Japanese Patent Application No. 2009-553785, dated Jun. 19, 2012, 6 pages (2 pages of English Translation and 4 pages of Office Action).
Office Action received for Korean Patent Application No. 10-2008-7011791, dated May 28, 2013, English translation, 3 pages.
Office Action received for Korean Patent Application No. 10-2009-7021320, dated Jul. 29, 2011, 7 pages (3 pages of English Translation and 4 pages of Office Action).
Office Action received for Korean Patent Application No. 10-2009-7021320, dated Sep. 18, 2012, 11 pages (7 pages of English Translation and 4 pages of Office Action).
Official Action on European Application No. 09810692.5 dated Oct. 22, 2014, 3 pages.
Oral Proceedings Summons received for European Patent Application No. 08743862.8, dated May 14, 2012, 6 pages.
Pan et al., "Reprogramming human fibroblasts using HIV-1 TAT recombinant proteins OCT4, SOX2, KLF4 and c-MYC," Mol. Biol Rep (2010) 37:2117-2124.
Partial Search Report issued on EP Appl. 14778538.0,dated Jul. 8, 2016.
Partial Supplementary European Search Report issued on EP Appl. 13820331.0, dated Jun. 30, 2016.
PCT/US06/40379 Search Report and Written Opinion dated Sep. 24, 2007.
PCT/US08/56896 Written Opinion dated Jul. 18, 2008.
Pharmaceutics (Yakuzaigaku), 64(3), 2004, p. 164-167 (English translation not available).
Pierelli et al., "Modulation of bcl-2 and p27 in human primitive proliferating hematopoietic progenitors by autocrine TGF-B 1 is a cell cycle-independent effect and influences their hematopoietic potential,"Blood 95:3001-3010 (2000).
Pinto et al., "Hematopoietic progenitor/stem cells immortalized by Lhx2 generate functional hematopoietic cells in vivo," Blood 99(11):3939-3946 (2002).
Podsypanina, K. et al., "Oncogene cooperation in tumor maintenance and tumor recurrence in mouse mammary tumors induced by MYC and mutant Kras," PNAS 105(13):5242-5247 (2008).
Polenakovic et al., "Is Erythropoietin a Survival Factor for Red Blood Cells," J. Am. Soc. Nephrol, vol. 7, 1996, pp. 1178-1182.
Pollock, K. et al., "A conditionally immortal clonal stem cell line from human cortical neuroepithelium for the treatment of ischemic stroke," Exp. Neurol., (2006), vol. 199, No. 1, pp. 143-155.
Pre-Appeal Examination Report on Japanese Application 2014-108137, dated Dec. 7, 2016, English translation only.
Prochownik et al., "Deregulated expression of c-myc by murine erythroleukaemia cells prevents differentiation," Nature, vol. 322, Aug. 28, 1986, pp. 848-850.
Qin et al., "Nuclear Factor KB Nuclear Translocation Upregulates c-Myc and p53 Expression during NMDA Receptor- Mediated Apoptosis in Rat Striatum", The Journal of Neuroscience, vol. 19, No. 10, May 15, 1999, pp. 4023-4033.
Rabbitts, et al., "Metabolism of c-myc gene products: c-myc mRNA and protein expression in the cell cycle", EMBO Journal, (1985), vol. 4, No. 8, pp. 2009-2015.
Radhakrishnan et al., "A Novel Transcriptional Inhibitor Induces Apoptosis in Tumor Cells and Exhibits Antiangiogenic Activity", Cancer Research, vol. 66, No. 6, Mar. 15, 2006, pp. 3264-3270.
Raymon, H.K. et al., "Immortalized human dorsal root ganglion cells differentiate into neurons with nociceptive properties," J. Neuroscience 19(13):5420-5428 (1999).
Re-Examination Report on Australian Patent No. 2009285547 dated Apr. 23, 2015, 3 pages.
Refaeli et al., "The protooncogene MYC can break B cell tolerance," PNAS, 102(11):4097-4102, (2005).
Refaeli, Y, "The B-Cell Antigen Receptor and Overexpression of MYC Can Cooperate in the Genesis of B-Cell Lymphomas", PLOS Biology, vol .6, No. 6, e152, 2008, pp. 1208-1225.
Request for ReExamination filed in Chinese Patent Application No. 200680045545.8 dated Oct. 12, 2012, 17 pages (6 pages of English Machine Translation and 11 pages of Chinese-Language Document as filed).
Restriction Requirement received for U.S. Appl. No. 11/583,970, dated Nov. 13, 2007, 14 pages.
Restriction Requirement received for U.S. Appl. No. 12/701,383, dated Jan. 25, 2011, 10 pages.
Richter, et al., "Lhx.2 expression in hematopoietic progenitor/stem cells in vivo causes a chronic myeloproliferative disorder and altered globin expression," J. Hematol., (2003), 88(12):1336-1347.
Roh et al., "Transgenic Mice for Cre-Inducible Overexpression of the Oncogenes c-MYC and Pim-1 in Multiple Tissues", Genesis: The Journal of Genetics and Development, vol. 44 pp. 447-453, (2006).
Rosenwald, et al., "Increased Expression of Eukaryotic Translation Inhibition Factors eIF-4E and eIF-2alpha in Response to Growth Induction by C-MYC", Proc. Natl. Acad. Sci. USA, vol. 90, pp. 6175-6178, (1993).
Rudolph et al., "Expression of Mad1 in T cells leads to reduced thymic cellularity and impaired mitogen-induced proliferation", Oncogene, 2001, vol. 20, pp. 1164-1175.
Satoh et al, "Roles for c-Myc in Self-renewal of Hematopoietic Stem Cells," The Journal of Biological Chemistry, 2004, vol. 279, No. 24, p. 24986-24993.
Sauer, "Inducible Gene Targeting in Mice Using the Cre/lox System," Methods, (1998), vol. 14, No. 4, pp. 381-392.
Schiedlmeier et al., "High-level Ectopic HOXB4 Expression Confers a Profound in Vivo Competitive Growth Advantage on Human

(56) References Cited

OTHER PUBLICATIONS

Cord Blood CD34 Cells, but Impairs Lymphomyeloid Differentiation", Blood, vol. 101, No. 5, Mar. 1, 2003, pp. 1759-1768.
Schmidt et al., "Transgenic Mice Bearing the Human c-myc Gene Activated by an Immunoglobulin Enhancer: A pre-B-cell Lymphoma Model", National Academy of Sciences, vol. 85, pp. 6047-6051 (1988).
Schroy, et al., "A Simple Method for Freezing and Thawing Cultured Cells," Methods in Cell Science (formerly known as TCA Manual), (1976), vol. 2, No. 1, pp. 309-310.
Schwarze et al., "Protein transduction: unrestricted delivery into all cells?" Trends Cell Biol. 10:290-295 (2000).
Seibutsugaku Jiten (Dictionary of Biology), Iwanami Shoten, 1997, The 4th edition, p. 1396, English translation not available.
Silva et al., "Erythropoietin Can Promote Erythroid Progenitor Survival by Repressing Apoptosis Through Bcl-xl, and Bcl-2," Blood, vol. 88, No. 5, Sep. 1, 1996, pp. 1576-1582.
Sipione, S. et al., "Modeling brain pathologies using neural stem cells," Methods Mol. Biol., (2002), vol. 198, pp. 245-262.
Snyder, et al., "Regulation of NMDA receptor trafficking by amyloid-3132", Nature Neuroscience, (2005), vol. 8, No. 8, pp. 1051-1058.
Soane,L., et al., "TAT-mediated endocytotic delivery of the loop deletion Bcl-2 protein protects neurons against cell death", Journal of Neurochemistry, (2005), vol. 95, pp. 230-243.
Sunyer, "Evolutionary and Functional Relationships of B Cells from Fish and Mammals: Insights into their Novel Roles in Phagocytosis and Presentation of Particulate Antigen," Infect Disord Drug Targets 12(3):200-212 (2012).
Supplementary Search Report received for European Patent Application No. 06826025.6, dated Jul. 28, 2009, 7 pages.
Supplementary Search Report received for European Patent Application No. 08743862.8 dated Feb. 9, 2010, 1 page.
Taguchi et al., "Nuclear trafficking of macromolecules by an oligopeptide derived from Vpr of human immunodeficiency virus type-1" Biochem. Biophys. Res. Commun. 2004, 320(1) pp. 18-26.
Takahashi, et al., Induction of pluripotent stem cells from mouse embryonic and adult fibroblast cultures by defined factors, Cell, 126:663-676, 2006.
Theis, et al., "Expression of the myc/His-Tagged Human Peptide Transporter hPEPT1 in Yeast for Protein Purification and Functional Analysis", Protein Expression and Purification, (2001), vol. 22, pp. 436-442.
Thomas, et. al., "Progress and Problems with the Use of Viral Vectors for Gene Therapy", Nature, (May 2003), vol. 4, pp. 346-358.
Trumpp et al., "c-Myc Regulates Mammalian Body Size by Controlling Cell Number But Not Cell Size," Nature 414: 768-773 (2001).
Tsai et al., "Lymphohematopoietic progenitors immortalized by a retroviral vector harboring a dominant-negative retinoic acid receptor can recapitulate lymphoid, myeloid, and erythroid development," Genes & Dev. 8:2831-2841 (1994).
Varnum-Finney et al., "Pluripotent, cytokine-dependent, hematopoietic stem cells are immortalized by constitutive Notch1 signaling," Nature Medicine 6(11):1278-1281 (2000).
Vaux et al., "Bcl-2 gene promotes hemopoietic cell survival and cooperates with c- myc to immortalize pre-B cells," Nature 335:440-442 (1988).
Vaux, et al., "Immunologic competence of B cells subjected to constitutive c-myc oncogene expression in immunoglobulin heavy chain enhancer myc transgenic mice", J. Immunol., (1987), vol. 139, No. 11, pp. 3854-3860.
Wagner et al., "Myc-Mediated Apoptosis is Blocked by Ectopic Expression of Bcl-2," Molecular and Cellular Biology, Apr. 1993, pp. 2432-2440.
Wang et al., "Primitive Human Hematopoietic Cells Are Enriched in Cord Blood Compared with Adult Bone Marrow or Mobilized Peripheral Blood as Measured by the Quantitative in Vivo SCID-Repopulating Cell Assay," Blood 89:3919-3924 (1997).
Wechsler et al., "MXI1, a Putative Tumor Suppressor Gene, Suppresses Growth of Human Glioblastoma Cells", Cancer Research 57, pp. 4405-4912, (1997).
Wikipedia [online], "Stem Cell", 2008, [retrieved on Nov. 13, 2008]. Retrieved from the Internet: <URL: http//en.wikipedia.org/wiki/Stem_cell>, 11 pages.
Wilson, et al., "c-Myc controls the balance between hematopoietic stem cell self-renewal and differentiation", Genes and Development, 2004, vol. 18, pp. 2747-2763.
Wu et al., "Inhibition of c-myc Expression Induces Apoptosis of WEHI 231 Murine B Cells", Molecular and Cellular Biology, Sep. 1996, vol. 16, No. 9, pp. 5015-5025.
Wurm, et al., "Large-scale transient expression of mammalian cells for recombinant protein production," Curr. Op. Biotech., (1999), vol. 10, pp. 156-159.
Xi et al., "In Vitro Large Scale Production of Human Mature Red Blood Cells From Hematopoietic Stem Cells by Coculturing with Human Fetal Liver Stromal Cells," Biomed. Res. Int. Epub Jan. 30, 2013, 2013:807863.
Xu Zhixiang, et al, "The Development of the Study on the Anti-Tumor Effect of Flt3 Ligand," Chinese Journal of Tumor Biological Therapy, vol. 7, No. 3, Sep. 30, 2000.
Yagihashi, et al., "Detection of Anti-Survivin Antibody in Gastrointestinal Cancer Patients", Clinical Chemistry, (2001), vol. 47, No. 9, pp. 1729-1731.
Yanai et al., "A novel stromal cell-dependent hematopoietic cell line established from temperature-sensitive SV40 T-antigen transgenic mice," Exp. Hematol., 27:1087-1096 (1999).
Young et al., "B-Cell Receptor Signaling in the Genesis and Maintenance of B-Cell Lymphoma", Future Oncology, vol. 4, No. 5, 2008, pp. 591-594.
Zhang et al., "Cytokines Regulating Hematopoietic Stem Cell Function", Current Opinion Hematology, vol. 15, No. 4, Jul. 2008, pp. 307-311.
Zhang et al., "Reprogramming of somatic cells via TAT-mediated protein transduction of recombinant factors," Biomaterials 33 (2012) 5047-5055.
Examination Report issued on EP Application 13820331.0, dated Apr. 24, 2018.
Examination Report issued on EP Application 14778538.0, dated Apr. 16, 2018.
Non-Final Office Action on U.S. Appl. No. 13/797,648 dated Apr. 19, 2018, includes Accession NP 002458.2, 2018.
Non-Final Office Action on U.S. Appl. No. 15/179,735 dated Feb. 26, 2018.
Second Office Action issued on Chinese Application 201480026500.0, dated Apr. 27, 2018.
Israeli Office Action, dated Jun. 27, 2018, issued in Israeli Patent Application No. 208810.
Japanese Office Action, issued in Japanese Patent Appln. No. 2017-166334, 6 pages.
Australian Examination Report, issued in Australian Patent Application No. 2014249200, 4 pages (dated Mar. 15, 2019).
De Korte, "New additive solutions for red cells", ISBT Science Series 11: 165-170 (2016).
European Extended Search Report, issued in European Patent Appln. No. 19157513.3, 13 pages (dated Apr. 1, 2019).
Final Office Action on U.S. Appl. No. 15/244,138 dated Mar. 14, 2019.
Maite, et al., "Erythropoietin Can Promote Erythroid Progenitor Survival by Repressing Apoptosis Through Bcl-XL, and Bcl-2", Blood Journal 88(5): 1576-1582 (1996).
Momir, et al., "Is erythropoietin a survival factor for red blood cells", Journal of the American Society of Nephrology, 7(8): 1178-1182 (1996).
Penuela, et al., "Erythropoietin reduces storage lesions and decreases apoptosis indices in blood bank red blood cells", Revista Brasileira de Hematologia e Hemoterapia 38(1): 15-20 (2016).
Japanese Office Action, issued in Japanese Patent Application No. 2018-017287, 13 pages (dated Apr. 18, 2019).
Laurentl, et al., "Hematopoietic Stem Cell Function and Survival Depend on c-Myc and N-Myc Activity", Cell Stem Cell 3: 611-624 (2008).

(56) References Cited

OTHER PUBLICATIONS

Song, "Cloning and expression of PTD-BDNF fusion gene and purification of expressed product", Bioengineering Pharmaceutical Research and Practice, Anhui Science and Technology Press, 1st Ed., pp. 200-201 (Feb. 2009), (Only the abstract considered).
Canadian Office Action, issued in corresponding CA Pat. App. No. 2879667, 4 pages (dated Jun. 18, 2019).
European Office Action, issued in corresponding EP Pat. App. No. 14779483.8, 4 pages (dated Jun. 28, 2019).
Japanese Office Action, issued in JP Pat. App. No. 2018-153567, 8 pages (dated Jul. 25, 2019).
Non-Final Office Action on U.S. Appl. No. 16/042,904 dated Jul. 12, 2019.
Notice of Allowance on U.S. Appl. No. 15/244,138 dated Jun. 5, 2019.
European Office Action, issued in European Pat. App. No. 18154875.1, 4 pages. (dated Sep. 6, 2019).
Final Office Action on U.S. Appl. No. 16/042,904, dated Nov. 1, 2019.
Hirose, et al., "Immortalization of Erythroblasts by c-MYC and BCL-XL Enables Large-Scale Erythrocyte Production from Human Pluripotent Stem Cells", Stell Cell Reports I: 499-508 (2013).
Indian First Examination Report, issued in Indian Pat. App. No. 9205/DELMP/2015, 8 pages. (dated Nov. 28, 2019).
Non-Final Office Action on U.S. Appl. No. 15/643,133 dated Nov. 1, 2019.
Opferman, et al., "Anti-apoptotic BCL-2 family members in development", Cell Death and Differentiation 25: 37-45 (2018).
Australian Examination Report, issued in Australian Pat. App. No. 2018247295, 2 pages (dated Dec. 6, 2019).
Notice of Allowance on U.S. Appl. No. 16/042,904 dated Dec. 11, 2019.

\* cited by examiner

COMPOSITIONS AND METHODS FOR MODULATING AN IMMUNE RESPONSE

CROSS-REFERENCE

This application is a Continuation of U.S. application Ser. No. 14/461,105, filed Aug. 15, 2014, now U.S. Pat. No. 9,775,897, which is a Continuation of U.S. application Ser. No. 13/777,967, filed Feb. 26, 2013, now U.S. Pat. No. 8,828,723, which is a Continuation application of U.S. application Ser. No. 12/550,166, filed Aug. 28, 2009, now U.S. Pat. No. 8,784,825, which claims the benefit of U.S. Provisional Application No. 61/092,708, filed Aug. 28, 2008, all of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 106417-0196SEQLIST.txt, date recorded: Aug. 15, 2014, size: 9.2 KB)

BACKGROUND OF THE INVENTION

There are multiple types of vaccines: vaccines containing dead microorganisms (e.g. the influenza and cholera vaccines); vaccines containing attenuated microorganisms (e.g. the MMR vaccine); vaccines containing toxoids (e.g. the DPT vaccine); vaccines containing subunits of the pathogen (e.g. the HPV vaccine); and nucleic acid (e.g. RNA and DNA) vaccines (e.g. avian flu vaccine, West Nile Virus vaccine, and multiple cancer vaccines). Vaccine adjuvants are agents that stimulate the immune system and increase the response of the immune system to a vaccine.

SUMMARY OF THE INVENTION

There is a need for vaccine adjuvants that enhance an immunological response to an antigen. The inventors have discovered that increasing the expression of MYC or the activity of a MYC peptide enhances immunological responses to antigens. In order to increase MYC concentrations in the nucleus of cells with minimal side-effects, the inventors have designed a fusion peptide that can penetrate the nucleus of cells. This peptide can be administered topically to decrease systemic effects. This peptide also increases the viability of leukocytes, including T-cells, and B-cells. Further, the inventors have designed several assays for identifying other agents that meet this unmet need.

There is also a need for methods of treating autoimmune disorders. The inventors have discovered that decreasing the expression of MYC or the activity of a MYC peptide treats auto-immune disorders. In order to fulfill this unmet need, the inventors have designed several assays for identifying agents that inhibit (partially or fully) the activity of an immune system. In certain instances, the agents that inhibit the immune system decrease the viability of leukocytes or increase the proportion of anergic B-cells.

Disclosed herein, in certain embodiments, is a peptide that up-regulates the expression of a MYC gene, the activity of a Myc polypeptide, or a combination thereof, comprising: (a) a transporter peptide sequence; (b) a MYC sequence; and optionally (c) one or more molecules that link the transporter peptide sequence and the MYC sequence. In some embodiments, the peptide has Formula (I):

transporter peptide sequence-MYC sequence.

In some embodiments, the peptide has Formula (II):

transporter peptide sequence-X-MYC sequence, wherein —X— is a molecule that links the transporter peptide sequence and the MYC sequence. In some embodiments, the peptide has Formula (II):

transporter peptide sequence-X-MYC sequence, wherein in X is at least one amino acid. In some embodiments, the peptide has the following amino acid sequence:

```
                                          (SEQ ID NO: 2)
MRKKRRQRRRMDFFRVVENQQPPATMPLNVSFTNRNYDLDYDSVQPY

FYCDEEENFYQQQQQSELQPPAPSEDIWKKFELLPTPPLSPSRRSGL

CSPSYVAVTPFSLRGDNDGGGGSFSTADQLEMVTELLGGDMVNQSFI

CDPDDETFIKNIIIQDCMWSGFSAAAKLVSEKLASYQAARKDSGSPN

PARGHSVCSTSSLYLQDLSAAASECIDPSVVFPYPLNDSSSPKSCAS

QDSSAFSPSSDSLLSSTESSPQGSPEPLVLHEETPPTTSSDSEEEQE

DEEEIDVVSVEKRQAPGKRSESGSPSAGGHSKPPHSPLVLKRCHVST

HQHNYAAPPSTRKDYPAAKRVKLDSVRVLRQISNNRKCTSPRSSDTE

ENVKRRTHNVLERQRRNELKRSFFALRDQIPELENNEKAPKVVILKK

ATAYILSVQAEEQKLISEEDLLRKRREQLKHKLEQLRKGELNSKLEG

KPIPNPLLGLDSTRTGHHHHHH.
```

Disclosed herein, in certain embodiments, is a composition that induces an immune response, comprising a fusion peptide comprising: (a) a transporter peptide sequence; (b) a MYC sequence; and optionally (c) one or more molecules that link the transporter peptide sequence and the MYC sequence. In some embodiments, the peptide has Formula (I):

transporter peptide sequence-MYC sequence.

In some embodiments, the peptide has Formula (II):

transporter peptide sequence-X-MYC sequence, wherein —X— is a molecule that links the transporter peptide sequence and the MYC sequence. In some embodiments, the peptide has Formula (II):

transporter peptide sequence-X-MYC sequence, wherein in X is at least one amino acid. In some embodiments, the peptide has the following amino acid sequence: MRKKRRQRRRMDFFRVVENQQPPATMPLNVSFT-NRNYDLDYDSVQPYFYCDEEENFYQQQQ QSELQP-PAPSEDIWKKFELLPTPPLSPSRRSGLCSPSYVAVT-PFSLRGDNDGGGGSFSTADQLEM VTELLGGDMVNQSFICDPDDETFIKNIIIQDCMWSGF-SAAAKLVSEKLASYQAARKDSGSPNPA RGHSVCST-SSLYLQDLSAAASECIDPSVVFPYPLNDSSSPK-SCASQDSSAFSPSSDSLLSSTESSPQ GSPEPLVLHEETPPTTSSDSEEEQEDEEEIDVVS-VEKRQAPGKRSESGSPSAGGHSKPPHSPLVLK RCHVSTHQHNYAAPPSTRKDYPAAKRVKLDSVRVL-RQISNNRKCTSPRSSDTEENVKRRTHNV LERQRR-NELKRSFFALRDQIPELENNEKAPKVVILKKATAY-ILSVQAEEQKLISEEDLLRKRREQ LKHKLEQLRKGELNSKLEGKPIPNPLLGLDSTRTGH- HHHHH. (SEQ ID NO: 2) In some embodiments, the composition further comprises an antigen, antigenic moiety, or a combination thereof. In some embodiments, the antigen is a dead microorganism, an attenuated microorganism, a toxoid, a subunit of a pathogen, a nucleic acid, a polymer of nucleic acids, or combinations thereof. In some embodiments, the antigen is derived from: hepatitis A; hepatitis B; polio; measles; mumps; rubella; diphtheria; pertussis; tetanus; influenza; varicella zoster virus; rotavirus; meningococcal; pneumonia; smallpox; cholera; bubonic plague; yellow fever; tuberculosis; human papillomavirus; or combinations thereof. In some embodiments, the composition further comprises an antigenic moiety derived from a pathogen selected from: hepatitis A; hepatitis B; polio; measles; mumps; rubella; diphtheria; pertussis; tetanus; influenza; varicella zoster virus; rotavirus; meningococcal; pneumonia; smallpox; cholera; bubonic plague; yellow fever; tuberculosis; human papillomavirus; or combinations thereof. In some embodiments, the composition further comprises an antigenic moiety derived from a neoplastic cell. In some embodiments, the composition is formulated for topical administration.

Disclosed herein, in certain embodiments, is a method of inducing an immune response, comprising administering to an individual in need thereof: (a) a vaccine against at least one antigen, and (b) a fusion peptide comprising: (a) a transporter peptide sequence; (b) a MYC sequence; and optionally (c) one or more molecules that link the transporter peptide sequence and the MYC sequence. In some embodiments, the peptide has Formula (I):

transporter peptide sequence-MYC sequence.

In some embodiments, the peptide has Formula (II):

transporter peptide sequence-X-MYC sequence, wherein —X— is a molecule that links the transporter peptide sequence and the MYC sequence. In some embodiments, the peptide has Formula (II):

transporter peptide sequence-X-MYC sequence, wherein in X is at least one amino acid. In some embodiments, the peptide has the following amino acid sequence: MRKKRRQRRRMDFFRVVENQQPPATMPLNVSFT-NRNYDLDYDSVQPYFYCDEEENFYQQQQ QSELQP-PAPSEDIWKKFELLPTPPLSPSRRSGLCSPSYVAVT-PFSLRGDNDGGGGSFSTADQLEM VTELLGGDMVNQSFICDPDDETFIKNIIQDCMWSGF-SAAAKLVSEKLASYQAARKDSGSPNPA RGHSVCSTS SLYLQDLSAAASECIDPSVVFPYPLND SSSPK-SCASQDS SAFSPSSDSLLS STESSPQ GSPEPLVL-HEETPPTTSSDSEEEQEDEEEIDVVSVEKRQAPGKRS-ESGSPSAGGHSKPPHSPLVLK RCHVSTHQHNYAAPPSTRKDYPAAKRVKLDSVRVL-RQISNNRKCTSPRSSDTEENVKRRTHNV LERQRR-NELKRSFFALRDQIPELENNEKAPKVVILKKATAY-ILSVQAEEQKLISEEDLLRKRREQ LKHKLEQLRKGELNSKLEGKPIPNPLLGLDSTRTGH-HHHHH. (SEQ ID NO: 2) In some embodiments, the vaccine is selected from the group consisting of: hepatitis A vaccine; hepatitis B vaccine; polio vaccine; measles vaccine; mumps vaccine; rubella vaccine; diphtheria vaccine; pertussis vaccine; tetanus vaccine; influenza vaccine; varicella zoster virus vaccine; rotavirus vaccine; meningococcal vaccine; pneumonia vaccine; smallpox vaccine; cholera vaccine; bubonic plague vaccine; yellow fever vaccine; tuberculosis vaccine; human papillomavirus vaccine; a cancer vaccine; or combinations thereof. In some embodiments, the vaccine is administered before, after, or simultaneously with the agent that increases the nucleic concentration of a Myc polypeptide.

Disclosed herein, in certain embodiments, is a method of increasing the viability of a cell, comprising administering to an individual in need thereof an agent that up-regulates the expression of MYC, increases the activity of a Myc peptide, or a combination thereof. In some embodiments, the agent is a fusion peptide comprising: (a) a transporter peptide sequence; (b) a MYC sequence; and optionally (c) one or more molecules that link the transporter peptide sequence and the MYC sequence.

In some embodiments, the peptide has Formula (I):

transporter peptide sequence-MYC sequence.

In some embodiments, the peptide has Formula (II):

transporter peptide sequence-X-MYC sequence, wherein —X— is a molecule that links the transporter peptide sequence and the MYC sequence. In some embodiments, the peptide has Formula (II):

transporter peptide sequence-X-MY C sequence, wherein in X is at least one amino acid. In some embodiments, the peptide has the following amino acid sequence: MRKKRRQRRRMDFFRVVENQQPPATMPLNVSFT-NRNYDLDYDSVQPYFYCDEEENFYQQQQ QSELQP-PAPSEDIWKKFELLPTPPLSPSRRSGLCSPSYVAVT-PFSLRGDNDGGGGSFSTADQLEM VTELLGGDMVNQSFICDPDDETFIKNIIQDCMWSGF-SAAAKLVSEKLASYQAARKDSGSPNPA RGHSVCST-SSLYLQDLSAAASECIDPSVVFPYPLNDSSSPK-SCASQDSSAFSPSSDSLLSSTESSPQ GSPEPLVLHEETPPTTSSDSEEEQEDEEEIDVVS-VEKRQAPGKRSESGSPSAGGHSKPPHSPLVLK RCHVSTHQHNYAAPPSTRKDYPAAKRVKLDSVRVL-RQISNNRKCTSPRSSDTEENVKRRTHNV LERQRR-NELKRSFFALRDQIPELENNEKAPKVVILKKATAY-ILSVQAEEQKLISEEDLLRKRREQ LKHKLEQLRKGELNSKLEGKPIPNPLLGLDSTRTGH-HHHHH. (SEQ ID NO: 2) In some embodiments, the cell is a leukocyte. In some embodiments, the cell is a T-cell. In some embodiments, the cell is a B-cell. In some embodiments, the cell is a memory T-cell.

Disclosed herein, in certain embodiments, is a method of decreasing the viability of a cell, comprising administering to an individual in need thereof an agent that down-regulates the expression of MYC, decreases the activity of a Myc peptide, or a combination thereof.

Disclosed herein, in certain embodiments, is a method of treating a disorder characterized by the under-expression of a MYC gene or a deficit in the activity of a Myc polypeptide, comprising administering to an individual in need thereof an agent that up-regulates the expression of MYC, increases the activity of a Myc peptide, or a combination thereof. In some embodiments, the agent is a fusion peptide comprising: (a) a transporter peptide sequence; (b) a MYC sequence; and optionally (c) one or more molecules that link the transporter peptide sequence and the MYC sequence. In some embodiments, the peptide has Formula (I):

transporter peptide sequence-MYC sequence.

In some embodiments, the peptide has Formula (II):

transporter peptide sequence-X-MYC sequence, wherein —X— is a molecule that links the transporter peptide sequence and the MYC sequence. In some embodiments, the peptide has Formula (II):

transporter peptide sequence-X-MYC sequence, wherein in X is at least one amino acid. In some embodiments, the peptide has the following amino acid sequence:

(SEQ ID NO: 2)
MRKKRRQRRRMDFFRVVENQQPPATMPLNVSFTNRNYDLDYDSVQPY

FYCDEEENFYQQQQQSELQPPAPSEDIWKKFELLPTPPLSPSRRSGL

CSPSYVAVTPFSLRGDNDGGGGSFSTADQLEMVTELLGGDMVNQSFI

CDPDDETFIKNIIQDCMWSGFSAAAKLVSEKLASYQAARKDSGSPN

PARGHSVCSTSSLYLQDLSAAASECIDPSVVFPYPLNDSSSPKSCAS

QDSSAFSPSSDSLLSSTESSPQGSPEPLVLHEETPPTTSSDSEEEQE

DEEEIDVVSVEKRQAPGKRSESGSPSAGGHSKPPHSPLVLKRCHVST

HQHNYAAPPSTRKDYPAAKRVKLDSVRVLRQISNNRKCTSPRSSDTE

ENVKRRTHNVLERQRRNELKRSFFALRDQIPELENNEKAPKVVILKK

ATAYILSVQAEEQKLISEEDLLRKRREQLKHKLEQLRKGELNSKLEG

KPIPNPLLGLDSTRTGHHHHHH.

Disclosed herein, in certain embodiments, is a method of treating a disorder characterized by the over-expression of a MYC gene or the excess activity of a Myc polypeptide comprising, administering to an individual in need thereof an agent that down-regulates the expression of MYC, decreases the activity of a Myc peptide, or a combination thereof.

Disclosed herein, in certain embodiments, is a method of identifying an agent that up-regulates the expression of a MYC gene, and/or the activity of a Myc polypeptide, the method comprising: (a) contacting a plurality of anergic B-cells with an agent; and (b) following contact with the agent, detecting and/or measuring the level of expression of one or more cell surface markers in the cell culture, wherein the presence of the cell surface marker is indicative a non-anergic B-cell. In some embodiments, the anergic B-cells are obtained from mice with the phenotype BCR$^{HEL}$/sHEL. In some embodiments, the cell surface marker is: IgM, IgMa, IgMb, B220, CD21/35, CD23, CD24 (HSA), CD40, CD69, CD80 and/or CD86 (B7-2). In some embodiments, the level of expression of a cell surface marker is measured by contacting the plurality of cells with a detectable antibody or detectable antigen that binds to the cell surface marker.

Disclosed herein, in certain embodiments, is a method of identifying an agent that up-regulates the expression of a MYC gene, and/or the activity of a Myc polypeptide, the method comprising: (a) contacting a plurality of factor-dependent cells with an agent; and (b) following contact with the agent, detecting and measuring the level of expansion of the plurality of cells. In some embodiments, the factor-dependent cells are lymphoid cells. In some embodiments, the factor-dependent cells are: IL-2$^{-/-}$, IL-3$^{-/-}$, IL-4$^{-/-}$, IL-5$^{-/-}$, IL-6$^{-/-}$, IL-7$^{-/-}$, IL-8$^{-/-}$, IL-9$^{-/-}$, IL-10$^{-/-}$, IL-11$^{-/-}$, IL-12$^{-/-}$, or any combinations thereof. In some embodiments, the factor-dependent cells are derived from: CTLL-2 cells or BAF/3 cells.

Disclosed herein, in certain embodiments, is a method of identifying an agent that up-regulates the expression of a MYC gene, and/or the activity of a Myc polypeptide, comprising: (a) transforming a plurality of cells with a reporter construct, comprising: a reporter gene operably linked to an E-box sequence encoded in a myc-responsive promoter; (b) contacting the plurality of cells with an agent; and (c) following contact with the agent, detecting and measuring the level of expression of the reporter gene. In some embodiments, the cells are lymphoid cells. In some embodiments, the myc-responsive promoter is an ornithine decarboxylase promoter. In some embodiments, the reporter gene is a β-galactosidase gene, a β-lactamase gene, a horseradish peroxidase gene, an alkaline phosphatase gene, a thymidine kinase gene, a xanthine phosphoribotransferase gene, a tyrosinase gene, a cytosine deaminase gene, an antibiotic resistance gene, or a gene having a fluorescent expression product.

DETAILED DESCRIPTION OF THE INVENTION

Disclosed herein, in certain embodiments, are methods of identifying agents capable of modulating (e.g., activating, increasing, inducing, supplementing, decreasing, or inhibiting) an immune system. In some embodiments, agents are utilized to increase an immune response. In some embodiments, agents are used to decrease an immune response. Further, disclosed herein are methods of modulating an immune system using agents identified by any of the means disclosed herein.

Certain Definitions

Unless indicated otherwise, the following terms have the following meanings when used herein and in the appended claims.

The term "vaccine" means a composition comprising antigens and/or antigenic moieties administered to a mammal in order to elicit an immune response. The antigen or antigenic moiety is a live or attenuated microorganism, a natural product purified from a microorganism (e.g. a subunit of a protein, peptide, polysaccharide, and a nucleic acid), a synthetic product designed to mimic a component of the microorganism, a genetically engineered protein, peptide, or polysaccharide, a patient's own tumor cells, a natural product purified from a tumor cell (e.g. Prostate Specific Antigen, gp96, GM2, GD2, GD3, carcinoembryonic antigen, MART-1, and tyrosinase), a synthetic molecule designed to mimic a component of a tumor cell (e.g. sialyl Tn), or combinations thereof. Further, the term vaccine includes current vaccines, and any novel and/or modified vaccines developed.

The term "lymphoid tissue" means tissue associated with the lymphatic system. By way of non-limiting example, lymphoid tissue includes tissue obtained from the lymph nodes, tonsils, spleen, bone marrow, and thymus.

The term "lymphocyte" refers to all immature, mature, undifferentiated and differentiated white lymphocyte populations including tissue specific and specialized varieties. It encompasses, by way of non-limiting example, B-cells, T-cells, NKT cells, and NK cells. In some embodiments, lymphocytes include all B-cell lineages including pre-B-cells, Progenitor B cells, Early Pro-B cells, Late Pro-B cells, Large Pre-B cells, Small Pre-B cells, Immature B cells, Mature B cells, plasma B-cells, memory B-cells, B-1 cells, B-2 cells and anergic AN1/T3 cell populations.

The term B-cell, refers to, by way of non-limiting example, a pre-B-cell, Progenitor B cell, Early Pro-B cell, Late Pro-B cell, Large Pre-B cell, Small Pre-B cell, Immature B cell, Mature B cell, plasma B-cell, memory B-cell, B-1 cell, B-2 cells and anergic AN1/T3 cell populations. In some embodiments, the term B-cell includes a B-cell that expresses an immunoglobulin heavy chain and/or light chain on its cells surface. In some embodiments, the term B-cell includes a B-cell that expresses and secretes an immunoglobulin heavy chain and/or light chain. In some embodiments, the term B-cell includes a cell that binds an antigen on its cell-surface. In some embodiments disclosed herein, B-cells or AN1/T3 cells are utilized in the processes described. In certain embodiments, such cells are optionally substituted with any animal cell suitable for expressing, capable of expressing (e.g., inducible expression), or capable of being differentiated into a cell suitable for expressing an antibody including, e.g., a hematopoietic stem cell, a B-cell, a pre-B-cell, a Progenitor B cell, a Early Pro-B cell, a Late Pro-B cell, a Large Pre-B cell, a Small Pre-B cell, an Immature B cell, a Mature B cell, a plasma B-cell, a memory B-cell, a B-1 cell, a B-2 cell, an anergic B-cell, or an anergic AN1/T3 cell.

The term "immune response" includes the identification and neutralization of pathogens and/or tumor cells. In some embodiments, the immune response is the adaptive immune response. By way of non-limiting example, the adaptive immune response includes the development of immunological memory.

The terms "antibody" and "antibodies" refer to any form of a natural occurring (but isolated and/or purified), engineered or synthetic antibody, including monoclonal antibodies, polyclonal antibodies, bi-specific antibodies, multispecific antibodies, grafted antibodies, human antibodies, humanized antibodies, synthetic antibodies, chimeric antibodies, camelized antibodies, single-chain Fvs (scFv), single chain antibodies, Fab fragments, F(ab') fragments, disulfide-linked Fvs (sdFv), intrabodies, and anti-idiotypic (anti-Id) antibodies and antigen-binding fragments of any of the above. In particular, antibodies include immunoglobulin molecules and immunologically active fragments of immunoglobulin molecules, i.e., molecules that contain an antigen binding site. Immunoglobulin molecules are of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass. The terms "antibody" and immunoglobulin are used interchangeably in the broadest sense. In some embodiments an antibody is part of a larger molecule, formed by covalent or non-covalent association of the antibody with one or more other proteins or peptides.

The antibodies herein include monoclonal, polyclonal, recombinant, chimeric, humanized, bi-specific, grafted, human, and fragments thereof including antibodies altered by any means to be less immunogenic in humans. Thus, for example, the monoclonal antibodies and fragments, etc., herein include "chimeric" antibodies and "humanized" antibodies. In general, chimeric antibodies include a portion of the heavy and/or light chain that is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, so long as they exhibit the desired biological activity (U.S. Pat. No. 4,816,567); Morrison et al. *Proc. Natl Acad. Sci.* 81:6851-6855 (1984). For example, in some embodiments a chimeric antibody contains variable regions derived from a mouse and constant regions derived from human in whom the constant region contains sequences homologous to both human IgG2 and human IgG4. "Humanized" forms of non-human (e.g., murine) antibodies or fragments are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include, grafted antibodies or CDR grafted antibodies wherein part or all of the amino acid sequence of one or more complementarily determining regions (CDRs) derived from a non-human animal antibody is grafted to an appropriate position of a human antibody while maintaining the desired binding specificity and/or affinity of the original non-human antibody. In some embodiments, corresponding non-human residues replace Fv framework residues of the human immunoglobulin. In some embodiments humanized antibodies comprise residues that are found neither in the recipient antibody nor in the imported CDR or framework sequences. These modifications are made to further refine and optimize antibody performance. In some embodiments, the humanized antibody comprises substantially all of at least one, and typically two, variable domains, in which all or substantially all of the CDR regions correspond to those of a non-human immunoglobulin and all or substantially all of the FR regions are those of a human immunoglobulin consensus sequence. For further details, see, e.g.: Jones et al., *Nature* 321: 522-525 (1986); Reichmann et al., *Nature* 332: 323-329 (1988) and Presta, *Curr. Op. Struct. Biol.* 2: 593-596 (1992).

The term "antigen" refers to a substance that elicits the production of an antibody.

The term "antigenic moiety" means the portion of a molecule, organism (e.g., a bacteria, virus), or cell to which an antibody binds (or complements).

The term "self antigen" refers to an antigen that originates from within an animal, tissue, or cell. In some embodiments a self antigen comprises an endogenous antigen. In some embodiments a self antigen comprises an endogenous antigen produced by an endogenous retrovirus. In some embodiments self antigens comprise neo-self antigens, microbially or parasite encoded neo-self antigens, or other neo-self antigens expressed as a result of genetic alteration to an animal or cell following whole-body irradiation and HSC transplantation (which re-starts the immune system and allows the new antigen to be considered "self"). In some embodiments a chimeric mouse expresses a neo-self antigen.

The term "auto-antigen" refers to an antigen that comprises an epitope of a self antigen or an immunologically reactive epitope that mimics that of a self antigen. In some embodiments the term auto antigen comprises antigens to which autoantibodies are produced. In some embodiments an auto antigen comprises an endogenous antigen wherein the animal from which the endogenous antigen originated is or was once immunologically tolerant to the antigen.

The term "anergy" refers to a state wherein lymphocytes are inactive (e.g. they do not respond to the binding of an antigen). In some embodiments, the lymphocyte is a B-cell. In some embodiments, a B-cell becomes anergic following exposure to a circulating soluble self-antigen. In some embodiments, a B-cell becomes anergic following exposure to a soluble circulating antigen. In some embodiments, the antigen is soluble hen egg lysozyme (sHEL).

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to agents that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes.

The terms "polypeptide", peptide" and "protein" are used interchangeably herein to refer to a polymer of amino acid residues. The terms apply to naturally occurring amino acid polymers as well as amino acid polymers in which one or more amino acid residues is a non-naturally occurring amino acid, e.g., an amino acid analog. The terms encompass amino acid chains of any length, including full length proteins, wherein the amino acid residues are linked by covalent peptide bonds.

The terms "Myc protein" and "Myc polypeptide" are used synonyms and refer to the polymer of amino acid residues disclosed in NCBI Accession Number NP002458.2, and functional homologs, analogs or fragments thereof. In some embodiments, a Myc polypeptide comprises an amino acid sequence that is at least 40% to 100% identical, e.g., at least 40%, 45%, 50%, 55%, 60%, 65%, 70%, 75%, 80%, 85%, 86%, 87%, 88%, 90%, 91%, 92%, 94%, 95%, 96%, 97%, 98%, or any other percent from about 40% to about 100% identical to the sequence of NCBI Accession Numbers NP002458.2. In some embodiments, a Myc polypeptide comprises a polypeptide sequence of 40 amino acids or more in length that is at least 50% to 100% identical, e.g., at least 50%, 55%, 60%, 65%, 70%, 75%, 80%, 85%, 86%, 87%, 88%, 90%, 91%, 92%, 94%, 95%, 96%, 97%, 98%, or any other percent from about 50% to about 100% identical to the sequence of NCBI Accession Numbers NP002458.2. In some embodiments, a Myc polypeptide comprises a polypeptide sequence of 40 amino acids or more in length that is at least 50% to 100% identical, e.g., at least 50%, 55%, 60%, 65%, 70%, 75%, 80%, 85%, 86%, 87%, 88%, 90%, 91%, 92%, 94%, 95%, 96%, 97%, 98%, or any other percent from about 50% to about 100% identical to the sequence of NCBI Accession Numbers NP002458.2. In some embodiments, Myc polypeptide means a polymer of 439 amino acids, a Myc polypeptide that has not undergone any post-translational modifications, and/or a Myc polypeptide that has undergone post-translational modifications. In certain instances, the Myc polypeptide is 48,804 kDa. In certain instances, the Myc polypeptide contains a basic Helix-Loop-Helix Leucine Zipper (bHLH/LZ) domain. In certain instances, the Myc polypeptide is a transcription factor (e.g. Transcription Factor 64). In certain instances, the Myc polypeptide binds to a sequence comprising CACGTG (i.e. an E-box sequence).

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions are achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Cassol et al. (1992); Rossolini et al., Mol. Cell. Probes 8:91-98 (1994)).

The terms "MYC" and "MYC gene" are synonyms. They refer to a nucleic acid sequence that encodes a Myc polypeptide. A MYC gene comprises a nucleotide sequence of at least 120 nucleotides that is at least 60% to 100% identical or homologous, e.g., at least 60, 65%, 70%, 75%, 80%, 85%, 86%, 87%, 88%, 90%, 91%, 92%, 94%, 95%, 96%, 97%, 98%, or any other percent from about 70% to about 100% identical to sequences of NCBI Accession Number NM_002467. In some embodiments, the MYC gene is a proto-oncogene. In certain instances, a MYC gene is found on chromosome 8, at 8q24.21. In certain instances, a MYC gene begins at 128,816,862 bp from pter and ends at 128,822,856 bp from pter. In certain instances, a MYC gene is about 6 kb. In certain instances, a MYC gene encodes at least eight separate mRNA sequences—5 alternatively spliced variants and 3 unspliced variants.

To determine the percent homology of two amino acid sequences or of two nucleic acids, the sequences can be aligned for optimal comparison purposes (e.g., gaps are introduced in the sequence of a first amino acid or nucleic acid sequence for optimal alignment with a second amino or nucleic acid sequence). The amino acid residues or nucleotides at corresponding amino acid positions or nucleotide positions can then be compared. When a position in the first sequence is occupied by the same amino acid residue or nucleotide as the corresponding position in the second sequence, then the molecules are identical at that position. The percent homology between the two sequences is a function of the number of identical positions shared by the sequences (i.e., % identity=# of identical positions/total # of positions (e.g., overlapping positions)×100). In some embodiments the two sequences are the same length.

To determine percent homology between two sequences, the algorithm of Karlin and Altschul (1990) Proc. Natl. Acad. Sci. USA 87:2264-2268, modified as in Karlin and Altschul (1993) Proc. Natl. Acad. Sci. USA 90:5873-5877 is used. Such an algorithm is incorporated into the NBLAST and XBLAST programs of Altschul, et al. (1990) J. Mol. Biol. 215:403-410. BLAST nucleotide searches are performed with the NBLAST program, score=100, wordlength=12 to obtain nucleotide sequences homologous to a nucleic acid molecules described or disclose herein. BLAST protein searches are performed with the XBLAST program, score=50, wordlength=3. To obtain gapped alignments for comparison purposes, Gapped BLAST is utilized as described in Altschul et al. (1997) Nucleic Acids Res. 25:3389-3402. When utilizing BLAST and Gapped BLAST programs, the default parameters of the respective programs (e.g., XBLAST and NBLAST) are used. See the website of the National Center for Biotechnology Information for further details (on the World Wide Web at ncbi.nlm.nih.gov). Proteins suitable for use in the methods described herein also includes proteins having between 1 to 15 amino acid changes, e.g., 1, 2, 3, 4, 5, 6, 7, 8, 9, 10, 11, 12, 13, 14, or 15 amino acid substitutions, deletions, or additions, compared to the amino acid sequence of any protein described herein. In other embodiments, the altered amino acid sequence is at least 75% identical, e.g., 77%, 80%, 82%, 85%, 88%, 90%, 92%, 95%, 97%, 98%, 99%, or 100% identical to the amino acid sequence of any protein inhibitor described herein. Such sequence-variant proteins are suitable for the methods described herein as long as the altered amino acid sequence retains sufficient biological activity to be functional in the compositions and methods described herein. Where amino acid substitutions are made, the substitutions should be conservative amino acid substitutions. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff et al (1992), *Proc. Natl Acad. Sci. USA*, 89:10915-10919). Accordingly, the BLOSUM62 substitution frequencies are used to define conservative amino acid substitutions that, in some embodiments, are introduced into the amino acid sequences described or disclosed herein. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

The term "Myc activity" refers to binding of a Myc polypeptide to a nucleic acid sequence. In some embodiment, MYC activity further includes MYC regulation of the transcriptional activity of Myc responsive genes. In some embodiments, Myc activity induces cell proliferation and/or antibody production.

The terms "activation of Myc" and "Myc activation" refer to the induction of Myc activity. In some embodiments activation of Myc is induced by over-expression of a Myc polypeptide. In some embodiments activation of Myc is induced by transport of a Myc polypeptide into the nucleus of a cell. In some embodiments activation of Myc is induced by transport of a Myc polypeptide into a cell.

The term "expression" refers to one or more of the following events: (1) production of an RNA template from a DNA sequence (e.g., by transcription) within a cell; (2) processing of an RNA transcript (e.g., by splicing, editing, 5' cap formation, and/or 3' end formation) within a cell; (3) translation of an RNA sequence into a polypeptide or protein within a cell; (4) post-translational modification of a polypeptide or protein within a cell; (5) presentation of a polypeptide or protein on the cell surface; (6) secretion or release of a polypeptide or protein from a cell.

The term "endogenous" in the context of a cellular protein refers to protein naturally occurring and/or expressed by the cell in the absence of recombinant manipulation; accordingly, the terms "endogenously expressed protein" or "endogenous protein" excludes cellular proteins expressed by means of recombinant technology.

The term "factor-dependent cell" means a cell that is not able to survive and/or proliferate without contact with an exogenous growth factor (e.g. a cytokine). When contacted with the required growth-factors, a factor-dependent cell is able to survive and/or proliferate. In the absence of the required growth-factors, a factor-dependent cell cannot survive (e.g. will undergo apoptosis) and/or proliferate.

The term "expansion" as used herein refers to an enlargement in the size of the culture due to the proliferation (i.e. division) of cells in the cell culture. In some embodiments, the cell culture exhibits expansion (i.e. it attains a larger size and/or the concentration of cell in the culture increases). In some embodiments, the cell culture exhibits negative expansion (i.e. attains a smaller size or the concentration of cell in the culture decreases). In certain instances, the expansion of a cell culture is detectable and measurable in any suitable manner (e.g. staining, flow cytometry, fluorescent microscopy, HPLC, confocal microscopy, infrared spectroscopy, autoradiography).

The phrases "E-box sequence" and "enhancer box sequence" are used interchangeably herein and mean the nucleotide sequence CANNTG, wherein N is any nucleotide. In certain instances, the E-box sequence comprises CACGTG. In certain instances, the basic helix-loop-helix domain of a transcription factor encoded by MYC binds to the E-box sequence. In certain instances the E-box sequence is located upstream of a gene (e.g. p21, Bcl-2, or ornithine decarboxylase). In certain instances, the binding of the transcription factor encoded by MYC to the E-box sequence, allows RNA polymerase to transcribe the gene downstream of the E-box sequence.

Methods of Modulating the Viability of a Cell

Disclosed herein, in some embodiments, are methods of modulating the viability of a cell. As used herein, "viability" means the length of time the cell survives, the rate (or amount) of cellular proliferation, or a combination thereof. In some embodiments, the viability of a cell is increased. In some embodiments, the viability of a cell is decreased.

In some embodiments, the modulation occurs in vivo. In some embodiments, the modulation occurs in vitro. In some embodiments, a method of modulating the viability of a cell comprises modulating the viability of a leukocyte. In some embodiments, the leukocyte is a T-cell. In some embodiments, the leukocyte is a CD4+ T-cell. In some embodiments, the leukocyte is a memory T-cell.

In some embodiments, modulating the viability of a cell comprises modulating the expression of a MYC gene, and/or the activity of a Myc polypeptide. In some embodiments, modulating the expression of a MYC gene, and/or the activity of a Myc polypeptide directly or indirectly results in the modulation of a gene or polypeptide regulated by MYC. In some embodiments, the gene or polypeptide directly or indirectly regulated by a MYC transcription factor is: neurogranin, MEF-2c, gfi-1, cyclin D2, CDK4, Egr-2, Nab-2, TGIF, NF-kB p105, Carma-1, A1 or Bcl-2.

Increasing the Viability of a Cell

In some embodiments, modulating the viability of a cell means increasing the viability of a cell. In some embodiments, increasing the viability of a cell means: increasing the length of time the cell survives (e.g. as compared to an identical or similar unmodulated cell of the same type), increasing the rate or amount of cellular proliferation (e.g. as compared to an identical or similar unmodulated cell of the same type), or a combination thereof.

In some embodiments, increasing the viability of a cell comprises contacting a cell with an agent that increases the nucleic concentration of a Myc polypeptide. In some embodiments, increasing the viability of a cell comprises contacting a cell with: an exogenous Myc polypeptide, an agent that increases the expression of a MYC gene, and an agent that increases the activity of a Myc polypeptide, or a combination thereof (the "MYC Increasing Agent"). In some embodiments, the MYC Increasing Agent is a small molecule, a peptide, an antibody, or a combination thereof.

In some embodiments, a method of increasing the viability of a cell comprises contacting a cell with the MYC Increasing Agent. In some embodiments, the MYC Increasing Agent is an exogenous Myc polypeptide. In some embodiments, the MYC Increasing Agent is a fusion peptide comprising (a) a transporter peptide sequence; (b) a MYC sequence; and optionally (c) one or more molecules that link the transporter peptide sequence and the MYC sequence. In some embodiments, the MYC Increasing Agent is a fusion peptide comprising (a) a TAT sequence; and (b) a MYC sequence.

In some embodiments, a method of increasing the viability of a cell comprises contacting a cell with the MYC Increasing Agent. In some embodiments, the MYC Increasing Agent is an antagonist of a MAD-1 gene. In certain instances, the down-regulation of a MAD-1 gene and/or polypeptide upregulates the expression of a MYC gene and/or a polypeptide encoded by a MYC gene.

In some embodiments, a method of increasing the viability of a cell comprises contacting a cell with the MYC Increasing Agent. In some embodiments, the MYC Increasing Agent is an antagonist of a Mxi-1 gene. In certain instances, the down-regulation of a Mxi-1 gene and/or polypeptide upregulates the expression of a MYC gene and/or a polypeptide encoded by a MYC gene.

In some embodiments, a method of increasing the viability of a cell further comprises identifying the MYC Increasing Agent. In some embodiments, the method of identifying the MYC Increasing Agent comprises identifying an agent that reverses anergy in a B-cell. In some embodiments, the method of identifying the MYC Modulating Agent comprises identifying an agent that increases the viability of a factor-dependent cell in the absence of a required growth factor. In some embodiments, the method of identifying the MYC Increasing Agent comprises identifying an agent that induces expression of a reporter gene under the control of a MYC responsive promoter (e.g. an E-box sequence).

In some embodiments, following contact with the MYC Increasing Agent the viability of a cell is increased by about 1 to about 20 times (e.g. as compared to an identical or similar unmodulated cell of the same type). In some embodiments, following contact with the MYC Increasing Agent the viability of a cell is increased by about 1 to about 15 times (e.g. as compared to an identical or similar unmodulated cell of the same type). In some embodiments, following contact with the MYC Increasing Agent the viability of a cell is increased by about 1 to about 10 times (e.g. as compared to an identical or similar unmodulated cell of the same type). In some embodiments, following contact with the MYC Increasing Agent the viability of a cell is increased by about 1 to about 5 times (e.g. as compared to an identical or similar unmodulated cell of the same type). In some embodiments, following contact with the MYC Increasing Agent the viability of a cell is increased by about 1 to about 4 times (e.g. as compared to an identical or similar unmodulated cell of the same type). In some embodiments, following contact with the MYC Increasing Agent the viability of a cell is increased by 1 to about 2 times (e.g. as compared to an identical or similar unmodulated cell of the same type).

In some embodiments, the cell is a T-cell. In some embodiments, the T-cell is a memory T-cell. In some embodiments, modulating the viability of a T-cell means extending the life-span of a T-cell. In some embodiments, extending the life span of a memory T-cell results in a higher concentration of memory T-cells in a body. In certain instances, the higher concentration of memory T-cells results in an accelerated primary immune response to antigen. In certain instances, the up-regulation of a MYC gene results in a decrease in anergic T-cells. In certain instances, the decrease in anergic T-cells results in an accelerated primary immune response to antigen. In certain instances, the up-regulation of a MYC gene results in a decrease in the time it takes a T-cell to activate in response to an antigen. In certain instances, the decrease in the time it takes a T-cell to activate in response to an antigen results in an accelerated primary immune response to antigen.

Decreasing the Viability of a Cell

In some embodiments, modulating the viability of a cell means decreasing the viability of a cell. In some embodiments, decreasing the viability of a cell means: decreasing the length of time the cell survives and decreasing the rate or amount of cellular proliferation (e.g., as compared to an identical or similar unmodulated cell of the same type). In some embodiments, decreasing the viability of a cell means decreasing the length of time the cell survives and decreasing the rate or amount of cellular proliferation (e.g. as compared to an identical or similar unmodulated cell of the same type).

In some embodiments, decreasing the viability of a cell comprises contacting a cell with an agent that decreases the nucleic concentration of MYC. In some embodiments, decreasing the viability of a cell comprises contacting a cell with: an agent that decreases the expression of a MYC gene, an agent that decreases the activity of a Myc polypeptide, or a combination thereof (the "MYC Decreasing Agent"). In some embodiments, the MYC Decreasing Agent is a small molecule, a biologic, a peptide, an antibody, or a combination thereof.

In some embodiments, a method of decreasing the viability of a cell comprises contacting a cell with the MYC Decreasing Agent. In some embodiments, the MYC Decreasing Agent is an agonist of a MAD-1 gene, a MAD-1 polypeptide, or a combination thereof. In certain instances, the up-regulation of a MAD-1 gene and/or polypeptide down-regulates the expression of a MYC gene and/or a polypeptide encoded by a MYC gene. In some embodiments, a method of modulating the viability of a cell comprises contacting a cell with the MYC Decreasing Agent.

In some embodiments, a method of decreasing the viability of a cell comprises contacting a cell with the MYC Decreasing Agent. In some embodiments, the MYC Decreasing Agent is: Mxi-1an agonist of a Mxi-1 gene and a Mxi-1 polypeptide, or a combination thereof. In certain instances, the up-regulation of a Mxi-1 gene and/or polypeptide down-regulates the expression of a MYC gene and/or a polypeptide encoded by a MYC gene.

In some embodiments, the method of identifying the MYC Decreasing Agent comprises identifying an agent that decreases the viability of a factor-dependent cell when the factor-dependent cell is contacted with the necessary growth factor. In some embodiments, the method of identifying the MYC Decreasing Agent comprises identifying an agent that inhibits expression of a reporter gene under the control of a MYC responsive promoter (e.g. an E-box sequence).

In some embodiments, the viability of a cell is decreased by about 1 to about 25 times (e.g. as compared to an identical or similar unmodulated cell of the same type). In some embodiments, the viability of a cell is decreased by about 1 to about 20 times (e.g. as compared to an identical or similar unmodulated cell of the same type). In some embodiments, the viability of a cell is decreased by about 1 to about 15 times (e.g. as compared to an identical or similar unmodulated cell of the same type). In some embodiments, the viability of a cell is decreased by about 1 to about 10 times (e.g. as compared to an identical or similar unmodulated cell of the same type). In some embodiments, the viability of a cell is decreased by about 1 to about 5 times (e.g. as compared to an identical or similar unmodulated cell of the same type). In some embodiments, the viability of a cell is decreased by about 1 to about 4 times (e.g. as compared to an identical or similar unmodulated cell of the same type). In some embodiments, the viability of a cell is decreased by about 1 to about 2 times (e.g. as compared to an identical or similar unmodulated cell of the same type).

In some embodiments, the cell is a T-cell. In some embodiments, the T-cell is a memory T-cell. In certain instances, the down-regulation of a MYC gene results in a decreased life-span for the T-cell. In certain instances, the decreased life span of a memory T-cell results in a lower concentration of memory T-cells in a body. In certain instances, the lower concentration of memory T-cells results in a decelerated primary immune response to antigen, treatment of an autoimmune disorder, and/or immunosuppression. In certain instances, the down-regulation of a MYC gene results in an increase in anergic T-cells. In certain instances, the increase in anergic T-cells results in a decelerated primary immune response to antigen, treatment of an autoimmune disorder, and/or immunosuppression. In certain instances, the down-regulation of a MYC gene results in an increase in the time it takes a T-cell to activate in response to an antigen. In certain instances, the increase in the time it takes a T-cell to activate in response to an antigen results in a decelerated primary immune response to antigen, treatment of an autoimmune disorder, and/or immunosuppression.

Methods of Modulating an Immune Response

Disclosed herein, in certain embodiments, is a method of modulating an immune response. In some embodiments, the immune response is an adaptive immune response (e.g. memory B-cells and memory T-cells). In some embodiments, modulating an immune response means increasing (e.g., inducing, supplementing, amplifying) an immune response. In some embodiments, modulating an immune response means decreasing (e.g., inhibiting or suppressing) an immune response. In some embodiments, the modulation occurs in vitro. In some embodiments, the modulation occurs in vivo.

In some embodiments, a method of modulating an immune response comprises modulating the viability of a lymphocyte. In some embodiments, the lymphocyte is a T-cell. In some embodiments, the T-cell is a CD4+ T-cell. In some embodiments, the T-cell is a memory T-cell.

In some embodiments, modulating an immune response comprises modulating the expression of a MYC gene, and/or the activity of a Myc polypeptide. In some embodiments, modulating the expression of a MYC gene, and/or the activity of a Myc polypeptide directly or indirectly results in the modulation of a gene or polypeptide regulated by MYC. In some embodiments, the gene or polypeptide directly or indirectly regulated by a MYC transcription factor is neurogranin, MEF-2c, gfi-1, cyclin D2, CDK4, Egr-2, Nab-2, TGIF, NF-kB p105, Carma-1, A1 or Bcl-2.

In some embodiments, the subject is a human.

Inducing an Immune Response

In some embodiments, modulating an immune response means increasing (e.g., inducing, supplementing, amplifying) an immune response. In some embodiments, increasing an immune response includes increasing the lifespan of a T-cell, increasing the rate of proliferation by a T-cell, increasing the rate at which a memory T-cell responds to an antigen, decreasing the number of anergic cells, and/or increasing the rate at which a cell ends anergy (e.g. as compared to an identical or similar unmodulated cell of the same type).

In some embodiments, increasing an immune response comprises administering to an individual in need thereof an agent that increases the nucleic concentration of MYC. In some embodiments, increasing an immune response comprises administering to an individual in need thereof: exogenous MYC, an agent that increases the expression of a MYC gene, and an agent that increases the activity of MYC (the "MYC Increasing Agent"). In some embodiments, the MYC Increasing Agent is a small molecule, a biologic, a peptide, an antibody, or a combination thereof.

In some embodiments, a method of increasing an immune response comprises contacting a cell with the MYC Increasing Agent. In some embodiments, the MYC Increasing Agent is an exogenous Myc polypeptide. In some embodiments, the MYC Increasing Agent is a fusion peptide comprising (a) a transporter peptide sequence; (b) a MYC sequence; and optionally (c) one or more molecules that link the transporter peptide sequence and the MYC sequence. In some embodiments, the MYC Increasing Agent is a fusion peptide comprising (a) a TAT sequence; and (b) a MYC sequence.

In some embodiments, a method of increasing an immune response comprises contacting a cell with the MYC Increasing Agent. In some embodiments, the MYC Increasing Agent is an antagonist of a MAD-1 gene. In certain instances, the down-regulation of a MAD-1 gene and/or polypeptide upregulates the expression of a MYC gene and/or a polypeptide encoded by a MYC gene.

In some embodiments, a method of increasing an immune response comprises contacting a cell with the MYC Increasing Agent. In some embodiments, the MYC Increasing Agent is an antagonist of a Mxi-1 gene. In certain instances, the down-regulation of a Mxi-1 gene and/or polypeptide upregulates the expression of a MYC gene and/or a polypeptide encoded by a MYC gene.

In some embodiments, following contact with the MYC Increasing Agent, an immune response is increased by more than 1 to about 20 times (e.g. as compared to an identical or similar unmodulated immune response of the same type). In some embodiments, following contact with the MYC Increasing Agent an immune response is increased by more than 1 to about 15 times (e.g. as compared to an identical or similar unmodulated immune response of the same type). In some embodiments, following contact with the MYC Increasing Agent an immune response is increased by more than 1 to about 10 times (e.g. as compared to an identical or similar unmodulated immune response of the same type). In some embodiments, following contact with the MYC Increasing Agent an immune response is increased by more than 1 to about 5 times (e.g. as compared to an identical or similar unmodulated immune response of the same type). In some embodiments, following contact with the MYC Increasing Agent an immune response is increased by more than 1 to about 4 times (e.g. as compared to an identical or similar unmodulated immune response of the same type). In some embodiments, following contact with the MYC Increasing Agent an immune response is increased by more than 1 to about 2 times (e.g. as compared to an identical or similar unmodulated immune response of the same type).

In some embodiments, a method of increasing an immune response comprises administering a MYC Increasing Agent to an individual in need thereof. In some embodiments, following administration of the MYC Increasing Agent to an individual in need thereof, an immune response is increased by more than 1 to about 10 times (e.g. as compared to an identical or similar unmodulated immune response of the same type). In some embodiments, following administration of the MYC Increasing Agent to an individual in need thereof, an immune response is increased by more than 1 to about 20 times (e.g. as compared to an identical or similar unmodulated immune response of the same type). In some embodiments, following administration of the MYC Increasing Agent to an individual in need thereof, an immune response is increased by more than 1 to about 15 times (e.g. as compared to an identical or similar unmodulated immune response of the same type). In some embodiments, following administration of the MYC Increasing Agent to an individual in need thereof, an immune response is increased by more than 1 to about 10 times (e.g. as compared to an identical or similar unmodulated immune response of the same type). In some embodiments, following administration of the MYC Increasing Agent to an individual in need thereof, an immune response is increased by more than 1 to about 5 times (e.g. as compared to an identical or similar unmodulated immune response of the same type). In some embodiments, following administration of the MYC Increasing Agent to an individual in need thereof, an immune response is increased by more than 1 to about 4 times (e.g. as compared to an identical or similar unmodulated immune response of the same type). In some embodiments, following administration of the MYC Increasing Agent to an individual in need thereof, an immune response is increased by more than 1 to about 2 times (e.g. as compared to an identical or similar unmodulated immune response of the same type).

In some embodiments, a method of increasing an immune response further comprises co-administering a vaccine. In some embodiments, the vaccine is administered before, after, or simultaneously with a MYC Increasing Agent. In some embodiments, the MYC Increasing Agent stimulates the immune system and increases the response of the immune system to a vaccine. In some embodiments, the MYC Increasing Agent augments an immune response. In some embodiments, the MYC Increasing Agent acts synergistically with the vaccine. In some embodiments, the agent is a vaccine adjuvant.

In some embodiments, a vaccine comprises dead microorganisms, attenuated microorganisms, toxoids, subunits of the pathogen, nucleic acids, or combinations thereof. In some embodiments, the vaccine is a vaccine for hepatitis A; hepatitis B; polio; measles; mumps; rubella; diphtheria; pertussis; tetanus; influenza; varicella zoster virus; rotavirus; influenza; meningococcal disorder; pneumonia; smallpox; cholera; bubonic plague; yellow fever; tuberculosis: human paplomavirus (HPV); malaria; leishmania; *Candida albicans*; an allergen; or combinations thereof. In some embodiments, the vaccine is a vaccine for a cancer (e.g. Follicular B-cell Non-Hodgkin's Lymphoma, prostate cancer, multiple myeloma, kidney cancer, cutaneous melanoma, and ocular melanoma). In some embodiments, a cancer vaccine is a patient-specific vaccine (e.g. the vaccine comprises a patient's own tumor cells). In some embodiments, a cancer vaccine comprises Prostate Specific Antigen (PSA). In some embodiments, a cancer vaccine comprises sialyl Tn (STn). In some embodiments, a cancer vaccine comprises Heat Shock Proteins (HSPs) (e.g., gp96). In some embodiments, a cancer vaccine comprises ganglioside molecules (e.g., GM2, GD2, and GD3). In some embodiments, a cancer vaccine comprises carcinoembryonic antigen (CEA). In some embodiments, a cancer vaccine comprises MART-1 (also known as Melan-A). In some embodiments, a cancer vaccine comprises tyrosinase. In some embodiments, the vaccine is a DNA vaccine.

In some embodiments, the vaccine comprises an antigenic moiety. In some embodiments, the antigenic moiety is a toxoid, a peptide, a nucleic acid sequence, a polysaccharide, or a combination thereof. In some embodiments, the antigenic moiety is derived from a pathogen selected from: hepatitis A; hepatitis B; polio; measles; mumps; rubella; diphtheria; pertussis; tetanus; influenza; varicella zoster virus; rotavirus; meningococcal; pneumonia; smallpox; cholera; bubonic plague; yellow fever; tuberculosis; human papillomavirus; or combinations thereof. In some embodiments, the antigenic moiety is derived a neoplastic cell. In some embodiments, the antigenic moiety is a nucleic acid or a polymer of nucleic acids.

In some embodiments, increasing an immune response in an individual receiving vaccination against an antigen results in an increase in the viability (and thus concentration) of memory T-cells, B-cells, or a combination thereof against that antigen. In certain instances, increasing an immune response in an individual receiving vaccination against an antigen results in accelerated activation of the T-cell by the antigen. In certain instances, increasing an immune response in an individual receiving vaccination against an antigen results in a decrease in anergic T-cells.

In some embodiments, a method of increasing an immune response further comprises identifying the MYC Increasing Agent. In some embodiments, the method of identifying the MYC Increasing Agent comprises identifying an agent that reverses anergy in a B-cell. In some embodiments, the method of identifying the MYC Increasing Agent comprises identifying an agent that increases the viability of a factor-dependent cell in the absence of a required growth factor. In some embodiments, the method of identifying the MYC Increasing Agent comprises identifying an agent that induces expression of a reporter gene under the control of a MYC responsive promoter (e.g. an E-box sequence).

Decreasing an Immune Response

In some embodiments, modulating an immune response means decreasing (e.g., inhibiting or suppressing) an immune response. In some embodiments, decreasing an immune response includes decreasing the lifespan of a T-cell, decreasing proliferation by a T-cell, decreasing the rate at which a memory T-cell responds to an antigen, increasing the number of anergic cells, and/or decreasing the rate at which a cell ends anergy (e.g. as compared to an identical or similar unmodulated cell of the same type).

In some embodiments, decreasing an immune response comprises administering to an individual in need thereof an agent that decreases the nucleic concentration of MYC. In some embodiments, decreasing an immune response comprises administering to an individual in need thereof: an agent that decreases the expression of a MYC gene and an agent that decreases the activity of a Myc polypeptide (the "MYC Decreasing Agent"). In some embodiments, the MYC Decreasing Agent is a small molecule, a biologic, a peptide, an antibody, or a combination thereof.

In some embodiments, a method of decreasing an immune response comprises contacting a cell with the MYC Decreasing Agent. In some embodiments, the MYC Decreasing Agent is: an agonist of a MAD-1 gene, a MAD-1 polypeptide, or a combination thereof. In certain instances, the up-regulation of a MAD-1 gene and/or polypeptide down-regulates the expression of a MYC gene and/or a polypeptide encoded by a MYC gene.

In some embodiments, a method of decreasing an immune response comprises contacting a cell with the MYC Decreasing Agent. In some embodiments, the MYC Decreasing Agent is: Mxi-1an agonist of a Mxi-1 gene and a Mxi-1 polypeptide, or a combination thereof. In certain instances, the up-regulation of a Mxi-1 gene and/or polypeptide down-regulates the expression of a MYC gene and/or a polypeptide encoded by a MYC gene.

In some embodiments, following contact with the MYC Decreasing Agent an immune response is decreased by more than 1 to about 25 times (e.g. as compared to an identical or similar unmodulated immune response of the same type). In some embodiments, following contact with the MYC Decreasing Agent an immune response is decreased by more than 1 to about 20 times (e.g. as compared to an identical or similar unmodulated immune response of the same type). In some embodiments, following contact with the MYC Decreasing Agent an immune response is decreased by more than 1 to about 15 times (e.g. as compared to an identical or similar unmodulated immune response of the same type). In some embodiments, following contact with the MYC Decreasing Agent an immune response is decreased by more than 1 to about 10 times (e.g. as compared to an identical or similar unmodulated immune response of the same type). In some embodiments, following contact with the MYC Decreasing Agent an immune response is decreased by more than 1 to about 5 times (e.g. as compared to an identical or similar unmodulated immune response of the same type). In some embodiments, following contact with the MYC Decreasing Agent an immune response is decreased by more than 1 to about 4 times (e.g. as compared to an identical or similar unmodulated immune response of the same type). In some embodiments, following contact with the MYC Decreasing Agent an immune response is decreased by more than 1 to about 2 times (e.g. as compared to an identical or similar unmodulated immune response of the same type).

In some embodiments, a method of decreasing an immune response comprises administering a MYC Decreasing Agent to an individual in need thereof. In some embodiments, following administration of the MYC Decreasing Agent to an individual in need thereof an immune response is increased by more than 1 to about 25 times (e.g. as compared to an identical or similar unmodulated immune response of the same type). In some embodiments, following administration of the MYC Decreasing Agent to an individual in need thereof an immune response is increased by more than 1 to about 20 times (e.g. as compared to an identical or similar unmodulated immune response of the same type). In some embodiments, following administration of the MYC Decreasing Agent to an individual in need thereof an immune response is increased by more than 1 to about 15 times (e.g. as compared to an identical or similar unmodulated immune response of the same type). In some embodiments, following administration of the MYC Decreasing Agent to an individual in need thereof an immune response is increased by more than 1 to about 10 times (e.g. as compared to an identical or similar unmodulated immune response of the same type). In some embodiments, following administration of the MYC Decreasing Agent to an individual in need thereof an immune response is increased by more than 1 to about 5 times (e.g. as compared to an identical or similar unmodulated immune response of the same type). In some embodiments, following administration of the MYC Decreasing Agent to an individual in need thereof an immune response is increased by more than 1 to about 4 times (e.g. as compared to an identical or similar unmodulated immune response of the same type). In some embodiments, following administration of the MYC Decreasing Agent to an individual in need thereof an immune response is increased by more than 1 to about 2 times (e.g. as compared to an identical or similar unmodulated immune response of the same type).

In some embodiments, a method of decreasing an immune response comprises administering the MYC Decreasing Agent to an individual with an autoimmune disorder. In some embodiments, the MYC Decreasing Agent decreases an immune response. In certain instances, decreasing an immune response in an individual with an autoimmune disorder ameliorates and/or prevents an immune response against self antigens by the subject's immune system. In some embodiments, the autoimmune disorder is Castleman's Disorder, lupus, multiple sclerosis, scleroderma pigmentosa, Autoimmune Lymphoproliferative Syndrome (ALPS), myesthenia gravis, diabetes, asthma, rheumatoid arthritis, vitiligo, diGeorge's syndrome, Grave's disorder, Crohn's disorder, inflammatory bowel disorder, colitis, orchitis, scleroderma pigmentosa, uveitis, Post-Transplant Lymphoproliferative Disorder (PTLD), or Autoimmune Disorder-Associated Lymphadenopathy (ADAL).

In some embodiments, a method of decreasing an immune response comprises administering the MYC Decreasing Agent to an individual that is receiving, will receive, or has received an organ or bone marrow transplant (the "Transplant"). In some embodiments, the MYC Decreasing Agent decreases an immune response. In certain instances, decreasing an immune response in an individual that is receiving, will receive, or has received an organ transplant, or a bone marrow transplant ameliorates and/or prevents an immune response against the Transplant.

In some embodiments, the method of identifying the MYC Decreasing Agent comprises identifying an agent that decreases the viability of a factor-dependent cell when the factor-dependent cell is contacted with the necessary growth factor. In some embodiments, the method of identifying the MYC Decreasing Agent comprises identifying an agent that inhibits expression of a reporter gene under the control of a MYC responsive promoter (e.g. an E-box sequence).

Methods of Modulating a Disorder Characterized by the Aberrant Expression of a MYC Gene or the Aberrant Activity of a MYC Polypeptide Disclosed herein, in certain embodiments, are methods of treating a disorder characterized by an over-expression of MYC or an excess of Myc polypeptide activity. Further disclosed herein, in certain embodiments, are methods of treating a disorder characterized by an under-expression of MYC or a dearth of Myc polypeptide activity. In some embodiments, the method comprises administering to an individual in need thereof an effective amount of an agent that modulates the expression of a MYC gene, and/or the activity of a Myc polypeptide.

Disclosed herein, in certain embodiments, are methods of treating a disorder characterized by an under-expression of MYC or a dearth of Myc polypeptide activity. In some embodiments, the method comprises administering to an individual in need thereof an effective amount of a MYC Increasing Agent. In some embodiments, the MYC Increasing Agent is a small molecule, a biologic, a peptide, an antibody, or a combination thereof.

In some embodiments, the method comprises administering to an individual in need thereof an effective amount of a MYC Increasing Agent. In some embodiments, the MYC Increasing Agent is an exogenous Myc polypeptide. In some embodiments, the MYC Increasing Agent is a fusion peptide comprising (a) a transporter peptide sequence; (b) a MYC sequence; and optionally (c) one or more molecules that link the transporter peptide sequence and the MYC sequence. In some embodiments, the MYC Increasing Agent is a fusion peptide comprising (a) a TAT sequence; and (b) a MYC sequence.

In some embodiments, the method comprises administering to an individual in need thereof an effective amount of a MYC Increasing Agent. In some embodiments, the MYC Increasing Agent is an antagonist of a MAD-1 gene. In certain instances, the down-regulation of a MAD-1 gene and/or polypeptide upregulates the expression of a MYC gene and/or a polypeptide encoded by a MYC gene.

In some embodiments, the method comprises administering to an individual in need thereof an effective amount of a MYC Increasing Agent. In some embodiments, the MYC Increasing Agent is an antagonist of a Mxi-1 gene. In certain instances, the down-regulation of a Mxi-1 gene and/or polypeptide upregulates the expression of a MYC gene and/or a polypeptide encoded by a MYC gene.

Disclosed herein, in certain embodiments, are methods of treating a disorder characterized by an over-expression of MYC or an excess of Myc polypeptide activity. In some embodiments, the method comprises administering to an individual in need thereof an effective amount of a MYC Decreasing Agent. In some embodiments, the MYC Decreasing Agent is a small molecule, a biologic, a peptide, an antibody, or a combination thereof.

In some embodiments, the method comprises administering to an individual in need thereof an effective amount of a MYC Decreasing Agent. In some embodiments, the MYC Decreasing Agent is: an agonist of a MAD-1 gene, a MAD-1 polypeptide, or a combination thereof. In certain instances, the up-regulation of a MAD-1 gene and/or polypeptide down-regulates the expression of a MYC gene and/or a polypeptide encoded by a MYC gene.

In some embodiments, the method comprises administering to an individual in need thereof an effective amount of a MYC Decreasing Agent. In some embodiments, a method of modulating the viability of a cell comprises contacting a cell with the MYC Decreasing Agent. In some embodiments, the MYC Decreasing Agent is: Mxi-1 an agonist of a Mxi-1 gene and a Mxi-1 polypeptide, or a combination thereof. In certain instances, the up-regulation of a Mxi-1 gene and/or polypeptide down-regulates the expression of a MYC gene and/or a polypeptide encoded by a MYC gene.

In some embodiments, an indication that an individual over-expresses MYC or that a Myc polypeptide is excessively active is the development of an autoimmune disorder. In some embodiments, the autoimmune disorder is Castleman's Disease, lupus, multiple sclerosis, scleroderma pigmentosa, Autoimmune Lymphoproliferative Syndrome (ALPS), myesthenia gravis, diabetes, asthma, rheumatoid arthritis, vitiligo, diGeorge's syndrome, Grave's disease, Crohn's disease, inflammatory bowel disease, colitis, orchitis, scleroderma pigmentosa, uveitis, Post-Transplant Lymphoproliferative Disease (PTLD), Autoimmune Disease-Associated Lymphadenopathy (ADAL), rejection of an organ transplant, rejection of a tissue transplant, or combinations thereof.

In some embodiments, an indication that an individual under-expresses MYC, or that a Myc polypeptide is minimally active or inactive is an increase in the number of anergic B-cells and/or T-cells. In certain instances, the expression of IgM, IgMa, IgMb, B220, CD21/35, CD23, CD24 (HSA), CD40, CD69, CD80 and/or CD86 (B7-2) is down-regulated in anergic B-cells when compared to non-anergic B-cells. In certain instances, reversing (e.g. partially or fully) anergy results in an increase in the expression of IgM, IgMa, IgMb, B220, CD21/35, CD23, CD24 (HSA), CD40, CD69, CD80 and/or CD86 (B7-2).

In some embodiments, a method of treating a disorder characterized by aberrant expression of a MYC gene or aberrant activity of a Myc polypeptide comprises identifying an agent that reverses anergy in a B-cell. In some embodiments, a method of treating a disorder characterized by aberrant expression of a MYC gene or aberrant activity of a Myc polypeptide comprises identifying an agent that increases the viability of a factor-dependent cell in the absence of a required growth factor. In some embodiments, a method of treating a disorder characterized by aberrant expression of a MYC gene or aberrant activity of a Myc polypeptide comprises identifying an agent that decreases the viability of a factor-dependent cell when the factor-dependent cell is contacted with the necessary growth factor. In some embodiments, a method of treating a disorder characterized by aberrant expression of a MYC gene or aberrant activity of a Myc polypeptide comprises identifying an agent that induces expression of a reporter gene under the control of a MYC responsive promoter (e.g. an E-box sequence). In some embodiments, a method of treating a disorder characterized by aberrant expression of a MYC gene or aberrant activity of a Myc polypeptide comprises identifying an agent that inhibits expression of a reporter gene under the control of a MYC responsive promoter (e.g. an E-box sequence).

Exogenous MYC

Disclosed herein, in certain embodiments, is a fusion peptide comprising (a) a transporter peptide sequence; and (b) a MYC sequence. In some embodiments, the fusion peptide is a peptide of Formula (I):

transporter peptide sequence-MYC sequence.

In some embodiments, a fusion peptide disclosed herein comprises (a) a transporter peptide sequence; (b) a MYC sequence; and (c) one or more molecules that link the transporter peptide sequence and the MYC sequence. In some embodiments, the fusion peptide is a peptide of Formula (II):

transporter peptide sequence-X-MYC sequence, wherein —X— is molecule that links the transporter peptide sequence and the MYC sequence. In some embodiments, —X— is an amino acid. In some embodiments, —X— is at least one amino acid.

As used herein, a "transporter peptide" means a peptide sequence that promotes peptide penetration into cells and tissues. In some embodiments, a transporter peptide is TAT. In some embodiments, a transporter peptide is $TAT_{[48-57]}$. In some embodiments, a transporter peptide is $TAT_{[57-48]}$.

As used herein, a "MYC sequence" is a MYC amino acid peptide sequence. In some embodiments, the Myc polypeptide is a complete Myc polypeptide sequence. In some embodiments, the Myc polypeptide is a partial Myc polypeptide sequence. In some embodiments, the MYC is c-MYC. In some embodiments, the Myc polypeptide sequence comprises SEQ ID NO. 1:

MDFFRVVENQQPPATMPLNVSFTNRNYDLDYDSVQPYFYCDEEENFY

QQQQQSELQPPAPSEDIWKKFELLPTPPLSPSRRSGLCSPSYVAVTP

FSLRGDNDGGGGSFSTADQLEMVTELLGGDMVNQSFICDPDDETFIK

NIIIQDCMWSGFSAAAKLVSEKLASYQAARKDSGSPNPARGHSVCST

SSLYLQDLSAAASECIDPSVVFPYPLNDSSSPKSCASQDSSAFSPSS

DSLLSSTESSPQGSPEPLVLHEETPPTTSSDSEEEQEDEEEIDVVSV

EKRQAPGKRSESGSPSAGGHSKPPHSPLVLKRCHVSTHQHNYAAPPS

TRKDYPAAKRVKLDSVRVLRQISNNRKCTSPRSSDTEENVKRRTHNV

LERQRRNELKRSFFALRDQIPELENNEKAPKVVILKKATAYILSVQA

EEQKLISEEDLLRKRREQLKHKLEQLRKGELNSKLE.

In some embodiments, a fusion peptide disclosed herein comprises (a) TAT, and (b) c-MYC. In some embodiments, a fusion peptide disclosed herein comprises (a) TAT$_{[48-57]}$, and (b) c-MYC. In some embodiments, a fusion peptide disclosed herein comprises (a) TAT$_{[57-48]}$, and (b) c-MYC.

In some embodiments, a fusion peptide disclosed herein comprises (a) TAT, (b) a linker amino acid, and (c) c-MYC. In some embodiments, a fusion peptide disclosed herein comprises (a) TAT$_{[48-57]}$, (b) a linker amino acid, and (c) c-MYC. In some embodiments, a fusion peptide disclosed herein comprises (a) TAT$_{[57-48]}$, (b) a linker amino acid, and (c) c-MYC.

In some embodiments, a fusion peptide disclosed herein further comprises at least one amino acid sequence that facilitates purification of the fusion protein. In some embodiments, a fusion peptide disclosed herein comprises a protein tag. In some embodiments, a fusion peptide disclosed herein comprises a polyhistidine tag. In some embodiments, a fusion peptide disclosed herein comprises an epitope tag. In some embodiments, a fusion peptide disclosed herein comprises a polyhistidine tag and an epitope tag. In some embodiments, a fusion peptide disclosed herein comprises a 6-histidine tag and a V5 epitope tag.

In some embodiments, the histidine tag is a 6-histidine tag. In some embodiments, the histidine tag comprises the sequence HHHHHH (SEQ ID NO:3). In some embodiments, a histidine tag is added to a fusion protein disclosed herein by any suitable method. In some embodiments, a TAT-Myc polypeptide sequence is cloned into an expression vector encoding a polyHis-tag. In some embodiments, a polyhistidine tag is added by PCR (i.e., the PCR primers comprise a polyhistidine sequence).

In some embodiments, a fusion peptide disclosed herein further comprises at least one protein tag. In some embodiments, a fusion peptide disclosed herein comprises an epitope tag. In some embodiments, a fusion peptide disclosed herein further comprises a V5 epitope tag. In some embodiments, the V5 tag comprises the amino acids: GKPIPNPLLGLDST (SEQ ID NO:4). In some embodiments, the V5 tag comprises the amino acids: IPNPLLGLD (SEQ ID NO:5). In some embodiments, a V5 tag is added to a fusion protein disclosed herein by any suitable method. In some embodiments, a TAT-Myc polypeptide sequence is cloned into an expression vector encoding a V5 tag. In some embodiments, a V5 tag is added by PCR (i.e., the PCR primers comprise a V5 sequence).

In some embodiments, the amino acids are in the D formation. In some embodiments, the amino acids are in the L formation. In some embodiments, a first plurality of amino acids are in the D formation and a second plurality are in the L formation.

In some embodiments, the MYC Increasing Agent comprises SEQ ID NO. 2:

MRKKRRQRRRMDFFRVVENQQPPATMPLNVSFTNRNYDLDYDSVQPY

FYCDEEENFYQQQQQSELQPPAPSEDIWKKFELLPTPPLSPSRRSGL

CSPSYVAVTPFSLRGDNDGGGGSFSTADQLEMVTELLGGDMVNQSFI

CDPDDETFIKNIIIQDCMWSGFSAAAKLVSEKLASYQAARKDSGSPN

PARGHSVCSTSSLYLQDLSAAASECIDPSVVFPYPLNDSSSPKSCAS

QDSSAFSPSSDSLLSSTESSPQGSPEPLVLHEETPPTTSSDSEEEQE

DEEEIDVVSVEKRQAPGKRSESGSPSAGGHSKPPHSPLVLKRCHVST

HQHNYAAPPSTRKDYPAAKRVKLDSVRVLRQISNNRKCTSPRSSDTE

ENVKRRTHNVLERQRRNELKRSFFALRDQIPELENNEKAPKVVILKK

ATAYILSVQAEEQKLISEEDLLRKRREQLKHKLEQLRKGELNSKLEG

KPIPNPLLGLDSTRTGHHHHHH.

Construction of a MYC-TAT Peptide

In some embodiments, a MYC-TAT fusion peptide disclosed herein is constructed by any suitable method. In some embodiments, a nucleotide sequence encoding a MYC-TAT fusion peptide is generated by PCR. In some embodiments, a forward primer for a human MYC sequence comprises an in frame N-terminal 9-amino-acid sequence of the TAT protein transduction domain (i.e., RKKRRQRRR). In some embodiments, a reverse primer for a human MYC sequence is designed to remove the stop codon. In some embodiments, the PCR product is cloned into any suitable expression vector (hereinafter, p-TAT-MYC). In some embodiments, the expression vector comprises a polyhistidine tag and a V5 tag.

Assays for the Identification of Agents

Reversal of Anergy

Disclosed herein, in certain embodiments, is a method of identifying an agent that reverses anergy in a B-cell. In certain instances, an agent that reverses anergy in a B-cell increases an immune response and/or increases the viability of a cell. In certain instances, an agent that reverses anergy in a B-cell up-regulates MYC (e.g. a MYC gene and/or a Myc polypeptide).

In some embodiments, a method of identifying an agent that reverses anergy in a B-cell comprises (a) contacting a plurality of anergic B-cells with an agent; and (b) following contacting the plurality of cells with the agent, detecting and/or measuring the level of expression of one or more cell surface markers (e.g. cell surface markers the presence of which is indicative a non-anergic cell) in the cell culture. In some embodiments, the cell surface marker is IgM, IgMa, IgMb, B220, CD21/35, CD23, CD24 (HSA), CD40, CD69, CD80 and/or CD86 (B7-2).

In certain instances, the expression of IgM, IgMa, IgMb, B220, CD21/35, CD23, CD24 (HSA), CD40, CD69, CD80 and/or CD86 (B7-2) is down-regulated in anergic B-cells when compared to non-anergic B-cells. In certain instances, reversing (e.g. partially or fully) anergy results in an increase in the expression of IgM, IgMa, IgMb, B220, CD21/35, CD23, CD24 (HSA), CD40, CD69, CD80 and/or CD86 (B7-2).

In some embodiments, a method of identifying an agent that reverses anergy in a B-cell comprises identifying an agent as an agonist of an immune response if expression of a cell surface marker is upregulated (e.g. as compared to an anergic B-cell not contacted with an agent). In some embodiments, expression of a cell surface marker is upregulated on activated B-cells (when compared to the expression pattern on anergic B-cells) by about 10% to about 100% (e.g. at least 10%, 15%, 20%, 25%, 30%, 35%, 40%, 45%, 50%, 55%, 60%, 65%, 70%, 75%, 80%, 85%, 86%, 87%, 88%, 90%, 91%, 92%, 94%, 95%, 96%, 97%, 98%, or any other percent from about 10% to about 100%). In some embodiments, expression of a cell surface marker is upregulated on activated B-cells (when compared to the expression pattern on anergic B-cells) by about 30% to about 100% (e.g. at least 30%, 35%, 40%, 45%, 50%, 55%, 60%, 65%, 70%, 75%, 80%, 85%, 86%, 87%, 88%, 90%, 91%, 92%, 94%, 95%, 96%, 97%, 98%, or any other percent from about 30% to about 100%). In some embodiments, expression of a cell surface marker is upregulated on activated B-cells (when compared to the expression pattern on anergic B-cells) by about 50% to about 100% (e.g. at least 50%, 55%, 60%, 65%, 70%, 75%, 80%, 85%, 86%, 87%, 88%, 90%, 91%, 92%, 94%, 95%, 96%, 97%, 98%, or any other percent from about 50% to about 100%). In some embodiments, expression of a cell surface marker is upregulated on activated B-cells (when compared to the expression pattern on anergic B-cells) by about 70% to about 100% (e.g. at least 70%, 75%, 80%, 85%, 86%, 87%, 88%, 90%, 91%, 92%, 94%, 95%, 96%, 97%, 98%, or any other percent from about 70% to about 100%). In some embodiments, expression of a cell surface marker is upregulated on activated B-cells (when compared to the expression pattern on anergic B-cells) by about 80% to about 100% (e.g. at least 80%, 85%, 86%, 87%, 88%, 90%, 91%, 92%, 94%, 95%, 96%, 97%, 98%, or any other percent from about 80% to about 100%).

In some embodiments, a method of identifying an agent that reverses anergy in a B-cell comprises identifying an agent as an antagonist of an immune response if expression of a cell surface marker is downregulated (e.g. as compared to a non-anergic B-cell not contacted with an agent). In some embodiments, expression of a cell surface marker is downregulated (e.g. as compared to a non-anergic B-cell not contacted with an agent) by about 10% to about 100% (e.g. at least 10%, 15%, 20%, 25%, 30%, 35%, 40%, 45%, 50%, 55%, 60%, 65%, 70%, 75%, 80%, 85%, 86%, 87%, 88%, 90%, 91%, 92%, 94%, 95%, 96%, 97%, 98%, or any other percent from about 10% to about 100%). In some embodiments, expression of a cell surface marker is downregulated (e.g. as compared to a non-anergic B-cell not contacted with an agent) by about 30% to about 100% (e.g. at least 30%, 35%, 40%, 45%, 50%, 55%, 60%, 65%, 70%, 75%, 80%, 85%, 86%, 87%, 88%, 90%, 91%, 92%, 94%, 95%, 96%, 97%, 98%, or any other percent from about 30% to about 100%). In some embodiments, expression of a cell surface marker is downregulated (e.g. as compared to a non-anergic B-cell not contacted with an agent) by about 50% to about 100% (e.g. at least 50%, 55%, 60%, 65%, 70%, 75%, 80%, 85%, 86%, 87%, 88%, 90%, 91%, 92%, 94%, 95%, 96%, 97%, 98%, or any other percent from about 50% to about 100%). In some embodiments, expression of a cell surface marker is downregulated (e.g. as compared to a non-anergic B-cell not contacted with an agent) by about 70% to about 100% (e.g. at least 70%, 75%, 80%, 85%, 86%, 87%, 88%, 90%, 91%, 92%, 94%, 95%, 96%, 97%, 98%, or any other percent from about 70% to about 100%). In some embodiments, expression of a cell surface marker is downregulated (e.g. as compared to a non-anergic B-cell not contacted with an agent) by about 80% to about 100% (e.g. at least 80%, 85%, 86%, 87%, 88%, 90%, 91%, 92%, 94%, 95%, 96%, 97%, 98%, or any other percent from about 80% to about 100%).

In some embodiments, a method of identifying an agent that reverses anergy in a B-cell further comprises comparing (1) the level of expression of the cell surface marker observed in a plurality of anergic B-cells following contacting the plurality of cells with the agent to (2) the level of cell surface marker observed in a control. In some embodiments, the control is a plurality of anergic B-cells not contacted with an agent.

In some embodiments, a method of identifying an agent that reverses anergy in a B-cell comprises obtaining an anergic B-cell from any suitable source (e.g. a human, a mouse, a rat, or any mammal). In some embodiments, a method of identifying an agent that reverses anergy in a B-cell comprises obtaining an anergic B-cell from transgenic mice with the phenotype $BCR^{HEL}/sHEL$. In certain instances, $BCR^{HEL}$ mice express a mature B-cell receptor (BCR) for the antigen hen egg lysozyme (HEL). In certain instances, the HEL BCR is the dominant BCR on the B-cells of the transgenic mice. In certain instances, sHEL mice ubiquitously express a transgene for the soluble form of HEL. In certain instances, the expression of the HEL transgene is operably linked to a metallothionein promoter. In certain instances, the exposure to soluble HEL induces anergy in B-cells. U.S. Patent Application Pub. No. 2008/0070256 is hereby incorporated by reference for the methods of constructing the murine models discussed above. In some embodiments, the anergic B-cells are obtained from the spleen, thymus, bone marrow, lymph nodes, or combinations thereof of the transgenic mice.

In some embodiments, a method of identifying an agent that reverses anergy in a B-cell comprises detecting and/or measuring the level of expression of one or more cell surface markers (e.g. CD86). In some embodiments, detecting and/or measuring the level of expression of one or more cell surface markers comprises (a) contacting a plurality of anergic B-cells (e.g. a control, or a plurality of anergic B-cells following contact with an agent) with antibodies to a cell surface marker (e.g. antibodies to CD86); (b) washing the cell culture (e.g. rinsing) with buffer (e.g. FACS buffer) after contact with the antibodies; and (c) detecting and/or measuring the amount of antibody/cell surface marker complex. In some embodiments, the antibodies are purchased from a commercial supplier. In some embodiments, the antibodies are generated in-house. For methods of generating antibodies, see Kohler et al., Nature, 256:495 (1975); U.S. Pat. No. 4,816,567; or Goding, Monoclonal Antibodies: Principles and Practice (Academic Press, 1986); Ward et al., Nature 341: 544-546 (1989); Huse et al., Science 246: 1275-1281 (1989); McCafferty et al., Nature 348: 552-554 (1990); Clackson et al., Nature, 352:624-628 (1991) Marks et al., J. Mol. Biol., 222:581-597 (1991) all of which are hereby incorporated by reference. In some embodiments, the cell culture is incubated on ice during the contact with the antibodies. In some embodiments, the antibody is isotopically-labeled, radio-labeled, fluorophore-labeled, or biotinylated. In some embodiments, the fluorophore is fluorescein. In certain instances, the cell surface marker/antibody complex is detectable and/or measurable in any suitable manner (e.g. HPLC, fluorescence microscopy, confocal microscopy, microarray scanners, Surface Plasmon Resonance, infrared spectroscopy, or autoradiography).

In some embodiments, a method of identifying an agent that reverses anergy in a B-cell comprises detecting and/or measuring the level of expression of IgM. In some embodiments, detecting and/or measuring the level of expression of IgM comprises (a) contacting a cell culture (e.g. a control, or a plurality of anergic B-cells following contact with an agent) with an antigen (e.g. HEL) for a period of time sufficient to allow the antigen to bind to an IgM; (b) washing the cell culture (e.g. rinsing) with buffer (e.g. FACS buffer) after contacting the culture with the antigen; and (c) detecting and/or measuring the amount of antigen and/or antigen/IgM complex. In some embodiments, the antigen is biotinylated. In some embodiments, the cell culture is further incubated with a marker having an affinity for biotin (the "Biotin Marker"). In some embodiments, the Biotin Marker is avidin or streptavidin. In some embodiments, the Biotin Marker is isotopically-labeled, radio-labeled, fluorophore-labeled. In some embodiments, the fluorophore is phycoerythrin. In certain instances, the IgM/antigen/Biotin Marker complex is detectable and/or measurable in any suitable manner (e.g. HPLC, fluorescence microscopy, confocal microscopy, microarray scanners, Surface Plasmon Resonance, infrared spectroscopy, or autoradiography).

In some embodiments, a method of identifying an agent that reverses anergy in a B-cell comprises detecting and/or measuring the level of expression of IgM. In some embodiments, detecting and/or measuring the level of expression of IgM comprises (a) contacting a cell culture (e.g. a control, or a plurality of anergic B-cells following contact with an agent) with an antigen (e.g. HEL) for a period of time sufficient to allow the antigen to bind to the IgM; (b) washing the cell culture (e.g. rinsing) with buffer (e.g. FACS buffer) after contacting the culture with the antigen; and (c) detecting and/or measuring the amount of antigen and/or antigen/IgM complex. In some embodiments, the culture is contacted with dilutions of antibodies to the antigen (e.g. for a period of time sufficient to allow the antibodies to bind to the antigen). In some embodiments, the cell culture is incubated on ice during contact with the antibodies. In some embodiments, the cell culture is washed (e.g. rinsed) with buffer (e.g. FACS buffer) after contact with the antibodies. In some embodiments, the antibody is isotopically-labeled, radio-labeled, fluorophore-labeled, or biotinylated. In some embodiments, the fluorophore is fluorescein. In certain instances, the antigen/antibody and/or IgM/antigen/antibody complex is detectable and/or measurable in any suitable manner (e.g. HPLC, fluorescence microscopy, confocal microscopy, microarray scanners, Surface Plasmon Resonance, infrared spectroscopy, or autoradiography).

In some embodiments, the method further comprises detecting the presence of and/or measuring the amount of the labeled antibody, or of a complex formed between the antibody and the HEL antigen. In certain instances, the HEL antigen/antibody complex is detectable and measurable in any suitable manner (e.g. HPLC, fluorescence microscopy, confocal microscopy, microarray scanners, Surface Plasmon Resonance, infrared spectroscopy, or autoradiography).

Modulation of Cytokine Function

Disclosed herein, in certain embodiments, is a method of identifying an agent that induces (e.g., activates, increases, or supplements) an immune response. In some embodiments, the method comprises identifying an agent that replaces and/or augments cytokine function (the "Cytokine Supplementing Agent"). In certain instances, an agent that replaces and/or augments cytokine function in a factor-dependent cell increases an immune response and/or increases the viability of a cell. In certain instances, an agent that replaces and/or augments cytokine function in a factor-dependent cell up-regulates MYC (e.g. a MYC gene and/or a Myc polypeptide).

In some embodiments, the method comprises (a) contacting a plurality of factor-dependent cells with an agent; and (b) following contacting the cell with the agent, detecting and/or measuring the level of expansion of the cell culture.

In some embodiments, the method further comprises identifying an agent as a Cytokine Supplementing Agent if, following contact with the agent, the cell culture expands (e.g. as compared to a cell culture not contacted with an agent). In some embodiments, following contact with the agent the cell culture expands (when compared to a cell culture not contacted with an agent) by about 10% to about 100% (e.g. at least 10%, 15%, 20%, 25%, 30%, 35%, 40%, 45%, 50%, 55%, 60%, 65%, 70%, 75%, 80%, 85%, 86%, 87%, 88%, 90%, 91%, 92%, 94%, 95%, 96%, 97%, 98%, or any other percent from about 10% to about 100%). In some embodiments, following contact with the agent the cell culture expands (when compared to a cell culture not contacted with an agent) by about 30% to about 100% (e.g. at least 30%, 35%, 40%, 45%, 50%, 55%, 60%, 65%, 70%, 75%, 80%, 85%, 86%, 87%, 88%, 90%, 91%, 92%, 94%, 95%, 96%, 97%, 98%, or any other percent from about 30% to about 100%). In some embodiments, following contact with the agent the cell culture expands (when compared to a cell culture not contacted with an agent) by about 50% to about 100% (e.g. at least 50%, 55%, 60%, 65%, 70%, 75%, 80%, 85%, 86%, 87%, 88%, 90%, 91%, 92%, 94%, 95%, 96%, 97%, 98%, or any other percent from about 50% to about 100%). In some embodiments, following contact with the agent the cell culture expands (when compared to a cell culture not contacted with an agent) by about 70% to about 100% (e.g. at least 70%, 75%, 80%, 85%, 86%, 87%, 88%, 90%, 91%, 92%, 94%, 95%, 96%, 97%, 98%, or any other percent from about 70% to about 100%). In some embodiments, following contact with the agent the cell culture expands (when compared to a cell culture not contacted with an agent) by about 80% to about 100% (e.g. at least 80%, 85%, 86%, 87%, 88%, 90%, 91%, 92%, 94%, 95%, 96%, 97%, 98%, or any other percent from about 80% to about 100%).

In some embodiments, a method of identifying an agent that that replaces and/or augments cytokine function further comprises comparing (1) the level of expansion observed in a plurality of factor-dependent cells following contacting the plurality of cells with an agent to (2) the level of expansion of a control. In some embodiments, the control is a plurality of factor-dependent cells not contacted with an agent.

In some embodiments, contacting a factor-dependent cell with an agent that replaces and/or augments cytokine function results in the expression of MYC being upregulated. In certain instances, the up-regulation of MYC results in factor-dependent cells that do not require a cytokine for viability. In certain instances, the up-regulation of MYC results in factor-dependent cells that proliferate in the absence of a cytokine. In certain instances, the up-regulation of MYC results in factor-dependent cells that do not undergo apoptosis in the absence of a cytokine.

In some embodiments, the factor-dependent cells are lymphoid cells (i.e. derived from cells of the lymphatic system). In some embodiments, the factor-dependent cells is, by way of non-limiting example, IL-2−/−, IL-3−/−, IL-4−/−, IL-5−/−, IL-6−/−, IL-7−/−, IL-8−/−, IL-9−/−, IL-10−/−, IL-11−/−, IL-12−/−, or any combinations thereof. In some embodiments, the factor-dependent cells are derived from a cell line selected from, by way of non-limiting example: 2D6; 2E8; 10B10; ATH8; B13; BAF/3; BALM-4; BCL1; CT.4S; CT6; CTL44; CTLL-2; D1; D10; D36; Da; DS-1; Ea3.17; EL4; FL5.12; HT-2; IC-2; Kitt225; KT-3; L4; L138.8A; LBRM-33; LyD9; MC/9; MLA-144; Mono Mac 6; Nb2; NKC3; PB-1; Pno; PT-18; Ramos; Sez627; T10; T88; T1165; TALL-103; TF-1; TMD2; TS1; UT-7; XG-1; Y16; or a combination thereof. In some embodiments, the cells are derived from CTLL-2; or BAF/3 cell lines.

Disclosed herein, in certain embodiments, are methods of identifying an agent that inhibits and/or interferes with cytokine function (the "Cytokine Interfering Agent"). In certain instances, a Cytokine Interfering Agent decreases an immune response and/or decreases the viability of a cell. In some embodiments, the method comprises (a) contacting a plurality of factor-dependent cells with a required growth factor such that the cell culture expands; (b) contacting the plurality of cells plurality of factor-dependent cells with an agent; and (c) following contacting the plurality of cells plurality of factor-dependent cells with the agent, detecting and/or measuring the level of expansion of the cell culture.

In some embodiments, the method further comprises identifying an agent as cytokine interfering agent if, following contact with the agent, the cell culture contracts (e.g. as compared to a cell culture not contacted with an agent). In some embodiments, following contact with the agent the cell culture contracts (when compared to a cell culture not contacted with an agent) by about 10% to about 100% (e.g. at least 10%, 15%, 20%, 25%, 30%, 35%, 40%, 45%, 50%, 55%, 60%, 65%, 70%, 75%, 80%, 85%, 86%, 87%, 88%, 90%, 91%, 92%, 94%, 95%, 96%, 97%, 98%, or any other percent from about 10% to about 100%). In some embodiments, following contact with the agent the cell culture contracts (when compared to a cell culture not contacted with an agent) by about 30% to about 100% (e.g. at least 30%, 35%, 40%, 45%. 50%, 55%, 60%, 65%, 70%, 75%, 80%, 85%, 86%, 87%, 88%, 90%, 91%, 92%, 94%, 95%, 96%, 97%, 98%, or any other percent from about 30% to about 100%). In some embodiments, following contact with the agent the cell culture contracts (when compared to a cell culture not contacted with an agent) by about 50% to about 100% (e.g. at least 50%, 55%, 60%, 65%, 70%, 75%, 80%, 85%, 86%, 87%, 88%, 90%, 91%, 92%, 94%, 95%, 96%, 97%, 98%, or any other percent from about 50% to about 100%). In some embodiments, following contact with the agent the cell culture contracts (when compared to a cell culture not contacted with an agent) by about 70% to about 100% (e.g. at least 70%, 75%, 80%, 85%, 86%, 87%, 88%, 90%, 91%, 92%, 94%, 95%, 96%, 97%, 98%, or any other percent from about 70% to about 100%). In some embodiments, following contact with the agent the cell culture contracts (when compared to a cell culture not contacted with an agent) by about 80% to about 100% (e.g. at least 80%, 85%, 86%, 87%, 88%, 90%, 91%, 92%, 94%, 95%, 96%, 97%, 98%, or any other percent from about 80% to about 100%).

In some embodiments, a method of identifying an agent that that replaces and/or augments cytokine function further comprises comparing (1) the level of expansion observed in a plurality of factor-dependent cells following contacting the plurality of cells with an agent to (2) the level of expansion of a control. In some embodiments, the control is a plurality of factor-dependent cells not contacted with an agent.

In some embodiments, contacting a factor-dependent cell with an agent that inhibits and/or interferes with cytokine function results in the expression of MYC being down-regulated. In certain instances, the down-regulation of MYC results in factor-dependent cells that require a cytokine for viability. In certain instances, the down-regulation of MYC results in factor-dependent cells that do not proliferate in the absence of a cytokine. In certain instances, the down-regulation of MYC results in factor-dependent cells that undergo apoptosis in the absence of a cytokine.

In some embodiments, the factor-dependent cells are lymphoid cells (i.e. derived from cells of the lymphatic system). In some embodiments, the factor-dependent cells is, by way of non-limiting example, IL-2−/−, IL-3−/−, IL-4−/−, IL-5−/−, IL-6−/−, IL-7−/−, IL-8−/−, IL-9−/−, IL-10−/−, IL-11−/−, IL-12−/−, or any combinations thereof. In some embodiments, the factor-dependent cells are derived from a cell line selected from, by way of non-limiting example: 2D6; 2E8; 10B10; ATH8; B13; BAF/3; BALM-4; BCL1; CT.4S; CT6; CTL44; CTLL-2; D1; D10; D36; Da; DS-1; Ea3.17; EL4; FL5.12; HT-2; IC-2; Kitt225; KT-3; L4; L138.8A; LBRM-33; LyD9; MC/9; MLA-144; Mono Mac 6; Nb2; NKC3; PB-1; Pno; PT-18; Ramos; Sez627; T10; T88; T1165; TALL-103; TF-1; TMD2; TS1; UT-7; XG-1; Y16; or a combination thereof. In some embodiments, the cells are derived from CTLL-2; or BAF/3 cell lines.

Reporter Assay

Disclosed herein, in certain embodiments, is a method of identifying an agent that induces (e.g., activates, increases, or supplements) an immune response. In some embodiments, the method comprises identifying an agent that modulates the function of a MYC encoded transcription factor. In some embodiments, the method comprises (a) transforming a plurality of cells in a cell culture with a reporter construct, wherein the reporter construct is a plasmid that comprises a reporter gene, and wherein the expression of the reporter gene is operably linked to one or more E-box sequences; (b) contacting the plurality of cells plurality of cells transformed with the reporter construct with an agent; and (c) following contacting the culture with an agent, detecting and/or measuring the level of expression of the reporter gene. In some embodiments, the reporter construct is obtained in any suitable manner (e.g. purchased from a vendor or fabricated in-house). For methods suitable for fabricating a reporter construct and transforming cells with a reporter construct see Molecular Cloning: A Laboratory Manual, second edition (Sambrook et al., 1989) and Molecular Cloning: A Laboratory Manual, third edition (Sambrook and Russel, 2001), jointly referred to herein as "Sambrook"); Current Protocols in Molecular Biology (F. M. Ausubel et al., eds., 1987, including supplements through 2001); Current Protocols in Nucleic Acid Chemistry John Wiley & Sons, Inc., New York, 2000) which are hereby incorporated by reference for such disclosure.

In some embodiments, a method of identifying an agent that modulates the function of a MYC encoded transcription factor further comprises comparing (1) the level of expression of the reporter gene in a plurality of cells transformed with the reporter construct following contact with an agent to (2) the level of the level of expression of the reporter gene in a control.

In some embodiments, the cells are eukaryotic cells. In some embodiments, the eukaryotic cells are human cells. In some embodiments, the cells are human lymphoid cells. In some embodiments, the lymphoid cells are B-cells.

In some embodiments, the reporter construct comprises one or more E-box sequences upstream of a reporter gene. In some embodiments, the one or more E-box sequences are encoded in a myc-responsive promoter sequence and/or are upstream of the myc-responsive promoter. As used here, "promoter sequence" means a nucleotide sequence upstream of a gene that allows an RNA polymerase to transcribe the gene. As used herein, "myc-responsive promoter" means a promoter sequence to which a transcription factor encoded by MYC can bind. In some embodiments, the myc-responsive promoter is the ornithine decarboxylase promoter.

In some embodiments, the reporter gene is a β-galactosidase gene, a β-lactamase gene, a horseradish peroxidase gene, an alkaline phosphatase gene, a thymidine kinase gene, a xanthine phosphoribotransferase gene, a tyrosinase gene, a cytosine deaminase gene, an antibiotic resistance gene, or a gene having a fluorescent expression product. In some embodiments, the gene having a fluorescent expression product is a luciferase gene, or a green fluorescent polypeptide (GFP) gene.

In some embodiments, the method of identifying an agent that modulates the function of a MYC encoded transcription factor further comprises detecting the expression of and/or measuring the amount of expression of the reporter gene. In certain instances, the expression of the reporter gene is detectable and measurable in any suitable manner (e.g. fluorescence microscopy).

In some embodiments, the cell culture further comprises serum. In some embodiments, the serum is fetal bovine serum (FBS); bovine serum; horse serum; human serum; chicken serum; goat serum; porcine serum; rabbit serum; sheep serum; a serum replacement (e.g. Serum Replacement 1(Sigma-Aldrich)); or a combination thereof. In some embodiments, the cell culture further comprises media. In some embodiments, the media is, by way of non-limiting example, phosphate buffered saline; Earle's Balanced Salts; Hanks' Balanced Salts; Tyrode's Salts; derivatives thereof; or combinations thereof. In some embodiments, the growth factor is, by way of non-limiting example, a cytokine, epidermal growth factor, or platelet-derived growth factor. In some embodiments, the cytokine is, by way of non-limiting example, IL-2, IL-3, IL-4, IL-5, IL-6, IL-7, IL-8, IL-9, IL-10, IL-11, IL-12, or IL-13. In certain instances, the choice of growth factor is determined based on the type of cell used in the method.

In some embodiments, the method further comprises contacting the plurality of cells with a mitogenic stimulant. In some embodiments, the mitogenic stimulant is, by way of non-limiting example, an antigen, or a mitogenic antibody. In some embodiments, the antigen is, by way of non-limiting example, phytohaemagglutinin (PHA), concanavalin A (conA), lipopolysaccharide (LPS), pokeweed mitogen (PWM), or combinations thereof. In some embodiments, the mitogenic antibody is, by way of non-limiting example, an anti-IgM, an anti-CD40, or combinations thereof. In some embodiments, the anti-IgM is anti-IgM-F(ab')2. In some embodiments, the anti-CD40 is anti-CD40 IgM.

In Vitro Validation of Agents

In some embodiments, any of the methods described herein further comprise validating in vitro an agent (e.g. an agent identified according to any method described herein) as a regulator of an immune response. In some embodiments, a method of validating in vitro an agent as a regulator of an immune response comprises (a) contacting the agent with a primary T-cell activation culture; (b) staining the culture for activation markers; and (c) staining the culture 24 hours after contact with the agent. In certain instances, the cell viability is detectable and measurable in any suitable manner (e.g. fluorescence microscopy, flow cytometry, FACS). In certain instances, an agent that up-regulates an immune response will cause an increase in activation markers as compared to a control (or the culture before contact with the agent). In certain instances, an agent that down-regulates an immune response will cause a decrease in activation markers as compared to a control (or the culture before contact with the agent).

In some embodiments, any of the methods described herein further comprise validating in vitro an agent as a regulator of an immune response. In some embodiments, a method of validating in vitro an agent as a regulator of an immune response comprises (a) contacting the agent with a primary T-cell activation culture; (b) staining the culture with CFSE (carboxyfluorescein succinimidyl ester); and (c) staining the culture 72 hours after contact with the agent. In certain instances, CFSE indicates cell proliferation. In certain instances, a cell incorporates the CFSE. In certain instances, a portion (i.e. half) of the CFSE in a cell transfers to a daughter cell following division. In certain instances, the amount of CFSE in cell decreases with each division. In certain instances, the cell viability is detectable and measurable in any suitable manner (e.g. fluorescence microscopy, flow cytometry, FACS). In certain instances, an agent that up-regulates an immune response will cause an increase in cell proliferation as compared to a control (or the culture before contact with the agent). In certain instances, an agent that down-regulates an immune response will cause a decrease in cell proliferation as compared to a control (or the culture before contact with the agent).

In some embodiments, any of the methods described herein further comprise validating in vitro an agent as a regulator of an immune response. In some embodiments, a method of validating in vitro an agent as a regulator of an immune response comprises (a) contacting the agent with a primary T-cell activation culture; (b) staining the culture with 7AAD (7-amino-actinomycin D); and (c) staining the culture 72 hours after contact with the agent. In certain instances, 7-AAD indicates cell viability. In certain instances, 7-AAD will stain cells with compromised membranes (i.e. unviable cells). In certain instances, 7-AAD will not stain cells with uncompromised membranes (i.e. viable cells). In certain instances, the cell viability is detectable and measurable in any suitable manner (e.g. fluorescence microscopy, flow cytometry, FACS). In certain instances, an agent that up-regulates an immune response will cause an increase in cell viability as compared to a control (or the culture before contact with the agent). In certain instances, an agent that down-regulates an immune response will cause a decrease in cell viability as compared to a control (or the culture before contact with the agent).

In Vivo Validation of Agents

In some embodiments, any of the methods described herein further comprise validating in vivo an agent (e.g. an agent identified according to any method described herein) as a regulator of an immune response. In some embodiments, a method of validating in vivo an agent as a regulator of an immune response comprises (a) immunizing a mammal (e.g. a mouse, rat, rabbit) against an antigen (e.g. OVA peptides, NP-KHL) by administering the antigen to a mouse; (b) administering the agent to the mouse before, during, or after administration of the antigen; (c) obtaining a biological sample (e.g. blood, lymph, or serum) from the mouse after administration of the antigen and agent; and (d) detecting or measuring an immune response (e.g. the rate of proliferation of memory B-cells and/or T-cells). In some embodiments, an immune response is detected or measured by detecting and measuring antibody production following the immunization. In some embodiments, antibody production is assayed once-a-day every day for a week following immunization and then once-a-week thereafter. In some embodiments, an immune response is detected or measured by detecting and measuring T-cell proliferation upon re-stimulation with the antigen. In some embodiments, T-cell proliferation is assayed one week after immunization. In certain instances, an agent that up-regulates a primary immune response will cause an increase in antibody production and T-cell proliferation as compared to a control (i.e. a mouse not administered the agent). In certain instances, an agent that down-regulates a primary immune response will cause a decrease in antibody production and T-cell proliferation as compared to a control (i.e. a mouse not administered the agent).

In some embodiments, any of the methods described herein further comprise validating in vivo an agent (e.g. an agent identified according to any method described herein) as a regulator of an immune response. In some embodiments, a method of validating in vivo an agent as a regulator of an immune response comprises (a) immunizing a mouse against an antigen (e.g. OVA peptides, NP-KHL) by administering the antigen to the mouse; (b) administering the agent to the mouse before, during, or after administration of the antigen; (c) challenging the mouse with the antigen 3 to 6 months after inoculation; (d) obtaining a biological sample (e.g. blood, lymph, or serum) from the mouse following the challenge; and (d) detecting or measuring an immune response. In some embodiments, an immune response is detected or measured by detecting and measuring antibody production following immunization. In some embodiments, antibody production is assayed once-a-day every day for a week following challenge and then once-a-week thereafter. In some embodiments, an immune response is detected or measured by detecting and measuring T-cell proliferation upon re-stimulation with the antigen. In some embodiments, T-cell proliferation is assayed one week after challenge. In certain instances, an agent that up-regulates a secondary immune response will cause an accelerated immune response (i.e. an increase rate of antibody production and T-cell proliferation) following challenge with the antigen as compared to a control (i.e. a mouse not administered the agent). In certain instances, an agent that down-regulates a secondary immune response will cause a decelerated immune response (i.e. a decreased rate of antibody production and T-cell proliferation) following challenge with the antigen as compared to a control (i.e. a mouse not administered the agent).

Agents

Disclosed herein, in certain embodiments, are agents that modulate an immune response (e.g. agents that reverse anergy, agents that modulate cytokine function, and/or agents that modulate the function of a MYC encoded transcription factor). In certain embodiments, the agent is useful in administration to an individual in need thereof. In specific embodiments, the agent is any agent identified by any of the methods disclosed herein. In some embodiments, the agent is any agent that modulates an immune response. In some embodiments, the agent is a small molecule. In some embodiments, the agent is RNAi. In some embodiments, the agent is an agonist of MYC (e.g. a MYC gene and/or a Myc polypeptide). In some embodiments, the agent is an antagonist of MYC (e.g. a MYC gene and/or a Myc polypeptide).

In some embodiments, the agent is identified as an agent that modulates the viability of a cell based on the agent's ability to reverse anergy in a B-cell. In some embodiments, the agent is identified as an agent that that modulates the viability of a cell based on the agent's ability to modulate the viability of factor-dependent cells. In some embodiments, the agent is identified as an agent that modulates the viability of a cell based on the agent's ability to induce expression of a reporter gene.

In some embodiments, the modulation of the immune response comprises the modulation of the viability of a lymphocyte. In some embodiments, the lymphocyte is a T-cell. In some embodiments, the T-cell is a CD4+ T-cell. In some embodiments, the T-cell is a memory T-cell.

In some embodiments, the viability of a lymphocyte following contact with the agent is more than 1 to about 10 times greater than the viability of a lymphocyte that has not been contacted the agent. In some embodiments, the agent causes the up-regulation of a MYC gene in a lymphocyte. In some embodiments, the modulation occurs in vivo. In some embodiments, the lymphocyte is a T-cell. In some embodiments, the T-cell is a memory T-cell. In certain instances, the up-regulation of a MYC gene results in an extended life-span for the T-cell. In certain instances, the extended life span of a memory T-cell results in a higher concentration of memory T-cells in a body. In certain instances, the higher concentration of memory T-cells results in an accelerated primary immune response to antigen. In certain instances, the up-regulation of a MYC gene results in a decrease in anergic T-cells. In certain instances, the decrease in anergic T-cells results in an accelerated primary immune response to antigen. In certain instances, the up-regulation of a MYC gene results in a decrease in the time it takes a T-cell to activate in response to an antigen. In certain instances, the decrease in the time it takes a T-cell to activate in response to an antigen results in an accelerated primary immune response to antigen.

In some embodiments, the agent is administered before, during, or after administration of a vaccine to an individual. In some embodiments, the agent stimulates the immune system and increases the response of the immune system to a vaccine. In some embodiments, agent augments an immune response. In some embodiments, the agent acts synergistically with the vaccine. In some embodiments, the agent is a vaccine adjuvant.

In some embodiments, a vaccine comprises dead microorganisms, attenuated microorganisms, toxoids, subunits of the pathogen, nucleic acids, or combinations thereof. In some embodiments, the vaccine is a vaccine for hepatitis A; hepatitis B; polio; measles; mumps; rubella; diphtheria; pertussis; tetanus; influenza; varicella zoster virus; rotavirus; influenza; meningococcal disorder; pneumonia; smallpox; cholera; bubonic plague; yellow fever; tuberculosis: human paplomavirus; or combinations thereof. In some embodiments, the vaccine is a vaccine for a cancer (e.g. follicular B-cell Non-Hodgkin's lymphoma, prostate cancer, multiple myeloma, kidney cancer, cutaneous melanoma, ocular melanoma, and other solid tumors, carcinomas and sarcomas). In some embodiments, a cancer vaccine is a patient-specific vaccine (e.g. the vaccine comprises a patient's own tumor cells). In some embodiments, a cancer vaccine comprises Prostate Specific Antigen (PSA). In some embodiments, a cancer vaccine comprises sialyl Tn (STn). In some embodiments, a cancer vaccine comprises Heat Shock Proteins (HSPs) (e.g., gp96). In some embodiments, a cancer vaccine comprises ganglioside molecules (e.g., GM2, GD2, and GD3). In some embodiments, a cancer vaccine comprises carcinoembryonic antigen (CEA). In some embodiments, a cancer vaccine comprises MART-1 (also known as Melan- A). In some embodiments, a cancer vaccine comprises tyrosinase. In some embodiments, the vaccine is a DNA vaccine.

In some embodiments, the comprises an antigenic moiety. In some embodiments, the antigenic moiety is a toxoid, a peptide, a nucleic acid sequence, a polysaccharide, or a combination thereof. In some embodiments, the antigenic moiety is derived from a pathogen selected from: hepatitis A; hepatitis B; polio; measles; mumps; rubella; diphtheria; pertussis; tetanus; influenza; varicella zoster virus; rotavirus; meningococcal; pneumonia; smallpox; cholera; bubonic plague; yellow fever; tuberculosis; human papillomavirus; or combinations thereof. In some embodiments, the antigenic moiety is derived a neoplastic cell. In some embodiments, the antigenic moiety is a nucleic acid or a polymer of nucleic acids.

In certain instances, up-regulating an immune response in an individual receiving vaccination against an antigen results in an increase in the viability and thus concentration of memory T-cells against that antigen. In certain instances, up-regulating an immune response in an individual receiving vaccination against an antigen results in accelerated activation of the T-cell by the antigen. In certain instances, up-regulating an immune response in an individual receiving vaccination against an antigen results in a decrease in T-cells tolerant of the antigen.

In some embodiments, the viability of a lymphocyte administered the agent is more than 1 to about 25 times less than the viability of a lymphocyte that has not been administered the agent. In some embodiments, the agent causes the down-regulation of a MYC gene in a lymphocyte. In some embodiments, the modulation occurs in vivo. In some embodiments, the lymphocyte is a T-cell. In some embodiments, the T-cell is a memory T-cell. In certain instances, the down-regulation of a MYC gene results in a decreased life-span for the T-cell. In certain instances, the decreased life span of a memory T-cell results in a lower concentration of memory T-cells in a body. In certain instances, the lower concentration of memory T-cells results in a decelerated primary immune response to antigen, treatment of an autoimmune disorder, and/or immunosuppression. In certain instances, the down-regulation of a MYC gene results in an increase in anergic T-cells. In certain instances, the increase in anergic T-cells results in a decelerated primary immune response to antigen, treatment of an autoimmune disorder, and/or immunosuppression. In certain instances, the down-regulation of a MYC gene results in an increase in the time it takes a T-cell to activate in response to an antigen. In certain instances, the increase in the time it takes a T-cell to activate in response to an antigen results in a decelerated primary immune response to antigen, treatment of an autoimmune disorder, and/or immunosuppression.

In some embodiments, the agent is administered to an individual with an autoimmune disorder. In some embodiments, the autoimmune disorder is Castleman's Disease, lupus, multiple sclerosis, scleroderma pigmentosa, Autoimmune Lymphoproliferative Syndrome (ALPS), myesthenia gravis, diabetes, asthma, rheumatoid arthritis, vitiligo, diGeorge's syndrome, Grave's disease, Crohn's disease, inflammatory bowel disease, colitis, orchitis, scleroderma pigmentosa, uveitis, Post-Transplant Lymphoproliferative Disease (PTLD), or Autoimmune Disease-Associated Lymphadenopathy (ADAL). In certain instances, down-regulating an immune response in an individual with an autoimmune disorder ameliorates and/or prevents an immune response against self antigens by the subject's immune system.

In some embodiments, the agent is administered to an individual that has received an organ transplant, or a bone marrow transplant. In certain instances, down-regulating an immune response in an individual that has received an organ or bone marrow transplant ameliorates and/or prevents an immune response against the transplanted organ or bone marrow by the subject's immune system.

Pharmaceutical Compositions

Disclosed herein, in certain embodiments, are compositions that modulate the immune system in an individual in need thereof, wherein the composition comprises a therapeutically-effective amount of an agent identified by any of the methods disclosed herein. In some embodiments, the agent is a small molecule. In some embodiments, the agent is RNAi. In some embodiments, the agent is a biological molecule (e.g., a peptide, a fusion peptide). In some embodiments, the agent is a fusion peptide disclosed herein. In some embodiments, the agent is a fusion peptide comprising (a) a transporter peptide sequence; and (b) a MYC sequence. In some embodiments, the agent is a fusion peptide of Formula (I):

transporter peptide sequence-MYC sequence.

In some embodiments, the agent is identified as an agent that modulates the viability of a cell based on the agent's ability to reverse anergy in a B-cell. In some embodiments, the agent is identified as an agent that that modulates the viability of a cell based on the agent's ability to modulate the viability of factor-dependent cells. In some embodiments, the agent is identified as an agent that modulates the viability of a cell based on the agent's ability to induce expression of a reporter gene.

In some embodiments, the modulation of the immune response comprises the modulation of the viability of a lymphocyte. In some embodiments, the lymphocyte is a T-cell. In some embodiments, the T-cell is a CD4+ T-cell. In some embodiments, the T-cell is a memory T-cell.

In some embodiments, the viability of a lymphocyte following contact with the agent is more than 1 to about 10 times greater than the viability of a lymphocyte that has not been contacted the agent. In some embodiments, the agent causes the up-regulation of a MYC gene in a lymphocyte. In some embodiments, the modulation occurs in vivo. In some embodiments, the lymphocyte is a T-cell. In some embodiments, the T-cell is a memory T-cell. In certain instances, the up-regulation of a MYC gene results in an extended life-span for the T-cell. In certain instances, the extended life span of a memory T-cell results in a higher concentration of memory T-cells in a body. In certain instances, the higher concentration of memory T-cells results in an accelerated primary immune response to antigen. In certain instances, the up-regulation of a MYC gene results in a decrease in anergic T-cells. In certain instances, the decrease in anergic T-cells results in an accelerated primary immune response to antigen. In certain instances, the up-regulation of a MYC gene results in a decrease in the time it takes a T-cell to activate in response to an antigen. In certain instances, the decrease in the time it takes a T-cell to activate in response to an antigen results in an accelerated primary immune response to antigen.

In some embodiments, the agent is administered before, during, or after administration of a vaccine to an individual. In some embodiments, the agent stimulates the immune system and increases the response of the immune system to a vaccine. In some embodiments, the agent augments an immune response. In some embodiments, the agent acts synergistically with the vaccine. In some embodiments, the agent is a vaccine adjuvant.

In some embodiments, a vaccine comprises dead microorganisms, attenuated microorganisms, toxoids, subunits of the pathogen, nucleic acids, or combinations thereof. In some embodiments, the vaccine is a vaccine for hepatitis A; hepatitis B; polio; measles; mumps; rubella; diphtheria; pertussis; tetanus; influenza; varicella zoster virus; rotavirus; influenza; meningococcal disease; pneumonia; smallpox; cholera; bubonic plague; yellow fever; tuberculosis: human paplomavirus; or combinations thereof. In some embodiments, the vaccine is a vaccine for a cancer (e.g. Follicular B-cell Non-Hodgkin's Lymphoma, prostate cancer, multiple myeloma, kidney cancer, cutaneous melanoma, and ocular melanoma). In some embodiments, a cancer vaccine is a patient-specific vaccine (e.g. the vaccine comprises a patient's own tumor cells). In some embodiments, a cancer vaccine comprises Prostate Specific Antigen (PSA). In some embodiments, a cancer vaccine comprises sialyl Tn (STn). In some embodiments, a cancer vaccine comprises Heat Shock Proteins (HSPs) (e.g., gp96). In some embodiments, a cancer vaccine comprises ganglioside molecules (e.g., GM2, GD2, and GD3). In some embodiments, a cancer vaccine comprises carcinoembryonic antigen (CEA). In some embodiments, a cancer vaccine comprises MART-1 (also known as Melan-A). In some embodiments, a cancer vaccine comprises tyrosinase. In some embodiments, the vaccine is a DNA vaccine.

In some embodiments, the comprises an antigenic moiety. In some embodiments, the antigenic moiety is a toxoid, a peptide, a nucleic acid sequence, a polysaccharide, or a combination thereof. In some embodiments, the antigenic moiety is derived from a pathogen selected from: hepatitis A; hepatitis B; polio; measles; mumps; rubella; diphtheria; pertussis; tetanus; influenza; varicella zoster virus; rotavirus; meningococcal; pneumonia; smallpox; cholera; bubonic plague; yellow fever; tuberculosis; human papillomavirus; or combinations thereof. In some embodiments, the antigenic moiety is derived a neoplastic cell. In some embodiments, the antigenic moiety is a nucleic acid or a polymer of nucleic acids.

In certain instances, up-regulating an immune response in an individual receiving vaccination against an antigen results in an increase in the viability and thus concentration of memory T-cells against that antigen. In certain instances, up-regulating an immune response in an individual receiving vaccination against an antigen results in accelerated activation of the T-cell by the antigen. In certain instances, up-regulating an immune response in an individual receiving vaccination against an antigen results in a decrease in T-cells tolerant of the antigen.

In some embodiments, the viability of a lymphocyte administered the agent is more than 1 to about 25 times less than the viability of a lymphocyte that has not been administered the agent. In some embodiments, the agent causes the down-regulation of a MYC gene in a lymphocyte. In some embodiments, the modulation occurs in vivo. In some embodiments, the lymphocyte is a T-cell. In some embodiments, the T-cell is a memory T-cell. In certain instances, the down-regulation of a MYC gene results in a decreased life-span for the T-cell. In certain instances, the decreased life span of a memory T-cell results in a lower concentration of memory T-cells in a body. In certain instances, the lower concentration of memory T-cells results in a decelerated primary immune response to antigen, treatment of an autoimmune disorder, and/or immunosuppression. In certain instances, the down-regulation of a MYC gene results in an increase in anergic T-cells. In certain instances, the increase in anergic T-cells results in a decelerated primary immune response to antigen, treatment of an autoimmune disorder, and/or immunosuppression. In certain instances, the down-regulation of a MYC gene results in an increase in the time it takes a T-cell to activate in response to an antigen. In certain instances, the increase in the time it takes a T-cell to activate in response to an antigen results in a decelerated primary immune response to antigen, treatment of an autoimmune disorder, and/or immunosuppression.

In some embodiments, the agent is administered to an individual with an autoimmune disorder. In some embodiments, the autoimmune disorder is Castleman's Disease, lupus, multiple sclerosis, scleroderma pigmentosa, Autoimmune Lymphoproliferative Syndrome (ALPS), myesthenia gravis, diabetes, asthma, rheumatoid arthritis, vitiligo, diGeorge's syndrome, Grave's disease, Crohn's disease, inflammatory bowel disease, colitis, orchitis, scleroderma pigmentosa, uveitis, Post-Transplant Lymphoproliferative Disease (PTLD), or Autoimmune Disease-Associated Lymphadenopathy (ADAL). In certain instances, down-regulating an immune response in an individual with an autoimmune disorder ameliorates and/or prevents an immune response against self antigens by the subject's immune system.

In some embodiments, the agent is administered to an individual that has received an organ transplant, or a bone marrow transplant. In certain instances, down-regulating an immune response in an individual that has received an organ or bone marrow transplant ameliorates and/or prevents an immune response against the transplanted organ or bone marrow by the subject's immune system.

Formulations of Pharmaceutical Compositions

In some embodiments, pharmaceutical compositions are formulated in a conventional manner using one or more physiologically acceptable carriers including, e.g., excipients and auxiliaries which facilitate processing of the active compounds into preparations which are suitable for pharmaceutical use. In certain embodiments, proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

A pharmaceutical composition, as used herein, refers to a mixture of a compound described herein, with other chemical components, such as carriers, stabilizers, diluents, dispersing agents, suspending agents, thickening agents, and/or excipients. In certain instances, the pharmaceutical composition facilitates administration of the compound to an individual or cell. In certain embodiments of practicing the methods of treatment or use provided herein, therapeutically effective amounts of compounds described herein are administered in a pharmaceutical composition to an individual having a disorder, disease, or condition to be treated. In specific embodiments, the individual is a human. As discussed herein, the therapeutic compounds described herein are either utilized singly or in combination with one or more additional therapeutic agents.

In some embodiments, the pharmaceutical formulations described herein are administered to an individual in any manner, including one or more of multiple administration routes, such as, by way of non-limiting example, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound described herein are optionally manufactured in a conventional manner, such as, by way of example only, by means of conventional mixing, dissolving, granulating, dragee-making, levigating, emulsifying, encapsulating, entrapping or compression processes.

In some embodiments, a pharmaceutical compositions described herein includes one or more agents described herein, as an active ingredient in free-acid or free-base form, or in a pharmaceutically acceptable salt form. In some embodiments, the compounds described herein are utilized as an N-oxide or in a crystalline or amorphous form (i.e., a polymorph). In certain embodiments, an active metabolite or prodrug of a compound described herein is utilized. In some situations, a compound described herein exists as tautomers. All tautomers are included within the scope of the compounds presented herein. In certain embodiments, a compound described herein exists in an unsolvated or solvated form, wherein solvated forms comprise any pharmaceutically acceptable solvent, e.g., water, ethanol, and the like. The solvated forms of the compounds presented herein are also considered to be disclosed herein.

A "carrier" includes, in some embodiments, a pharmaceutically acceptable excipient and is selected on the basis of compatibility with compounds disclosed herein, such as, compounds of any of Formulas I-V, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins1999).

Moreover, in some embodiments, the pharmaceutical compositions described herein are formulated as a dosage form. As such, in some embodiments, provided herein is a dosage form comprising a compound described herein, e.g., a compound of any of Formulas I-V, suitable for administration to an individual. In certain embodiments, suitable dosage forms include, by way of non-limiting example, aqueous oral dispersions, liquids, gels, syrups, elixirs, slurries, suspensions, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

The pharmaceutical solid dosage forms described herein optionally include an additional therapeutic compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In some aspects, using standard coating procedures, such as those described in *Remington's Pharmaceutical Sciences*, 20th Edition (2000), a film coating is provided around the formulation of the compound of any of Formula I-V. In one embodiment, a compound described herein is in the form of a particle and some or all of the particles of the compound are coated. In certain embodiments, some or all of the particles of a compound described herein are microencapsulated. In some embodiment, the particles of the compound described herein are not microencapsulated and are uncoated.

In some embodiments, the pharmaceutical composition described herein is in unit dosage forms suitable for single administration of precise dosages. In unit dosage form, the formulation is divided into unit doses containing appropriate quantities of one or more compound. In some embodiments, the unit dosage is in the form of a package containing discrete quantities of the formulation. Non-limiting examples are packaged tablets or capsules, and powders in vials or ampoules. Aqueous suspension compositions are optionally packaged in single-dose non-reclosable containers. In some embodiments, multiple-dose re-closeable containers are used. In certain instances, multiple dose containers comprise a preservative in the composition. By way of example only, formulations for parenteral injection are presented in unit dosage form, which include, but are not limited to, ampoules, or in multi-dose containers, with an added preservative.

In some embodiments, the agents and compositions described herein are administered before, during, or after administration of a vaccine. In some embodiments, the agents and compositions described herein are incorporated into a vaccine. In some embodiments, the agents and compositions stimulate the immune system and increase the response of the immune system to a vaccine. In some embodiments, the agents and compositions augment an immune response. In some embodiments, the agents and compositions act synergistically with the vaccine. In some embodiments, the agents and compositions are vaccine adjuvants. In some embodiments, the vaccine formulation comprises an antigen or antigenic moiety (e.g. a protein or polysaccharide from *B. pertussis, C. tetani, E. coli, C. diphtheriae, P. Aeruginosa, V. cholerae, H. influenzae, N. meningitidis, S. pneumoniae, N. gonorrhea*) and the agent. In some embodiments, the vaccine further comprises a carrier (e.g. water, saline, PBS), a preservative (e.g. thimerosal, 2-phenoxy ethanol, phenol, benzethonium chloride), a stabilizer (e.g. lactose, monosodium glutamate), an antibiotic, an antioxidant, a pH controlling agent, or combinations thereof.

Topical Formulations

In some embodiments, a MYC fusion polypeptide disclosed herein (e.g., TAT-MYC) is administered topically (i.e., the polypeptide is administered to the surface of the skin). In some embodiments, a MYC fusion polypeptide disclosed herein (e.g., TAT-MYC) is administered topically at the site of a vaccine injection. In certain instances, a localized antigen depot (i.e., a tissue depot formed by vaccine adjuvants (e.g., water-in-oil emulsions, or aluminum salts) that results in the slow and even release of an antigen) arises during vaccination with current approaches. In some embodiments, the transient upregulation of MYC in the resident lymphoid cells in the skin, near the site of the antigen depot, drives a more robust immune response, and yields a broader response in the context of relaxed tolerance to self antigens.

Any suitable formulation is utilized. In some embodiments, the MYC fusion polypeptide is formulated as a solution, a cream, a lotion, a gel, an ointment, a foam, a microemulsion, or a combination thereof. In some embodiments, the MYC fusion polypeptide is formulated for delivery via a transdermal patch.

Any suitable method of topical administration is utilized (e.g., electroporation, sonophoresis, chemical delivery, skin abrasion). In some embodiments, the MYC fusion polypeptide is formulated for chemical delivery (i.e., a chemical substance (e.g., PEG, ethanol, glycerol monolaurate, sodium dodecyl sulfate, phosphatidyl choline, or urea) is used to facilitate penetration of an active agent across the skin). In some embodiments, the MYC fusion polypeptide is formulated for delivery via electroporation (i.e., the permeablization of a barrier (e.g., the skin) via application of an electric current). In some embodiments, the MYC fusion polypeptide is formulated for delivery via sonophoresis (i.e., the permeablization of a barrier (e.g., the skin) via application of ultrasound).

Creams and Lotions

In some embodiments, a MYC fusion polypeptide disclosed herein (e.g., TAT-MYC) is formulated as a cream. In certain instances, creams are semisolid (e.g., soft solid or thick liquid) formulations that include a MYC fusion polypeptide disclosed herein (e.g., TAT-MYC) dispersed in an oil-in-water emulsion or a water-in-oil emulsion.

In some embodiments, a MYC fusion polypeptide disclosed herein (e.g., TAT-MYC) is formulated as a lotion. In certain instances, lotions are fluid emulsions (e.g., oil-in-water emulsions or a water-in-oil emulsions).

In some embodiments, the hydrophobic component of a lotion and/or cream is derived from an animal (e.g., lanolin, cod liver oil, and ambergris), plant (e.g., safflower oil, castor oil, coconut oil, cottonseed oil, menhaden oil, palm kernel oil, palm oil, peanut oil, soybean oil, rapeseed oil, linseed oil, rice bran oil, pine oil, sesame oil, or sunflower seed oil), petroleum (e.g., mineral oil, or petroleum jelly), or a combination thereof.

Ointments

In some embodiments, a MYC fusion polypeptide disclosed herein (e.g., TAT-MYC) is formulated as an ointment. In certain instances, ointments are semisolid preparations that soften or melt at body temperature.

Pastes

In some embodiments, a MYC fusion polypeptide disclosed herein (e.g., TAT-MYC) is formulated as a paste. In certain instances, pastes contain at least 20% solids. In certain instances, pastes are ointments that do not flow at body temperature.

Gels

In some embodiments, a MYC fusion polypeptide disclosed herein (e.g., TAT-MYC) is formulated as a gel. In certain instances, gels are semisolid (or semi-rigid) systems consisting of dispersions of large organic molecules dispersed in a liquid. In certain instances, gels are water-soluble and are removed using warm water or saline.

Sticks

In some embodiments, a MYC fusion polypeptide disclosed herein (e.g., TAT-MYC) is formulated as a stick. In certain instances, sticks are solid dosage forms that melt at body temperature. In some embodiments, a stick comprises a wax, a polymer, a resin, dry solids fused into a firm mass, and/or fused crystals. In some embodiments, a topical formulation of a MYC fusion polypeptide disclosed herein (e.g., TAT-MYC) is in the form of a styptic pencil (i.e., a stick prepared by (1) heating crystals until they lose their water of crystallization and become molten, and (2) pouring the molten crystals into molds and allowing them to harden). In some embodiments, a topical formulation of a MYC fusion polypeptide disclosed herein (e.g., TAT-MYC) is in the form of stick wherein the stick comprises a wax (e.g., the wax is melted and poured into appropriate molds in which they solidify in stick form).

In some embodiments, a topical formulation of a MYC fusion polypeptide disclosed herein (e.g., TAT-MYC) is in the form of stick wherein the stick comprises a melting base (i.e., a base that softens at body temperature). Examples of melting bases include, but are not limited to, waxes, oils, polymers and gels. In some embodiments, a topical formulation of a MYC fusion polypeptide disclosed herein (e.g., TAT-MYC) is in the form of stick wherein the stick comprises a moisten base (i.e., a base that is activated by the addition of moisture).

Patches

In some embodiments, a MYC fusion polypeptide disclosed herein (e.g., TAT-MYC) is formulated for administration via a patch. In some embodiments, a topical formulation disclosed herein is dissolved and/or dispersed in a polymer or an adhesive. In some embodiments, a patch disclosed herein is constructed for continuous, pulsatile, or on demand delivery of a MYC fusion polypeptide disclosed herein (e.g., TAT-MYC).

Wound Dressings

In some embodiments, a MYC fusion polypeptide disclosed herein (e.g., TAT-MYC) is formulated for administration via a wound dressing. Wound dressings include, but are not limited to gauzes, transparent film dressings, hydrogels, polyurethane foam dressings, hydrocolloids and alginates.

Dermatological Excipients

In some embodiments, a MYC fusion polypeptide disclosed herein (e.g., TAT-MYC) is formulated with a penetration enhancer. Penetration enhancers include, but are not limited to, sodium lauryl sulfate, sodium laurate, polyoxyethylene-20-cetyl ether, laureth-9, sodium dodecylsulfate, dioctyl sodium sulfosuccinate, polyoxyethylene-9-lauryl ether (PLE), Tween 80, nonylphenoxypolyethylene (NP-POE), polysorbates, sodium glycocholate, sodium deoxycholate, sodium taurocholate, sodium taurodihydrofusidate, sodium glycodihydrofusidate, oleic acid, caprylic acid, mono- and di-glycerides, lauric acids, acylcholines, caprylic acids, acylcarnitines, sodium caprates, EDTA, citric acid, salicylates, DMSO, decylmethyl sulfoxide, ethanol, isopropanol, propylene glycol, polyethylene glycol, glycerol, propanediol, and diethylene glycol monoethyl ether.

In some embodiments, a MYC fusion polypeptide disclosed herein (e.g., TAT-MYC) is formulated with a gelling (or thickening) agent. In some embodiments, a topical formulation disclosed herein further comprises from about 0.1% to about 5%, more preferably from about 0.1% to about 3%, and most preferably from about 0.25% to about 2%, of a gelling agent. In certain embodiments, the viscosity of a topical formulation disclosed herein is in the range from about 100 to about 500,000 cP, about 100 cP to about 1,000 cP, about 500 cP to about 1500 cP, about 1000 cP to about 3000 cP, about 2000 cP to about 8,000 cP, about 4,000 cP to about 10,000 cP, about 10,000 cP to about 50,000 cP.

Suitable gelling agents for use in preparation of the gel topical formulation include, but are not limited to, celluloses, cellulose derivatives, cellulose ethers (e.g., carboxymethylcellulose, ethylcellulose, hydroxyethylcellulose, hydroxymethylcellulose, hydroxypropylmethylcellulose, hydroxypropylcellulose, methylcellulose), guar gum, xanthan gum, locust bean gum, alginates (e.g., alginic acid), silicates, starch, tragacanth, carboxyvinyl polymers, carrageenan, paraffin, petrolatum, acacia (gum arabic), agar, aluminum magnesium silicate, sodium alginate, sodium stearate, bladderwrack, bentonite, carbomer, carrageenan, carbopol, xanthan, cellulose, microcrystalline cellulose (MCC), ceratonia, chondrus, dextrose, furcellaran, gelatin, ghatti gum, guar gum, hectorite, lactose, sucrose, maltodextrin, mannitol, sorbitol, honey, maize starch, wheat starch, rice starch, potato starch, gelatin, sterculia gum, polyethylene glycol (e.g. PEG 200-4500), gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly(methoxyethyl methacrylate), poly(methoxyethoxyethyl methacrylate), hydroxypropyl cellulose, hydroxypropylmethyl-cellulose (HPMC), sodium carboxymethyl-cellulose (CMC), silicon dioxide, polyvinylpyrrolidone (PVP: povidone), or combinations thereof.

In some embodiments, a MYC fusion polypeptide disclosed herein (e.g., TAT-MYC) is formulated with an emollient. Emollients include, but are not limited to, castor oil esters, cocoa butter esters, safflower oil esters, cottonseed oil esters, corn oil esters, olive oil esters, cod liver oil esters, almond oil esters, avocado oil esters, palm oil esters, sesame oil esters, squalene esters, kikui oil esters, soybean oil esters, acetylated monoglycerides, ethoxylated glyceryl monostearate, hexyl laurate, isohexyl laurate, isohexyl palmitate, isopropyl palmitate, methyl palmitate, decyloleate, isodecyl oleate, hexadecyl stearate decyl stearate, isopropyl isostearate, methyl isostearate, diisopropyl adipate, diisohexyl adipate, dihexyldecyl adipate, diisopropyl sebacate, lauryl lactate, myristyl lactate, and cetyl lactate, oleyl myristate, oleyl stearate, and oleyl oleate, pelargonic acid, lauric acid, myristic acid, palmitic acid, stearic acid, isostearic acid, hydroxystearic acid, oleic acid, linoleic acid, ricinoleic acid, arachidic acid, behenic acid, erucic acid, lauryl alcohol, myristyl alcohol, cetyl alcohol, hexadecyl alcohol, stearyl alcohol, isostearyl alcohol, hydroxystearyl alcohol, oleyl alcohol, ricinoleyl alcohol, behenyl alcohol, erucyl alcohol, 2-octyl dodecanyl alcohol, lanolin and lanolin derivatives, beeswax, spermaceti, myristyl myristate, stearyl stearate, carnauba wax, candelilla wax, lecithin, and cholesterol.

Combinations

In some embodiments, it is appropriate to administer at least one therapeutic agent described herein in combination with another therapeutic agent. Or, by way of example only, the benefit experienced by a patient is increased by administering one of the compounds described herein with another therapeutic agent (which also includes a therapeutic regimen) that also has therapeutic benefit. In any case, regardless of the disorder, disease or condition being treated, the overall benefit experienced by the patient is, in some embodiments, additive of the two therapeutic agents or in other embodiments, the patient experiences a synergistic benefit.

In some embodiments, the particular choice of compounds depends upon the diagnosis of the attending physicians and their judgment of the condition of the patient and the appropriate treatment protocol. The compounds are optionally administered concurrently (e.g., simultaneously, essentially simultaneously or within the same treatment protocol) or sequentially, depending upon the nature of the disease, disorder, or condition, the condition of the patient, and the actual choice of compounds used. In certain instances, the determination of the order of administration, and the number of repetitions of administration of each therapeutic agent during a treatment protocol, is based on an evaluation of the disorder being treated and the condition of the patient.

In some embodiments, therapeutically-effective dosages vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature. Combination treatment further includes periodic treatments that start and stop at various times to assist with the clinical management of the patient.

In some embodiments of the combination therapies described herein, dosages of the co-administered compounds vary depending on the type of co-drug employed, on the specific drug employed, on the disorder or condition being treated and so forth. In addition, when co-administered with one or more biologically agents, the compound provided herein is optionally administered either simultaneously with the biologically agent(s), or sequentially. In certain instances, if administered sequentially, the attending physician will decide on the appropriate sequence of therapeutic compound described herein in combination with the additional therapeutic agent.

The multiple therapeutic agents (at least one of which is a therapeutic compound described herein) are optionally administered in any order or even simultaneously. If simultaneously, the multiple therapeutic agents are optionally provided in a single, unified form, or in multiple forms (by way of example only, either as a single pill or as two separate pills). In certain instances, one of the therapeutic agents is optionally given in multiple doses. In other instances, both are optionally given as multiple doses. If not simultaneous, the timing between the multiple doses is any suitable timing, e.g., from more than zero weeks to less than four weeks. In some embodiments, the additional therapeutic agent is utilized to achieve remission (partial or complete) of a cancer, whereupon the therapeutic agent described herein (e.g., a compound of any one of Formulas I-V) is subsequently administered. In addition, the combination methods, compositions and formulations are not to be limited to the use of only two agents; the use of multiple therapeutic combinations are also envisioned (including two or more therapeutic compounds described herein).

In some embodiments, a dosage regimen to treat, prevent, or ameliorate the condition(s) for which relief is sought, is modified in accordance with a variety of factors. These factors include the disorder from which the subject suffers, as well as the age, weight, sex, diet, and medical condition of the subject. Thus, in various embodiments, the dosage regimen actually employed varies and deviates from the dosage regimens set forth herein.

In some embodiments, the pharmaceutical agents which make up the combination therapy disclosed herein are provided in a combined dosage form or in separate dosage forms for substantially simultaneous administration. In certain embodiments, the pharmaceutical agents that make up the combination therapy are administered sequentially, with either therapeutic compound being administered by a regimen calling for two-step administration. In some embodiments, two-step administration regimen calls for sequential administration of the agents or spaced-apart administration of the separate agents. In certain embodiments, the time period between the multiple administration steps varies, by way of non-limiting example, from a few minutes to several hours, depending upon the properties of each pharmaceutical agent, such as potency, solubility, bioavailability, plasma half-life and kinetic profile of the pharmaceutical agent.

In addition, the compounds described herein also are optionally used in combination with procedures that provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a gene or gene mutation that is known to be correlated with certain disorders or conditions. In certain embodiments, prophylactic benefit is achieved by administering a therapeutic compound described herein to an individual whose proliferative disorder (e.g., cancer) is in remission (e.g., partial or complete).

In some embodiments, the compounds described herein and combination therapies are administered before, during or after the occurrence of a disorder or condition. Timing of administering the composition containing a compound is optionally varied to suit the needs of the individual treated. Thus, in certain embodiments, the compounds are used as a prophylactic and are administered continuously to subjects with a propensity to develop conditions or disorders in order to prevent the occurrence of the disorder or condition. In some embodiments, the compounds and compositions are administered to an individual during or as soon as possible after the onset of the symptoms. The administration of the compounds is optionally initiated within the first 48 hours of the onset of the symptoms, within the first 6 hours of the onset of the symptoms, or within 3 hours of the onset of the symptoms. The initial administration is achieved by any route practical, such as, for example, an intravenous injection, a bolus injection, infusion over 5 minutes to about 5 hours, a pill, a capsule, transdermal patch, buccal delivery, and the like, or combination thereof. In some embodiments, the compound should be administered as soon as is practicable after the onset of a disorder or condition is detected or suspected, and for a length of time necessary for the treatment of the disorder, such as, for example, from more than 1 month to about 3 months. The length of treatment is optionally varied for each subject based on known criteria. In exemplary embodiments, the compound or a formulation containing the compound is administered for at least 2 weeks, between more than 1 month to about 5 years, or from more than 1 month to about 3 years.

In some embodiments, therapeutic agents are combined with or utilized in combination with one or more of the following therapeutic agents in any combination: Akt selective inhibitors; PI3K inhibitors; polypeptide kinase C (PKC) inhibitors; farnesyltransferase inhibitors; inhibitors of sarco/ endoplasmic reticulum Ca2+ ATPase; $Ca^{++}$/calmodulin (CaM)-dependent polypeptide kinase inhibitors; cyclin-dependent kinase inhibitors; PPD (p-phenylenediamine); D609 (tricyclodecan-9-yl xanthogenate); PP1 (4-Amino-5-(4-methylphenyl)-7-(t-butyl)pyrazolo[3,4-d]-pyrimidine);

AG-879 (alpha-Cyano-(3,5-di-t-butyl-4-hydroxy)thiocinnamide); BAY 11-7082 ((E)-3-(4-Methylphenylsulfonyl)-2-propenenitrile); thapsigargin, or RK-682 (3-Hexadecanoyl-5-hydroxymethyl-tetronic acid).

Immunosuppressants include, by way of non-limiting example, Sirolimus (rapamycin), cyclosporin, FK506, cypermethrin, deltamethrin, fenvalerate, tyrphostin 8, methotrexate, piceatannol, genistein, tacrolimus, rapamicin, cyclophosphamide, azathioprine, mercaptopurine, mycophenolate, and FTY720.

Akt selective inhibitors include, by way of non-limiting example, SH4 (1L-6-hydroxymethyl-chiro-inositol 2-R-2-O-methyl-3-O-octadecylcarbonate); SH-5 (D-3-deoxy-2-O-methyl-myo inositol 1-(R)-2-methoxy-3-(octadecyloxy) propyl hydrogen phosphate); and SH-6 (D-2,3-dieoxy-myo inositol 1-(R)-2-methoxy-3-(octadecyloxy) propyl hydrogen phosphate).

PI3K inhibitors include, by way of non-limiting example, wortmannin; LY294002 (2-(4-morpholinyl)-8-phenyl-4H-1-benzopyran-4-one); D000 (Upstate, Milton Keynes, United Kingdom); and D121 (3-phenyl-2-(9H-purin-6-ylsulfanyl-methyl)-3H-quinazolin-4-one).

By way of non-limiting example, protein kinase C (PKC) inhibitors include Ro-318220 (3-[1-[3-(amidinothio)propyl]-1H-indoyl-3-yl]-3-(1-methyl-1H-indoyl-3-yl) maleimide methane sulfonate); Gö6976 (12-(2-cyanoethyl)-6,7,12, 13-tetrahydro-13-methyl-5-oxo-5H-indolo(2,3-a)pyrrolo(3, 4-c)-carbazole); staurosporin; rottlerin; calphastin C; GF 109203X (3-[1-(Dimethylaminopropyl)indol-3-yl]-4-(indol-3-yl)maleimide hydrochloride); hypericin; sphingosine; miltefosine; palmitoyl-DL-carnitine Cl; rottlerin; and 2,2',3, 3',4,4'-hexahydroxy-1,1'-biphenyl-6,6'-dimenthol dimethylether.

By way of non-limiting example, farmesyltransferase inhibitors include L-744,832 ($C_{26}H_{45}N_3O_6S_2$ 2 HCl); or Sarasar (SCH66336 or lonafarnib).

By way of non-limiting example, $Ca^{++}$/calmodulin (CaM)-dependent polypeptide kinase inhibitors include: 2-hydroxy-5-(2,5-dihydroxybenzylamino)benzoic acid; KN-62 (1-[N,O-bis(5-isoquinolinesulfonyl)-N-methyl-L-tyrosyl]-4-phenylpiperazine); KN-93 (2[N-(2-hydroxyethyl)]-N-(4methoxybenzenesulfonyl)]amino-N-(4-chlorocinnamyl)-N-methylbenzylamine); or staurosporine (AM-2282).

By way of non-limiting example, cyclin-dependent kinase inhibitors include: roscovitine (Seliciclib or CYC202); purvalanol A; or indirubin.

Methods of Dosing and Treatment Regimens

In some embodiments, an agent and/or composition described herein is used in the preparation of vaccines for immunization against pathogens (e.g. hepatitis A; hepatitis B; polio; measles; mumps; rubella; diphtheria; pertussis; tetanus; influenza; varicella zoster virus; rotavirus; influenza; meningococcal disease; pneumonia; smallpox; cholera; bubonic plague; yellow fever; tuberculosis: human paplomavirus) wherein an up-regulation of an immune response would be beneficial to said treatment. In some embodiments, an agent described herein is incorporated into the formulation of a vaccine. In some embodiments, an agent described herein is a vaccine adjuvant. In some embodiments, the volume of a vaccine formulation for injection is from about 50 μl to about 5 ml. In some embodiments, the volume of a vaccine formulation for injection is from about 100 µl to about 3.5 ml. In some embodiments, the volume of a vaccine formulation for injection is from about 200 µl to about 2 ml. In some embodiments, the volume of a vaccine formulation for injection is from about 350 µl to about 1 ml. In some embodiments, the volume of a vaccine formulation for injection is about 500 µl. The volume of the vaccine is determined by the method of administration. In certain instances, the vaccine is administered as a subcutaneous or intradermal injection. In certain instances, the vaccine is administered as intramuscular injection. In some embodiments, the vaccine is administered as 1 dose. In some embodiments, the vaccine is administered in multiple doses (e.g. in booster shots).

In some embodiments, an agent and/or composition described herein is used in the preparation of medicaments for the prophylactic and/or therapeutic treatment of disorders that would benefit, at least in part, from a down-regulation of an immune response (e.g. autoimmune disorders, transplant rejection).

In some embodiments, an agent and/or composition described herein is used in a method of treating a disorder (e.g. hepatitis A; hepatitis B; polio; measles; mumps; rubella; diphtheria; pertussis; tetanus; influenza; varicella zoster virus; rotavirus; influenza; meningococcal disease; pneumonia; smallpox; cholera; bubonic plague; yellow fever; tuberculosis: human paplomavirus, and a cancer) wherein an up-regulation of an immune response would be beneficial to said treatment. In some embodiments, an agent and/or composition described herein is used in a method of prophylactic and/or therapeutic treatment of a disorder that would benefit, at least in part, from a down-regulation of an immune response (e.g. autoimmune disorders, transplant rejection).

In certain instances wherein the patient's condition does not improve, upon the doctor's discretion the administration of an agent or composition described herein is optionally administered chronically, that is, for an extended period of time, including throughout the duration of the patient's life in order to ameliorate or otherwise control or limit the symptoms of the patient's disorder.

In the case wherein the patient's status does improve, upon the doctor's discretion the administration of an agent or composition described herein is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the symptoms, to a level at which the improved disease, disorder or condition is retained. In some embodiments, patients require intermittent treatment on a long-term basis upon any recurrence of symptoms.

In some embodiments, the agents or compositions described herein are in unit dosage forms suitable for single administration of precise dosages. In unit dosage form, the formulation is divided into unit doses containing appropriate quantities of an agent or composition described herein. In some embodiments, the unit dosage is in the form of a package containing discrete quantities of the formulation. Non-limiting examples are packaged tablets or capsules, and powders in vials or ampoules. In some embodiments, aqueous suspension compositions are packaged in single-dose non-reclosable containers. Alternatively, multiple-dose reclosable containers are used, in which case it is typical to include a preservative in the composition. By way of example only, formulations for parenteral injection are presented in unit dosage form, which include, but are not limited to ampoules, or in multi dose containers, with an added preservative.

The daily dosages appropriate for an agent or composition described herein are from about 0.01 to 10.0 mg/kg per body weight. In some embodiments, the daily dosages appropriate for an agent or composition described herein are from about 0.05 to 7.5 mg/kg per body weight. In some embodiments, the daily dosages appropriate for an agent or composition described herein are from about 0.1 to 5.0 mg/kg per body weight. In some embodiments, the daily dosages appropriate for an agent or composition described herein are from about 0.25 to 2.5 mg/kg per body weight. In some embodiments, the daily dosages appropriate for an agent or composition described herein are from about 0.5 to 1.0 mg/kg per body weight. An indicated daily dosage in the larger mammal, including, but not limited to, humans, is in the range from about 0.5 mg to about 100 mg, conveniently administered in divided doses, including, but not limited to, up to four times a day or in extended release form. Suitable unit dosage forms for oral administration include from more than 1 to 50 mg active ingredient. The foregoing ranges are merely suggestive, as the number of variables in regard to an individual treatment regime is large, and considerable excursions from these recommended values are not uncommon. Such dosages are optionally altered depending on a number of variables, not limited to the activity of the agent or composition described herein used, the disorder or condition to be treated, the mode of administration, the requirements of the individual subject, the severity of the disorder or condition being treated, and the judgment of the practitioner.

Toxicity and therapeutic efficacy of such therapeutic regimens are optionally determined in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index, which is expressed as the ratio between LD50 and ED50. An agent or compositions described herein exhibiting high therapeutic indices is preferred. The data obtained from cell culture assays and animal studies are optionally used in formulating a range of dosage for use in human. The dosage of such an agent or composition described herein lies preferably within a range of circulating concentrations that include the ED50 with minimal toxicity. The dosage optionally varies within this range depending upon the dosage form employed and the route of administration utilized.

EXAMPLES

The following examples are for illustrative purposes only and are non-limiting embodiments. Many modifications, equivalents, and variations of the present invention are possible in light of the above teachings, therefore, it is to be understood that within the scope of the appended claims, the invention may be practiced other than as specifically described.

Example 1—Assay Using a Reporter Construct

A plurality of cells are transformed with a reporter construct. The reporter construct has FLuc under control of an ODC promoter. The cells are divided into 96 aliquots using a standard 96-well plate. Each well is administered a different small molecule. The small molecule is incubated with the cells for 6 hours. The level of expression of the luciferase is determined using fluorescent microscopy. Agents which induce the expression of the luciferase gene are validated in vitro.

Example 2—Construction of a TAT-MYC Fusion Peptide

Construction of p-TAT-MYC

Plasmid pTAT-Myc-V5-6×His was made by PCR amplification of the coding regions for human MYC using a forward primer that contains an in frame N-terminal 9-amino-acid sequence of the TAT protein transduction domain of HIV-1 (RKKRRQRRR) (SEQ ID NO:5), and a reverse primer that removed the stop codon. The PCR product was then cloned into pETIOI/D-Topo (Invitrogen) vector, which includes a C-terminal V5 epitope and 6×-histidine purification tag.

Bacterial Strain Used for Protein Expression

BL-21 RARE cells were created by transforming BL-21 Star™ E. coli strain (Invitrogen) with pRARE (CamR), isolated from BL21 Rosetta cells (Novagen), that express tRNAs for AGG, AGA, AUA, CUA, CCC, GGA codons.

Protein Induction and Purification pTAT-Myc-V5-6×His was transformed into BL21 RARE cells and grown on TB/Amp/Cam plate at 37° C. overnight. An isolated colony was used to inoculate a 5 ml TB/Amp/Cam starter culture and grown at 37° C. overnight. 1 liter of TB/Amp/Cam broth was inoculated with the 5 ml starter culture and grown to an OD600 of 0.5, and induced with 0.5 mM IPTG at 37° C. for 3 hrs.

Bacterial cells were pelleted by centrifugation and the cell pellet was resuspended in lysis buffer (8 M urea, 100 mM $NaH_2PO_4$, 10 mM Tris pH to 8.0) and lysed at room temperature overnight on a shaker. The lysate was cleared by centrifugation at 29,000×g for 30 min and the supernatant was applied to a nickel nitrilotriacetate affinity column (Qiagen) using gravity flow. The column was washed with 25 volumes of lysis buffer containing 10 mM imidazole followed by elution with lysis buffer containing 100 mM imidazole.

Protein was concentrated using an Amicon Ultra centrifugal filter device (10,000 MWCO) and dialyzed in a stepwise fashion into dialysis buffer (50 mM $NaH_2PO_4$, 5 mM Tris pH 7.0, 450 mM NaCl, 5% glycerol, 1 mM DTT). The dialysis went as follows: 2 hours in dialysis buffer containing 4M urea, 2 hours in buffer with 2M urea, then 2 hrs in dialysis buffer alone. Purity and size of proteins were verified using SDS-PAGE electrophoresis and either coomassie blue staining or western blot with anti-V5 (1:5000; Invitrogen) or anti-c-Myc (N-262, 1:2000; Santa Cruz Biotechnology) antibodies.

Protein concentration was measured by Bradford protein assay (Sigma) compared to a standard curve of bovine serum albumin.

Example 3—Effect of TAT-Myc Fusion Peptide on Immune Responses

The TAT-MYC fusion peptide is evaluated in vitro as a regulator of an immune response. A primary T-cell activation culture is incubated with the TAT-MYC fusion peptide for 72 hours. The culture is then stained with CFSE. Following staining with CFSE, the culture is analyzed by FACS.

Example 4—Effect of TAT-Myc Fusion Peptide on Immune Responses

The TAT-MYC fusion peptide is evaluated in vivo as a regulator of an immune response. A mouse is immunized against NP-KHL by administering NP-KHL to the mouse. Immediately after immunization against the antigen, the TAT-MYC fusion peptide is administered to the mouse. Twenty-four hours after the immunization serum is taken from the mouse. The serum is analyzed for antibodies. Alternatively, the TAT-MYC fusion peptide is administered concurrently with immunization, or preceding immunization.

Example 5—Effect of IM TAT-MYC as a Vaccine Adjuvant

This will be a double-blind, randomized, placebo-controlled study. It is designed to assess immunological memory following administration of an influenza vaccine and a TAT-MYC fusion peptide.

Participants are divided into two groups. Group I will be administered an influenza vaccine and saline. Group II will be administered an influenza vaccine and the TAT-MYC fusion peptide.

Primary Objective

To assess the immunological effects of a TAT-MYC fusion peptide administered by intramuscular (IM) injection to individuals receiving an influenza vaccine.

Secondary Objectives

To assess the safety and tolerability of a TAT-MYC fusion peptide administered by intramuscular injection to individuals receiving an influenza vaccine.

Methodology

On Day=0, both Group I and Group II are administered a single dose of the same influenza vaccine. Subjects are monitored for 2 hours for negative side-effects.

All individuals in Group I not exhibiting negative side-effects are administered 20 uL of saline by IM injection.

All individuals in Group II not exhibiting negative side-effects are administered 20 uL of the TAT-MYC fusion peptide by IM injection.

Blood is drawn from all individuals on Day=1. T-cell counts are determined and recorded.

On Day=20, all individuals are challenged with antigens from relevant influenza strains. Blood is drawn for all individuals 1 hour after challenge, 6 hours after challenge, 12 hours after challenge, and 24 hours after challenge. T-cell levels are determined.

Example 6—Effect of Topical TAT-MYC as a Vaccine Adjuvant

This will be a double-blind, randomized, placebo-controlled study. It is designed to assess immunological memory following administration of an influenza vaccine and a TAT-MYC fusion peptide.

Participants are divided into two groups. Group I will be administered an influenza vaccine and saline. Group II will be administered an influenza vaccine and the TAT-MYC fusion peptide.

Primary Objective

To assess the immunological effects of a TAT-MYC fusion peptide administered topically to individuals receiving an influenza vaccine.

Secondary Objectives

To assess the safety and tolerability of a TAT-MYC fusion peptide administered topically to individuals receiving an influenza vaccine.

Methodology

On Day=0, both Group I and Group II are administered a single dose of the same influenza vaccine. Subjects are monitored for 2 hours for negative side-effects.

All individuals in Group I not exhibiting negative side-effects are given one application of the placebo lotion. Individuals are instructed to apply the lotion onto the skin at the site of the vaccination.

All individuals in Group II not exhibiting negative side-effects are given one application of the TAT-MYC lotion. Individuals are instructed to apply the lotion onto the skin at the site of the vaccination.

Blood is drawn from all individuals on Day=1. T-cell counts are determined and recorded.

On Day=20, all individuals are challenged with antigens from relevant influenza strains. Blood is drawn for all individuals 1 hour after challenge, 6 hours after challenge, 12 hours after challenge, and 24 hours after challenge. T-cell levels are determined.

Example 7—Effect on RA of an Agent that Down-Regulates MYC Expression

Primary Objective

To assess the steady-state trough serum concentrations of an agent that dereases the expression of MYC as identified by a method disclosed herein (hereinafter, "Agent X") following weekly subcutaneous dosing in subjects with active rheumatoid arthritis (RA).

Secondary Objectives

To assess the safety and tolerability of Agent X administered subcutaneously to individuals with RA; to assess the immunogenicity of Agent X administered subcutaneously in individuals with RA; and to examine the effect of subcutaneous administration of Agent X on serum levels of rheumatoid factor (RF) in individuals with RA.

Methodology

This will be a double-blind, randomized, placebo-controlled, parallel-group, multiple-dose study. It will be designed to assess the steady-state trough serum concentrations of Agent X following subcutaneous administration in subjects with RA.

Subjects will be randomized according to a computer generated randomization scheme, in a 3:1 ratio, to receive either Agent X or placebo in 1 of 5 parallel groups based on body weight obtained at a screening visit.

On Day 1, subjects will receive a single IV infusion (loading dose) of Agent X or placebo, based on their weight range. Agent X or placebo will be administered intravenously over ~30 minutes using a calibrated, constant-rate infusion pump prior to starting subcutaneous treatment. Approximately 1 hour after the completion of the IV infusion, subjects will receive their assigned subcutaneous dose of Agent X or placebo drawn from a vial or using a pre-filled syringe. Agent X or placebo will be administered by clinical study site staff weekly by the subcutaneous route, at the same dose as the subcutaneous dose on Day 1 for a total of 12 subcutaneous injections.

Subjects will be monitored for adverse events (AEs) throughout the duration of the study. Physical examinations, vital sign measurements, and clinical laboratory evaluations will be performed at selected times throughout the study. Blood samples for PK analysis will be collected on Day 1 prior to and at the end of the IV infusion. In addition, blood samples will be collected prior to each weekly SC dose of agent X on Days 8, 15, 22, 29, 36, 43, 50, 57, 64, 71, and 78 for the assessment of steady-state Cmin concentrations. A single blood sample will also be collected on Days 72, 74, 75, and 76 for evaluation of steady-state Cmax, Tmax, and AUC(TAU), where TAU=7 days, and at study discharge (Day 85). Blood samples for assessment of immunogenicity will be obtained prior to the administration of agent X on Days 1, 15, 29, 43, 57, 71, and 85. Blood samples for the determination of RF will be obtained prior to dosing on Days 1, 8, 15, 29, 57, and 85.

Subjects who complete the 12 weeks of subcutaneous dosing of Agent X or placebo are eligible to enter into a long term extension (LTE). For subjects who entered the LTE, the first dose of Agent X will be administered on Day 85.

Number of Subjects

Between 48 and 72 subjects are to be randomized to study treatment.

Diagnosis and Criteria for Inclusion

Men or women with active RA who are above 18 will eligible for participation in this study. Subjects must meet the classification criteria of the American College of Rheumatology (ACR) (formerly American Rheumatism Association (ARA)), for RA and had active disorder. Subjects must have had RA for at least 1 year from the time of initial diagnosis.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A method of treating a viral infection, comprising administering to an individual in need thereof a fusion peptide comprising:
   a. a transporter peptide sequence; and
   b. a MYC polypeptide sequence,
wherein the transporter peptide sequence transports the fusion peptide into the nucleus of an immune cell in the individual.

2. The method of claim 1, wherein the fusion peptide enhances the immune response against the virus.

3. The method of claim 1, wherein the immune cell is a primary lymphocyte.

4. The method of claim 1, wherein the individual has a decreased immune response to the virus in the absence of the fusion peptide.

5. The method of claim 1, wherein the virus is selected from the group consisting of hepatitis A; hepatitis B; polio; measles; mumps; rubella; influenza; varicella zoster virus; rotavirus; smallpox; yellow fever; and human papillomavirus.

6. The method of claim 1, wherein the virus is an influenza virus.

7. The method of claim 5, further comprising administering a vaccine for the virus.

8. The method of claim 1, wherein the fusion peptide has Formula (I):

transporter peptide sequence-MYC sequence.

9. The method of claim 1, wherein the fusion peptide has Formula (II):

transporter peptide sequence-X-MYC sequence, wherein —X— is at least one molecule that links the transporter peptide sequence and the MYC sequence.

10. The method of claim 1, wherein the fusion peptide has Formula (II): transporter peptide sequence-X-MYC sequence, wherein in X is at least one amino acid.

11. The method of claim 1, wherein the fusion peptide is administered orally, parenterally, intranasally, buccally, rectally, or intravenously.

12. The method of claim 1, wherein the fusion peptide is administered intramuscularly, subcutaneously, topically or transdermally.

13. The method of claim 1, wherein the fusion peptide is formulated as a delayed release formulation or as an extended release formulation.

14. A method of increasing an immune response to a virus, comprising administering to an individual that has been exposed to a viral antigen from the virus a fusion peptide comprising:
   a. a transporter peptide sequence; and
   b. a MYC polypeptide sequence,
wherein the transporter peptide sequence transports the fusion peptide into the nucleus of an immune cell in the individual.

15. The method of claim 14, wherein the individual has a decreased immune response to the virus in the absence of the fusion peptide.

16. The method of claim 14, wherein the virus is selected from the group consisting of hepatitis A; hepatitis B; polio; measles; mumps; rubella; influenza; varicella zoster virus; rotavirus; smallpox; yellow fever; and human papillomavirus.

17. The method of claim 16, wherein the virus is an influenza virus.

18. The method of claim 16, further comprising administering a vaccine for the virus.

19. The method of claim 14, wherein the fusion peptide is administered orally, parenterally, intranasally, buccally, rectally, or intravenously.

20. The method of claim 14, wherein the fusion peptide is administered intramuscularly, subcutaneously, topically or transdermally.

* * * * *

SEQUENCE LISTING

<160> NUMBER OF SEQ ID NOS: 6

<210> SEQ ID NO 1
<211> LENGTH: 459
<212> TYPE: PRT
<213> ORGANISM: Homo sapiens

<400> SEQUENCE: 1

```
Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
            20                  25                  30

Ser Val Gln Pro Tyr Phe Tyr Cys Asp Glu Glu Glu Asn Phe Tyr Gln
        35                  40                  45

Gln Gln Gln Gln Ser Glu Leu Gln Pro Ala Pro Ser Glu Asp Ile
    50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Ser Phe Ser Thr Ala Asp
            100                 105                 110

Gln Leu Glu Met Val Thr Glu Leu Leu Gly Gly Asp Met Val Asn Gln
        115                 120                 125

Ser Phe Ile Cys Asp Pro Asp Asp Glu Thr Phe Ile Lys Asn Ile Ile
    130                 135                 140

Ile Gln Asp Cys Met Trp Ser Gly Phe Ser Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
            180                 185                 190

Leu Gln Asp Leu Ser Ala Ala Ala Ser Glu Cys Ile Asp Pro Ser Val
        195                 200                 205

Val Phe Pro Tyr Pro Leu Asn Asp Ser Ser Ser Pro Lys Ser Cys Ala
    210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Gln Glu
            260                 265                 270

Asp Glu Glu Glu Ile Asp Val Val Ser Val Glu Lys Arg Gln Ala Pro
    275                 280                 285

Gly Lys Arg Ser Glu Ser Gly Ser Pro Ser Ala Gly Gly His Ser Lys
    290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
        355                 360                 365
```

```
Val Lys Arg Arg Thr His Asn Val Leu Glu Arg Gln Arg Arg Asn Glu
    370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
                420                 425                 430

Asp Leu Leu Arg Lys Arg Arg Glu Gln Leu Lys His Lys Leu Glu Gln
            435                 440                 445

Leu Arg Lys Gly Glu Leu Asn Ser Lys Leu Glu
        450                 455

<210> SEQ ID NO 2
<211> LENGTH: 492
<212> TYPE: PRT
<213> ORGANISM: Artificial Sequence
<220> FEATURE:
<223> OTHER INFORMATION: Synthetic polypeptide

<400> SEQUENCE: 2

Met Arg Lys Lys Arg Arg Gln Arg Arg Met Asp Phe Phe Arg Val
1               5                   10                  15

Val Glu Asn Gln Gln Pro Pro Ala Thr Met Pro Leu Asn Val Ser Phe
                20                  25                  30

Thr Asn Arg Asn Tyr Asp Leu Asp Tyr Asp Ser Val Gln Pro Tyr Phe
            35                  40                  45

Tyr Cys Asp Glu Glu Asn Phe Tyr Gln Gln Gln Gln Gln Ser Glu
    50                  55                  60

Leu Gln Pro Pro Ala Pro Ser Glu Asp Ile Trp Lys Lys Phe Glu Leu
65                  70                  75                  80

Leu Pro Thr Pro Pro Leu Ser Pro Ser Arg Arg Ser Gly Leu Cys Ser
                85                  90                  95

Pro Ser Tyr Val Ala Val Thr Pro Phe Ser Leu Arg Gly Asp Asn Asp
                100                 105                 110

Gly Gly Gly Gly Ser Phe Ser Thr Ala Asp Gln Leu Glu Met Val Thr
            115                 120                 125

Glu Leu Leu Gly Gly Asp Met Val Asn Gln Ser Phe Ile Cys Asp Pro
130                 135                 140

Asp Asp Glu Thr Phe Ile Lys Asn Ile Ile Ile Gln Asp Cys Met Trp
145                 150                 155                 160

Ser Gly Phe Ser Ala Ala Ala Lys Leu Val Ser Glu Lys Leu Ala Ser
                165                 170                 175

Tyr Gln Ala Ala Arg Lys Asp Ser Gly Ser Pro Asn Pro Ala Arg Gly
            180                 185                 190

His Ser Val Cys Ser Thr Ser Ser Leu Tyr Leu Gln Asp Leu Ser Ala
        195                 200                 205

Ala Ala Ser Glu Cys Ile Asp Pro Ser Val Val Phe Pro Tyr Pro Leu
    210                 215                 220

Asn Asp Ser Ser Ser Pro Lys Ser Cys Ala Ser Gln Asp Ser Ser Ala
225                 230                 235                 240

Phe Ser Pro Ser Ser Asp Ser Leu Leu Ser Ser Thr Glu Ser Ser Pro
                245                 250                 255

Gln Gly Ser Pro Glu Pro Leu Val Leu His Glu Glu Thr Pro Pro Thr
            260                 265                 270
```

```
Thr Ser Ser Asp Ser Glu Glu Gln Glu Asp Glu Glu Ile Asp
            275                 280                 285

Val Val Ser Val Glu Lys Arg Gln Ala Pro Gly Lys Arg Ser Glu Ser
290                 295                 300

Gly Ser Pro Ser Ala Gly Gly His Ser Lys Pro Pro His Ser Pro Leu
305                 310                 315                 320

Val Leu Lys Arg Cys His Val Ser Thr His Gln His Asn Tyr Ala Ala
                325                 330                 335

Pro Pro Ser Thr Arg Lys Asp Tyr Pro Ala Ala Lys Arg Val Lys Leu
            340                 345                 350

Asp Ser Val Arg Val Leu Arg Gln Ile Ser Asn Asn Arg Lys Cys Thr
355                 360                 365

Ser Pro Arg Ser Ser Asp Thr Glu Glu Asn Val Lys Arg Arg Thr His
            370                 375                 380

Asn Val Leu Glu Arg Gln Arg Arg Asn Glu Leu Lys Arg Ser Phe Phe
385                 390                 395                 400

Ala Leu Arg Asp Gln Ile Pro Glu Leu Glu Asn Asn Glu Lys Ala Pro
                405                 410                 415

Lys Val Val Ile Leu Lys Lys Ala Thr Ala Tyr Ile Leu Ser Val Gln
            420                 425                 430

Ala Glu Glu Gln Lys Leu Ile Ser Glu Glu Asp Leu Leu Arg Lys Arg
        435                 440                 445

Arg Glu Gln Leu Lys His Lys Leu Glu Gln Leu Arg Lys Gly Glu Leu
    450                 455                 460

Asn Ser Lys Leu Glu Gly Lys Pro Ile Pro Asn Pro Leu Leu Gly Leu
465                 470                 475                 480

Asp Ser Thr Arg Thr Gly His His His His His His
                485                 490
```

<210> SEQ ID NO 3
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 3

```
His His His His His His
1               5
```

<210> SEQ ID NO 4
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 4

```
Gly Lys Pro Ile Pro Asn Pro Leu Leu Gly Leu Asp Ser Thr
1               5                   10
```

<210> SEQ ID NO 5
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 5

```
Ile Pro Asn Pro Leu Leu Gly Leu Asp
```

```
1               5

<210> SEQ ID NO 6
<211> LENGTH: 9
<212> TYPE: PRT
<213> ORGANISM: Human immunodeficiency virus

<400> SEQUENCE: 6

Arg Lys Lys Arg Arg Gln Arg Arg Arg
1               5
```